United States Patent
Drewniak et al.

(10) Patent No.: US 9,328,397 B2
(45) Date of Patent: May 3, 2016

(54) REMOVAL OF ARSENIC USING A DISSIMILATORY ARSENIC REDUCTASE

(71) Applicant: UNIWERSYTET WARSZAWSKI, Warszawa (PL)

(72) Inventors: Lukasz Drewniak, Skarzysko-Kamienna (PL); Aleksandra Sklodowska, Warszawa (PL); Monika Radlinska, Warszawa (PL); Robert Stasiuk, Sarnaki (PL)

(73) Assignee: UNIWERSYTET WARSZAWSKI, Warsaw (PL)

( * ) Notice: Subject to any disclaimer, the term of this patent is extended or adjusted under 35 U.S.C. 154(b) by 0 days.

(21) Appl. No.: 14/678,143

(22) Filed: Apr. 3, 2015

(65) Prior Publication Data

US 2015/0267276 A1    Sep. 24, 2015

Related U.S. Application Data

(63) Continuation-in-part of application No. PCT/IB2013/059773, filed on Oct. 30, 2013.

(30) Foreign Application Priority Data

Jun. 19, 2013 (PL) .......................... 404376

(51) Int. Cl.

| | |
|---|---|
| C12N 15/63 | (2006.01) |
| C22B 3/18 | (2006.01) |
| C12N 9/02 | (2006.01) |
| C07K 14/195 | (2006.01) |
| C12N 9/14 | (2006.01) |
| C02F 3/34 | (2006.01) |
| C12P 3/00 | (2006.01) |
| C12R 1/01 | (2006.01) |
| C22B 1/11 | (2006.01) |
| C02F 3/28 | (2006.01) |
| C02F 101/10 | (2006.01) |

(52) U.S. Cl.
CPC ... *C22B 3/18* (2013.01); *C02F 3/34* (2013.01); *C02F 3/342* (2013.01); *C07K 14/195* (2013.01); *C12N 9/0004* (2013.01); *C12N 9/14* (2013.01); *C12P 3/00* (2013.01); *C12R 1/01* (2013.01); *C12Y 120/99001* (2013.01); *C12Y 306/03016* (2013.01); *C22B 1/11* (2013.01); *C02F 3/28* (2013.01); *C02F 2101/103* (2013.01); *C12Y 120/04001* (2013.01); *Y02P 20/52* (2015.11)

(58) Field of Classification Search
None
See application file for complete search history.

(56) References Cited

PUBLICATIONS

Ma et al. Rejection of arsenic minerals in sulfide flotation—A literature review. International Journal of Mineral Processing vol. 93, Issue 2, Oct. 1, 2009, pp. 89-94.*
L. Drewniak, et al., Arsenic Release From Gold Mine Rocks Mediated by the Activity of Indigenous Bacteria, Hydrometallurgy (2010) vol. 104, p. 437-442.
Lukasz Drewniak, et al., The Contribution of Microbial Mats to the Arsenic Geochemistry of an Ancient Gold Mine, Environmental Pollution (2012) vol. 162, p. 190-201.
X. Ma, et al., Rejection of Arsenic Minerals in Sulfide Flotation—A Literature Review, Int. J. Miner. Process, (2009) vol. 93, p. 89-94.
D. Malasarn, et al., arrA Is a Reliable Marker for As(V) Respiration, Science, Oct. 15, 2004, vol. 306, p. 455.
Joanne M. Santini, et al., A New Chemolithoautotrophic Arsenic-Oxidizing Bacterium Isolated From a Gold Mine: Phylogenic, Physiological, and Preliminary Biochemical Studies, Applied and Environmental Microbiology (2000) vol. 66, No. 1, p. 92-97.
Database EMBL: Accession No. HQ316511: May 1, 2011, Uncultured Bacterium clone ZSARR21 Arsenate Respiratory Reductase-Like (arrA) Gene, partial sequence.
Database EMBL: Accession No. AY660886: Oct. 2, 2004, *Shewanella* sp. HAR-4 Arsenate Respiratory Reductase (arrA) Gene, partial cds.
International Search Report and Written Opinion for PCT/IB2013/059773 dated Oct. 28, 2914.

* cited by examiner

*Primary Examiner* — Michele K Joike
(74) *Attorney, Agent, or Firm* — Vedder Price P.C.; Thomas J. Kowalski; Deborah L. Lu

(57) ABSTRACT

The object of the invention is the plasmid pSheB, particularly a plasmid which may comprise a fragment of pSheB including the arr module and functional derivatives thereof, and strains containing such a plasmid, preferably the *Shewanella* sp. strain, deposited as KKP 2045p, which are capable of removing arsenic by dissolution of minerals and reduction of arsenates to arsenites. The object of the invention is also the method and the use of such bacterial strains or compositions which may comprise them, for the selective removal of arsenic from mineral resources, raw materials industry waste or soil.

21 Claims, 5 Drawing Sheets

Fig. 3A-B

Fig. 7A-B
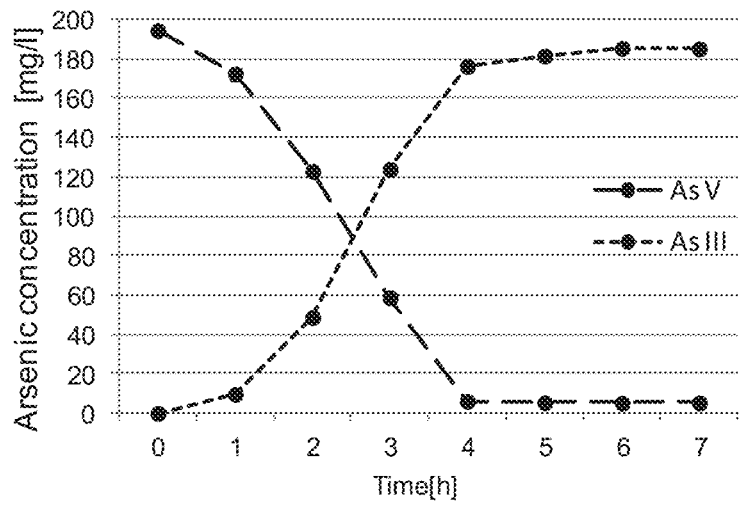
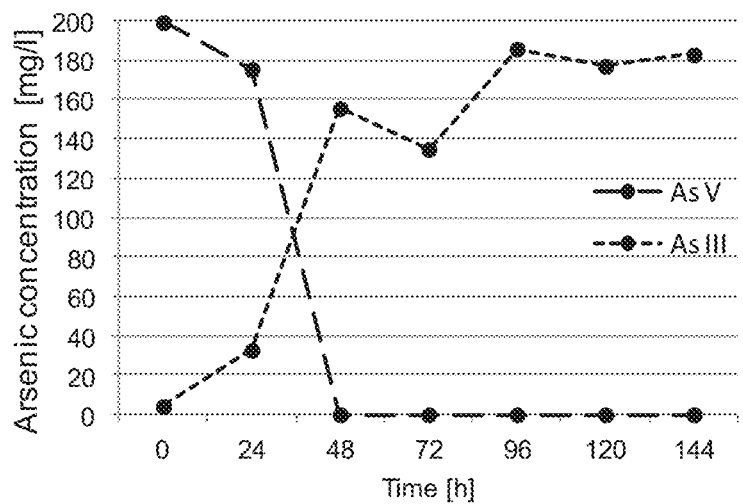

REMOVAL OF ARSENIC USING A DISSIMILATORY ARSENIC REDUCTASE

RELATED APPLICATIONS AND INCORPORATION BY REFERENCE

This application is a continuation-in-part application of international patent application Ser. No. PCT/IB2013/059773 filed 30 Oct. 2013, which published as PCT Publication No. WO 2014/203046 on 24 Dec. 2014, which claims benefit of Polish patent application Serial No. P.404376 filed 19 Jun. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on May 19, 2015, is named 46538.00.2005_SL.txt and is 107,087 bytes in size.

FIELD OF THE INVENTION

The object of the invention is the plasmid pSheB, particularity a plasmid which may comprise a fragment of pSheB which may comprise the arr module or functional derivatives thereof, and strains which may comprise such a plasmid, particularity *Shewanella* sp. O23S strain, which are capable of removing arsenic from mineral resources, raw materials industry waste and soils, in particular, post-mining (e.g. soils) under anaerobic conditions, by dissolution of minerals and reduction of arsenates to arsenites. The object of the invention is also the method and the use of such bacterial strains or a composition which may comprise them, for the selective removal of arsenic from mineral resources, raw materials industry waste or the soil.

BACKGROUND OF THE INVENTION

Arsenic is an element that very often co-occurs in copper minerals and constitutes their specific impurity. In pyrometallurgical processes of roasting and smelting of copper concentrates, volatile arsenic compounds are released into the atmosphere, which, due to the toxicity of these compounds, constitutes a major threat to the environment. During the smelting process, most of the arsenic is removed as a volatile compound $As_4O_6$ at concentrations up to 0.5 mg/l, while only 0.04%-0.06% is removed in a solid, stable form with slags [Piret, 1999]. Apart from the volatile arsenic compounds, high concentrations of arsenic are also found in dusts. For this reason, it is very important from both an economic and an environmental point of view, to develop an effective method of controlled removal of arsenic form copper deposits and the products of their processing.

In order for the removal of arsenic from copper minerals to bring the expected economic and environmental benefits, this process must be conducted at the early stages of the copper deposits processing, such as flotation. The traditional copper flotation systems are insufficient and inadequate for separation and division of sulfide minerals containing arsenic (e.g. enargite $Cu_3AsS_4$ or tennantite $(Cu,Fe)_{12}As_4S_{13}$) from copper sulfides not containing arsenic, present in the ores. An aid to the conventional flotation methods are the methods proposed in recent years. One of the methods relates to the selective oxidation of sulfides, based on the electrochemical properties of the separated compounds [Fornasiero et al., 2001]. Another method of selective flotation utilizes the differences in the flotation pulp potentials [Guo and Yen, 2005]. Using the separation method based on the difference in the pulp's potentials, minerals containing arsenic, e.g. enargite $(Cu_3AsS_4)$, can be separated from copper sulfides not containing arsenic. As a result of these processes, two fractions of concentrates are produced: (i) with a low arsenic content, and (ii) with a high arsenic content. The former can be used in pyrometallurgical processes, whereas the latter fraction of concentrates, containing copper minerals contaminated with arsenic, still requires adequate treatment [Senior et al., 2006].

One of the ways that can help to solve the problem of removal of arsenic from copper minerals, is the application of biohydrometallurgical methods, using microorganisms to recover metals from minerals and deposits. The use of microorganisms for the extraction of copper or gold from their ores and concentrates, is a well-known process, and is often described in the literature [Xia, L. et al., 2010; Xia, L. et al., 2009; Olson et al., 2003; Rawlings and Johnson, 2007]. Most of the biohydrometallurgical processes are based on the processes of oxidation of minerals, and lead to (i) an increase in the accessibility to chemical solvents (biooxidation) or (ii) their direct dissolution (bioleaching) [Rawlings and Johnson, 2007]. Unfortunately, these methods are non-specific, because they are based on the oxidation of sulfur and/or iron from minerals, and are associated with the release of all the metals associated with this type of minerals. A further limitation of the traditional biohydrometallurgical methods is the use of acidophilic bacteria in leaching from neutral or slightly alkaline deposits, which is often inefficient, and sometimes even impossible, due to the need for the use of considerable amounts of sulfuric acid to acidify the deposits. In the literature microorganisms are described, mainly chemolithoautotrophic, sulfur oxidizing bacteria, belonging to the genus: *Thiobacillus, Halothiobacillus, Thiomonas*, and iron oxidizing bacteria, such as: *Galionella feruginea* or *Leptothrix ochracea, Thiothrix* and *Beggiatoa*, which can be used in bioleaching processes at neutral pH, but are very difficult to cultivate and are still poorly understood. Furthermore, bioleaching with the use of these microorganisms is time-consuming and these processes are carried out as long as several months [Sklodowska and Madakowska, 2007]. A confirmation of the lack of suitable microorganisms, capable of recovering metals under neutral or slightly alkaline conditions is the current situation in the mining market. Currently, there are no known and commercially available bitechnological methods of removing precious metals, occurring in the form of sulphides, under the conditions of neutral or slightly alkaline deposits.

An alternative to the oxidation processes are selective bioreduction processes, in which the selected elements, associated with the metabolic activity of microorganisms, are released. Although there are several examples of application of the bioreduction processes, methods for removing arsenic from copper minerals using microbial reduction are unknown. Many strains of bacteria that dissimilatory reduce arsenates have been identified, but the use of most of them is limited to the transformation of soluble arsenic compounds [Newman et al., 1998] or secondary arsenic minerals, resulting from iron compounds [Zobrist et al, 2000]. Strains capable of removing arsenic from copper concentrates and flotation tailings have also been described [Mantur et al., 2011], but the dissimilatory arsenate reduction process, carried out by the aforementioned strains, is not fully balanced and part of the arsenic may be removed out of the cells in the form of volatile, toxic arsenic compounds (unpublished data). Apart from that, the strains described by Mantur et al., 2011, simultaneously release copper and arsenic from minerals, thus lowering the value of the obtained copper concentrate.

Citation or identification of any document in this application is not an admission that such document is available as prior art to the present invention.

SUMMARY OF THE INVENTION

In the tight of the described state of the art, the aim of the present invention is to overcome the indicated inconveniences and to provide a plasmid which may comprise genetic information ensuring the capability of dissimilatory arsenate reduction and selective removal of arsenic, particularity from copper deposits. The aim of the invention is to provide novel bacterial strains which may comprise such a plasmid, compositions which may comprise them and uses thereof, and the methods for the selective removal of arsenic using such strains. Furthermore, it is desirable for such microorganisms, possessing the capability of arsenate reduction, not to produce volatile, and, at the same time, toxic arsenic compounds. The *Shewanella* sp. O23S strain, that has been isolated from microbial mats from a gold mine in Zloty Stok, possesses such properties [Drewniak, 20091]. The *Shewanella* sp. O23S strain has been deposited on 24 Jul. 2012 in the IAFB Collection of Industrial Microorganisms Institute of Agricultural and Food Biotechnology in Warsaw, Poland under the deposit number KKP 2045p. This strain is capable of anaerobic growth using arsenates as the final electron acceptor and can mobilize arsenic from rocks from the gold mine in Zloty Stok [Drewniak et al., 2010]. It was unexpectedly found, that these properties are ensured by the plasmid pSheB, isolated from *Shewanella* sp. O23S, the sequence of which has been shown in SEQ ID NO: 1, particularly its region which may comprise the fragment from 63978 to 72599, which encodes, among others, dissimilatory arsenate reductase, determining these properties.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

The *Shewanella* sp. O23S strain has been deposited on 24 Jul. 2012 in the IAFB Collection of Industrial Microorganisms Institute of Agricultural and Food Biotechnology in Warsaw, Poland under the deposit number KKP 2045p.

The Deposits with IAFB Collection of industrial Microorganisms institute of Agricultural and Food Biotechnology in Warsaw, Poland, under deposit accession number KKP 2045p were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

For a better understanding of the invention, it has been illustrated in the examples of embodiments and in the accompanying figures, in which:

FIG. 7A-B. Shows a comparison of the capability of dissimilatory arsenate reduction by the *Shewanella* sp. O23S strain in minimal medium R1-R2, having a pH 8 (A) and pH 4 (B). In order to compare the abilities of the investigated strain to dissimilatory reduce arsenates under various pH conditions, anaerobic cultures in minimal R1-R2 medium containing 2.5 mM (187.5 ppm) sodium arsenate and 5 mM sodium lactate were carried out.

DETAILED DESCRIPTION OF THE INVENTION

Figure 1:
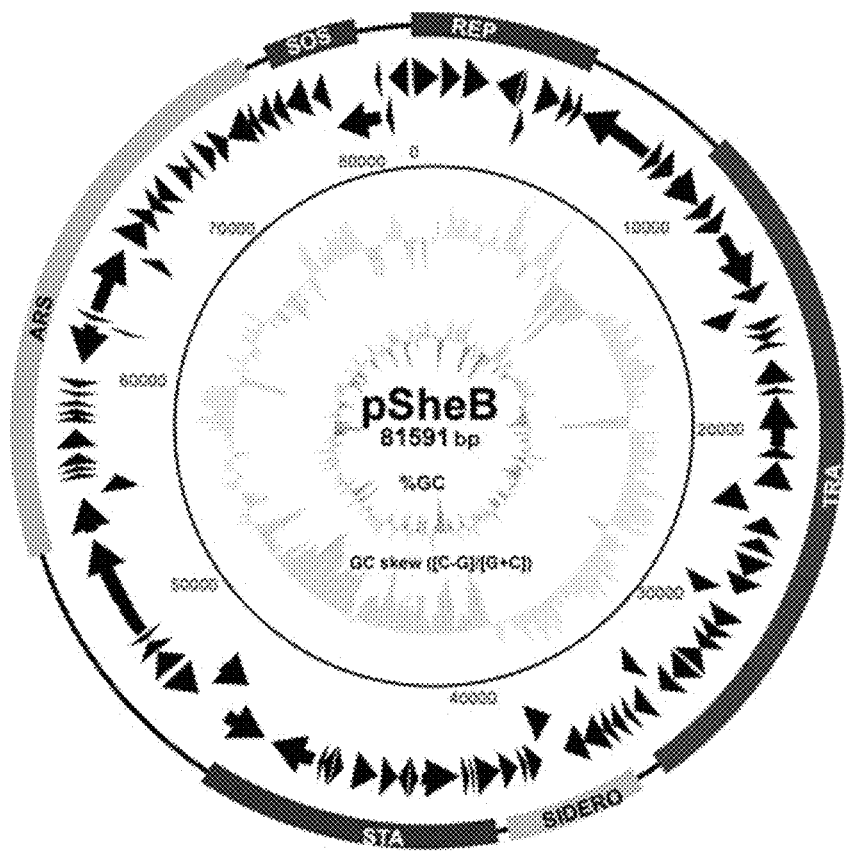
FIG. 1. Shows the genetic organization of the plasmid pSheB. In the diagram, different modules of the plasmid's structure and phenotypic regions have been described: REP/STA—replication-stabilization module, TA—toxin/antitoxin module, TRA—conjugation module, SIDERO—siderophore production module, STA—additional stabilization module, ARS—arsenic metabolism module, and SOS—SOS repair system module.

Bacterial strains which may comprise a plasmid including the fragment from 63978 to 72599 of SEQ ID NO: 1, plasmid pSheB or their functional derivatives, particularity the *Shewanella* sp. O23S strain (deposited as KKP 2045p), are capable of dissimilatory arsenate reduction and selective removal of arsenic, particularly from mineral resources, raw materials industry waste and from the soil, particularly preferable is that they are capable of dissimilatory arsenate reduction and selective removal of arsenic from copper deposits, preferably under neutral or slightly alkaline conditions. The bacterial strains which may comprise the plasmid which may comprise the fragment from 63978 to 72599 of SEQ ID NO: 1, pSheB or their functional derivatives, particularity the *Shewanella* sp. O23S strain (deposited as KKP 2045p) do not produce toxic, volatile arsenic compounds and stably persist in the environment.

The invention therefore relates to the isolated plasmid which may comprise the fragment of the nucleotide sequence from 63978 to 72599 of the plasmid pSheB, having the sequence shown in SEQ ID NO: 1 or its functional derivative.

The invention also relates to the plasmid pSheB shown in SEQ ID NO: 1 or its functional derivative.

The term "functional derivative of the plasmid" or "functional derivative of the sequence" may comprise plasmids/sequences having a nucleotide sequence coding for open reading frames, which encode products which may comprise an amino-acid or a nucleotide sequence identical or highly homologous to the sequences coded by the indicated sequences, wherein the coding sequences or other sequences of the plasmid/sequence have been modified e.g. by substitution, replacement, deletion or insertion, such that it does not essentially alter the activity of the products of these open reading frames, and enables the maintenance of functional features carried by such plasmid/sequence. The indicated sequence will therefore be the region which may comprise the fragment from 63978 to 72599 of SEQ ID NO: 1, equally preferably it will be the sequence of the plasmid pSheB shown in SEQ ID NO: 1. A highly homologous sequence means that the sequence is homologous, preferably identical in at least 70%, preferably 80%, more preferably 90%, most preferably, in at least 95%. The term "functional derivative of the plasmid" means, therefore, plasmids having a nucleotide sequence coding for open reading frames, encoding products which may comprise an amino-acid or a nucleotide sequence identical or highly homologous to the sequences coded by the fragment from 63978 to 72599 of SEQ ID NO: 1 and/or to the sequence of the plasmid pSheB shown in SEQ ID NO: 1, wherein the coding sequences or other plasmid sequences have been modified e.g. by substitution, replacement, deletion or insertion, such that it does not essentially alter the activity of the products of these open reading frames, and enables the maintenance of functional features carried by such a plasmid.

The essence of the present invention is thus based on an unexpected finding, that it is possible to use a strain containing the plasmid which may comprise the nucleotide fragment from 63978 to 72599 of SEQ ID NO: 1, pSheB shown in SEQ ID NO: 1 or their functional derivatives, particularity the *Shewanella* sp. O23S strain, deposited as KKP 2045p, for the selective removal of arsenic from mineral resources, raw materials industry: waste and soils, preferably under neutral or slightly alkaline conditions. It was unexpectedly found, that the strain which may comprise the plasmid pSheB, shown in SEQ ID NO: 1, particularly the *Shewanella* sp. O23S strain, is: capable of (i) growth in mineral media containing bituminous black shales, flotation tailings, and post-mining soils containing arsenic, (ii) selective release of arsenic from copper minerals containing arsenic, (iii) tolerating the toxic effects of heavy metals released as a result of dissolution of minerals, is (iv) lacking the ability to produce volatile arsenic compounds, is (v) lacking the ability to mobilize copper from mineral resources. The present invention, therefore, also relates to the *Shewanella* sp. O23S strain, which may comprise the plasmid pSheB, deposited under the number KKP2045p in the IAFB Collection of Industrial Microorganisms Institute of Agricultural and Food Biotechnology in Warsaw.

The invention also relates to a composition which may comprise the isolated plasmid according to the invention and/or a bacterial strain according to the invention or a combination thereof.

The invention also relates to use of a bacterial strain according to the invention, a composition according to the invention, for the selective removal of arsenic from mineral resources, raw materials industry waste or the soil.

Particularly preferred is the use of the bacterial strain, *Shewanella* sp. O23S, which may comprise the natural plasmid pSheB, carrying: (i) all the genes necessary for dissimilatory arsenate reduction, (ii) arsenite and arsenate resistance genes, and (iii) genes coding for the replication-stabilization system for selective removal of arsenic from mineral resources, raw materials industry waste and post-mining soils. The complete sequence of the plasmid pSheB of *Shewanella* sp. O23S has been shown in SEQ ID NO: 1.

The presented solutions according to the invention enable the removal of arsenic from mineral resources, raw materials waste, and post-mining soils, preferably under neutral or slightly alkaline conditions, preferably at a pH in the range of about 6 to about 8, using a strain which may comprise the plasmid pSheB or its derivative, more preferably *Shewanella* sp. O23S, without the need for acidification of the "environment" and without the risk of releasing toxic, volatile arsenic compounds. By the invention, it is possible to selectively remove arsenic without the undesirable release of the target metals, e.g. copper or gold.

The invention therefore relates to the method for selective removal of arsenic from mineral resources, raw materials industry waste, or the soil, in which the dissimilatory arsenate reduction step is carried out using a bacterial strain according to the invention and/or a composition according to the invention. Preferably, the dissimilatory arsenate reduction step is carried out under neutral or slightly alkaline conditions. Preferably, the mineral resources are copper deposits.

The invention also relates to the method for selective removal of arsenic from various mineral resources, raw materials industry, or soils, in which the removal of arsenic is carried out by dissimilatory arsenate reduction, using a bacterial strain according tote invention, preferably which may comprise the plasmid pSheB having the sequence shown in SEQ ID NO: 1 or its functional derivative, more preferably the *Shewanella* sp. O23S strain, deposited as KKP2045p, which method may comprise the following steps:

a) preparation of the mineral resources, wastes or soils and mixing with an appropriate culture medium enabling the cultivation of the strain, b) addition of an inoculum of the strain and carrying out the culture under conditions enabling its growth and conduction of dissimilatory arsenate reduction.

It is preferable when step b) is followed by step c) of selective removal of arsenic, released from the solutions obtained is step b). Such removal of arsenic from the solutions (culture fluids), will preferably be carried out using the already developed methods, e.g. by flotation, preferably by selective precipitation of arsenites with sulfides, as a consequence of which a stable, water-insoluble compound, arsenic sulfide $As_2S_3$ is formed [Robins, 1985].

In the preferred method, step a) is carried out by: (i) shredding and fractionation of mineral resources, wastes and soils, preferably to the fraction of 125-250 µm (having the average particle size), due to the highest performance obtainable in this range of particle sizes. Equally preferred is (ii) the preparation of an appropriate culture medium R1-R2 with additives of suitable substrates, among which are: sodium lactate as the source of carbon and energy, yeast extract as an additional source of carbon and vitamins. Tuovinen's mineral salts (Tuovinen slats (Tuovinen and Kelly, 1974)) as the source of microelements. Furthermore, in the preferred method, the medium does not contain $NO_3^-$ and $Fe^{3+}$.

It is equally preferred if in step b) the culture is carried out under conditions of an appropriate, anaerobic atmosphere, which is obtained by conducting the culture with flushing of the medium with a mixture of gases $N_2:CO_2$, preferably in a ratio 4:1. The flushing of the medium with the mixture of gases $N_2:CO_2$, preferably in a ratio 4:1, can be equally preferred already in step a) of the method of dissimilatory arsenate reduction.

In the preferred method, in order to obtain the highest performance for the *Shewanella* sp. O23S strain, step b) is carried out at a temperature in the range from 15° C. to 30° C., preferably about 22° C. with shaking (160 rpm), for at least 21 days. It is preferred if the density of the culture at the beginning of the process is at least about $10^6$ cells/ml. In the preferred method, the inoculum of the *Shewanella* sp. O23S strain is flushed several times with saline solution or is passaged several times to R1-R2 medium, enriched with sodium arsenate.

Publications cited in the description, and the references given therein, are in their entirety incorporated herein as references.

The following examples are presented merely to illustrate the invention and to clarify its various aspects, but are not intended to be limitative, and should not be equated with all its scope, which is defined in the appended claims.

In the following examples, unless it was otherwise indicated, standard materials and methods described in Sambrook et al., 2001. Molecular cloning: A laboratory manual. Cold Spring Harbor Laboratory Press, New York. were used, or the manufacturers' instructions for specific materials and methods were followed.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Characteristics of the Plasmid pSheB and Determination of its Complete Sequence

Plasmid pSheB, of the size of 81 kbp, was isolated from the *Shewanella* sp. O23S strain. In order to sequence the plasmid, plasmid pSheB was isolated from 200 ml of overnight culture of *Shewanella* sp. O23S by alkaline lysis method. Plasmid pSheB was sequenced by pyrosequencing method, using "shotgun" strategy on the GS FlX Titanium (454) sequencer (in the Oligo Pl. centre). For the construction of the DNA library, approx. 5 µg of pSheB DNA was used and reagent kits provided by the manufacturer were applied ((GS FLX Titanium Library Preparation Kit, Roche). The constructed library was sequenced and assembled using the software from the Newbler de novo assembler package (Roche). The obtained sequences were then assembled into contigs using Seqman software from Lasergene package (DNAStar). Annotation of the plasmid (identification of the open reading frames and determination of their potential functions) were performed using Artemis program and BLAST programs (from the NCBI database). The complete sequence of the plasmid has been shown in the SEQ ID NO: 1. Sequencing of the plasmid pSheB showed that it is a DNA particle of the size 81 591 bp and the GC-content of 44.04%. It comprises 87 open reading frames (ORF), which constitute 89.6% of the sequence of the plasmid. Table 1, below, features a detailed description of the identified ORFs within SEQ ID NO: 1.

TABLE 1

Determination of the potential coding sequences of the plasmid pSheB in reference to SEQ ID NO: 1.

| | Coding | | | The greatest similarity (BLASTP program) | | |
|---|---|---|---|---|---|---|
| ORF # | sequence (start-stop codon)* | Protein size (aa) | Predicted protein function | Identity (%) | Organism | GenBank number |
| 1 | 1-813 | 270 | Deoxyrybonuclease I (EndA) | 97 (233/240) | *Shewanella baltica* OS 195 (pS19501) | YP_001556993 |
| 2 | 826-1061 | 77 | Hypothetical protein | 100 (77/77) | *Shewanella baltica* BA175 (pSBAL17501) | YP_006018602 |
| 3 | 1454-3328 | 624 | ParB like nuclease | 99 (618/624) | *Shewanella baltica* BA175 (pSBAL17501) | AEG 13584 |
| 4 | 3453-3908 | 151 | Hypothetical protein | 99 (149/151) | *Shewanella baltica* OS195 (pS19501) | YP_001556996 |
| 5 | 4113-4397 | 94 | Hypothetical protein | 97 (91/94) | *Shewanella baltica* BA175 (pSBAL17501) | YP_006018598 |
| 6 | 4428-4649 | 73 | Hypothetical protein | 97 (71/73) | *Shewanella baltica* OS185 (pS18501) | YP_001355438 |
| 7 | 5014-5358 | 114 | Hypothetical protein | 100 (114/114) | *Shewanella baltica* OS195 (pS19502) | YP_001557025 |
| 8 | 5321-5944 | 207 | Hypothetical protein | 99 (204/207) | *Shewanella baltica* BA175 (pSBAL17501) | YP_006018595 |
| 9 | 5946-6347 | 133 | Hypothetical protein | 99 (132/133) | *Shewanella baltica* OS185 (pS18501) | YP_001355440 |
| 10 | 6545-6790 | 81 | Toxin protein (HicA) | 100 (81/81) | *Shewanella baltica* OS195 (pS19501) | YP_001557001 |
| 11 | 6790-7125 | 111 | Antitoxin protein (HicB) | 100 (111/111) | *Shewanella baltica* OS195 (pS19501) | YP_001557002 |
| 12 | 7423-7767 | 114 | Hypothetical protein | 98 (112/114) | *Shewanella baltica* OS195 (pS19502) | YP_001557025 |
| 13 | 7730-9058 | 442 | Hypothetical protein | 98 (4432/442) | *Shewanella baltica* OS625 | EHC04198 |
| 14 | 9656-9967 | 103 | Hypothetical protein | 99 (102/103) | *Shewanella baltica* OS625 | EHC04199 |
| 15 | 10260-10445c | 61 | Hypothetical protein | 34 (13/38) | *Scheffersomyces stipitis* CBS 6054 | XP_001384086 |
| 16 | 10524-10883 | 119 | Hypothetical protein | 100 (119/119) | *Shewanella baltica* OS185 (pS18501) | YP_001355446 |
| 17 | 10904-16857c | 1979 | Conjugative transfer relaxase (TraI) | 99 (1945/1969) | *Shewanella baltica* OS195 (pS19502) | YP_001557030 |
| 18 | 17109-19235c | 708 | Type IV conjugative transfer system coupling (TraD) | 98 (694/708) | *Shewanella baltica* OS223 (pS22302) | YP_002360331 |
| 19 | 19908-22721c | 937 | Sex pilus assembly and mating pair (TraG) | 95 (892/937) | *Shewanella baltica* OS223 (pS22302) | YP_002364250 |
| 20 | 22724-24112c | 462 | Type IV conjugative transfer system protein (TraH) | 99 (460/462) | *Shewanella baltica* OS625 | EHC04207 |
| 21 | 24296-24736c | 146 | Type-F conjugative transfer system pilin assembly thiol-disulfide isomerase (TrbB) | 97 (141/146) | *Shewanella baltica* OS195 (pS19501) | YP_001556945 |
| 22 | 24750-25622c | 290 | Type-F conjugative transfer system pilin assembly protein (TraF) | 99 (287/289) | *Shewanella baltica* OS 185 (pS18501) | YP_001355454 |
| 23 | 25622-27433c | 603 | Conjugal transfer mating pair stabilization protein (TraN) | 87 (530/607) | *Shewanella baltica* OS223 (pS22302) | YP_002364256 |
| 24 | 27430-28170c | 246 | Type-F conjugative transfer system pilin assembly protein (TrbC) | 100 (246/246) | *Shewanella baltica* OS195 (pS19501) | YP_001556948 |
| 25 | 28193-29200c | 335 | Sex pilus assembly and synthesis protein (TraU) | 99 (332/335) | *Shewanella baltica* BA175 (pSBAL17501) | YP_006018570 |
| 26 | 29187-29891c | 234 | Type-F conjugative transfer system protein (TraW) | 99 (232/234) | *Shewanella baltica* OS625 | EHC04215 |
| 27 | 29888-30259c | 123 | Conjugal transfer protein (TrbI) | 98 (120/123) | *Shewanella baltica* OS223 (pS22302) | YP_002360319 |
| 28 | 30261-32849c | 862 | Type-IV secretion system protein (TraC) | 99 (856/862) | *Shewanella baltica* BA175 (pSBAL17502) | YP_006022865 |
| 29 | 32853-33296c | 147 | Type IV conjugative transfer system protein (TraV) | 100 (147/147) | *Shewanella baltica* OS195 (pS19501) | YP_001556953 |
| 30 | 33329-34855c | 508 | Sex pilus assembly and synthesis protein (TraB) | 98 (500/508) | *Shewanella baltica* OS678 | YP_005280401 |
| 31 | 34852-35667c | 271 | Type-F conjugative transfer system secretin (TraK) | 95 (258/271) | *Shewanella baltica* OS223 (pS22302) | YP_002364264 |

TABLE 1-continued

Determination of the potential coding sequences of the plasmid pSheB in reference to SEQ ID NO: 1.

| ORF # | Coding sequence (start-stop codon)* | Protein size (aa) | Predicted protein function | The greatest similarity (BLASTP program) | | |
|---|---|---|---|---|---|---|
| | | | | Identity (%) | Organism | GenBank number |
| 32 | 35807-36232c | 141 | Type IV conjugative transfer system protein (TraE) | 97 (118/122) | *Shewanella baltica* OS223 (pS22302) | YP_002364265 |
| 33 | 36273-36575c | 100 | Type IV conjugative transfer system protein (TraL) | 94 (94/100) | *Shewanella baltica* OS195 (pS19501) | YP_001556957 |
| 34 | 36579-36953c | 124 | Type IV conjugative transfer system pilin (TraA) | 87 (111128) | *Shewanella baltica* BA175 (pSBAL17502) | YP_006022871 |
| 35 | 37017-37205c | 62 | Hypothetical protein | 100 (62/62) | *Shewanella baltica* OS223 (pS22301) | YP_002360254 |
| 36 | 37307-37564c | 85 | Hypothetical protein with helix-turn-helix domain | 100 (85/85) | *Shewanella baltica* OS195 (pS19501) | YP_001556959 |
| 37 | 37684-37866 | 60 | Hypothetical protein | 100 (60/60) | *Shewanella baltica* OS195 (pS19501) | YP_001556960 |
| 38 | 38139-38321 | 60 | Hypothetical protein | 32 (18/56) | *Staphylococcus aureus* subsp. *aureus* USA300_FPR3757 | YP_494132 |
| 39 | 38308-39240 | 310 | Hypothetical protein | 97 (301/310) | *Shewanella baltica* OS195 (pS19503) | YP_001557103 |
| 40 | 39774-40076c | 100 | Pyridoxamine kinase family protein | 27 (28/104) | *Megasphaera micronuciformis* F0359 | ZP_07757187 |
| 41 | 40161-40442c | 93 | Hypothetical protein | 86 (75/87) | *Shewanella oneidensis* MR-1 (megaplasmid) | NP_720395 |
| 42 | 40448-40975 | 175 | N-Acyltransferase superfamily protein | 91 (160/175) | *Shewanella oneidensis* MR-1 (megaplasmid) | NP_720396 |
| 43 | 41417-41647c | 76 | Hypothetical protein | 100 (74/74) | *Shewanella baltica* OS223 (pS22301) | YP_002360250 |
| 44 | 41822-43012 | 396 | Plasmid partition protein (PatA) | 99 (392/396) | *Shewanella baltica* BA175 (pSBAL17501) | AEG13539 |
| 45 | 43012-44169 | 385 | Plasmid partition protein (ParB) | 97 (347/356) | *Shewanella baltica* BA175 (pSBAL17501) | YP_006018554 |
| 46 | 44256-44402 | 48 | Hypothetical protein | | | |
| 47 | 44438-48298 | 1268 | NTPase with transmembrane helices | 25 (321/1284) | *Bacillus subtilis* subsp. *subtilis* str. 168 | NP_389778 |
| 48 | 48454-49113 | 219 | Hypothetical protein | 60 (131/218) | *Methylophaga thiooxydans* DMS010 | ZP_05102952 |
| 49 | 49234-49623 | 129 | Hypothetical protein | 39 (49/125) | *Methylovorus glucosetrophus* SIP3-4 | YP_003050141 |
| 50 | 49640-50545 | 301 | Hypothetical protein | 34 (102/300) | delta proteobacterium MLMS-1 | ZP_01290544 |
| 51 | 50655-51623 | 322 | Hypothetical protein | 66 (212/322) | *Pseudoalteramonas arctica* A 37-1-2 | ZP_10279906 |
| 52 | 51781-52386 | 201 | Hypothetical protein | 25 (44/176) | *Enterobacter cloacae* SCF1 | YP_003941396 |
| 53 | 52593-53222c | 209 | Resolvase domain-containing protein (TnpR) | 98 (204/209) | *Shewanella baltica* OS185 (pS18501) | YP_001355408 |
| 54 | 53345-53827 | 159 | Transposase(TnpA) | 72 (32/46) | *Vibrio furnissii* CIP 102972 | EEX38686 |
| 55 | 53836-54123 | 95 | Hypothetical protein | 83 (79/95) | *Marinomonas* sp. MWYL1 | ABR70068 |
| 56 | 54532-54840 | 102 | ArsR family transcriptional regulator | 94 (96/102) | *Shewanella* sp. ANA-3 | YP_869986 |
| 57 | 54901-55143 | 80 | Thioredoxin - redox-active disulfide protein 2 | 93 (74/80) | *Shewanella* sp. ANA-3 | YP_869985 |
| 58 | 55162-55695 | 177 | Hypothetical protein | 95 (169/177) | *Shewanella* sp. ANA-3 | YP_869984 |
| 59 | 55706-56386 | 226 | Cytochrome c biogenesis protein | 99 (225/226) | *Shewanella* sp. ANA-3 | YP_869983 |
| 60 | 56554-57555 | 333 | RND family efflux transporter MFP subunit | 93 (311/333) | *Shewanella* sp. ANA-3 | YP_869982 |
| 61 | 57552-60625 | 1023 | Acriflavin resistance protein (AcrB) | 98 (1002/1023) | *Shewanella* sp. ANA-3 | YP_869981 |
| 62 | 60743-61177c | 144 | Arsenate reductase (ArsC) | 94 (131/140) | *Shewanella* sp. ANA-3 | YP_869980 |
| 63 | 61265-62512c | 415 | Arsenical pump membrane protein (ArsB) | 98 (407/414) | *Shewanella* sp. W3-18-1 | YP_964320 |
| 64 | 62613-64385c | 590 | Arsenite-activated ATPase (ArsA) | 92 (543/590) | *Shewanella* sp. W3-18-1 | YP_964319 |
| 65 | 64420-64782c | 120 | Arsenical resistance operon transacting repressor (ArsD) | 85 (102/120) | *Shewanella* sp. W3-18-1 | YP_964318 |

TABLE 1-continued

Determination of the potential coding sequences of the plasmid pSheB in reference to SEQ ID NO: 1.

| ORF # | Coding sequence (start-stop codon)* | Protein size (aa) | Predicted protein function | The greatest similarity (BLASTP program) | | |
|---|---|---|---|---|---|---|
| | | | | Identity (%) | Organism | GenBank number |
| 66 | 65155-67719 | 854 | Respiratory arsenate reductase, Mo binding subunit (ArrA) | 96 (818/854) | *Shewanella* sp. ANA-3 | YP_869976 |
| 67 | 67731-68435 | 234 | Respiratory arsenate reductase, FeS subunit (ArrB) | 97 (228/234) | *Shewanella* sp. ANA-3 | YP_869975 |
| 68 | 68506-69936c | 476 | Glutathione synthase | 86 (409/476) | *Shewanella putrefaciens* CN-32 | YP_001182743 |
| 69 | 70092-71144c | 350 | Permease | 76 (271/358) | *Shewanella putrefaciens* CN-32 | YP_001185328 |
| 70 | 71369-71656 | 95 | ArsR family transcriptional regulator | 92 (87/95) | *Shewanella* sp. ANA-3 | YP_869972 |
| 71 | 71755-72171 | 138 | Transcriptional regulator - tyrosine phosphatase (ArsR) | 93 (127/138) | *Shewanella* sp. ANA-3 | YP_869971 |
| 72 | 72164-72511 | 115 | ArsR family transcriptional regulator | 97 (112/15) | *Shewanella* sp. ANA-3 | YP_869970 |
| 73 | 72590-73102 | 170 | Protein tyrosine phosphatase (ArsC2) | 84 (141/167) | *Shewanella* sp. ANA-3 | YP_869969 |
| 74 | 73195-74192 | 332 | Permease | 96 (318/332) | *Shewanella* sp. ANA-3 | YP_869968 |
| 75 | 74204-74440 | 78 | Redox-active disulfide protein 2 | 97 (76/78) | *Shewanella putrefaciens* CN-32 | YP_001185322 |
| 76 | 74448-74939 | 163 | Dual specificity protein phosphatase | 86 (140/163) | *Shewanella putrefaciens* CN-32 | YP_001185321 |
| 77 | 74996-76006 | 336 | Glyceraldehyde-3-phosphate dehydrogenase | 99 (332/336) | *Shewanella* sp. W3-18-1 | YP_964294 |
| 78 | 76012-77250 | 412 | Major facilitator superfamily protein | 99 (409/412) | *Shewanella putrefaciens* 200 | YP_006009170 |
| 79 | 77357-77656 | 99 | Hypothetical protein | 92 (91/99) | *Shewanella putrefaciens* CN-32 | YP_001185318 |
| 80 | 77964-78146 | 60 | Hypothetical protein | 32 (13/41) | *Streptococcus pneumoniae* | CAI34125 |
| 81 | 78249-78683 | 144 | Peptidase S24/S26A/S26B | 97 (139/144) | *Shewanella baltica* BA175 (pSBAL17501) | YP_006018610 |
| 82 | 78671-79924 | 417 | UMUC domain-containing protein DNA-repair protein | 93 (389/417) | *Shewanella baltica* BA175 (pSBAL17501) | YP_006018609 |
| 83 | 79975-80238 | 87 | Vitamin B12 dependent methionine synthase | 30 (24/81) | *Coprococcus comes* ATCC 27758 | ZP_03798710 |
| 84 | 80344-80994 | 216 | Hypothetical protein | 68 (150/219) | *Aeromonas hydrophila* | YP_002995563 |
| 85 | 81035-81253 | 72 | Hypothetical protein | 93 (67/72) | *Shewanella baltica* OS117 (pSBAL11701) | YP_006035206 |
| 86 | 81273-81591 | 106 | Hypothetical protein | 96 (102/106) | *Shewanella baltica* BA175 (pSBAL17501) | YP_006018603 |

*The numbers in the coding sequence correspond to the nucleotide numbers in SEQ ID NO: 1.

Example 2

Construction of the Plasmid-Less Strain and Functional Analysis of the Plasmid pSheB In order to show, that the plasmid pSheB and the gene module coding for potential proteins located within it, are involved in the resistance to arsenic and dissimilatory arsenates reduction, a plasmid-less derivative of the *Shewanella* sp. O23S strain was constructed and its functional analysis was carried out. As the stress factor stimulating the mechanisms of plasmid removal from the cells of the host, ethidium bromide (EtBr) solution at a final concentration of 5 μM was used.

Overnight culture of the wild-type *Shewanella* sp. O23S strain, carried out in LB medium supplemented with 5 mM sodium arsenate was passaged to LB medium with 5 μM EtBr. The optical density (OD) of the culture at the beginning of the experiment was OD=0.1, and the culture was carried out for 24 hours at 22° C. with shaking (160 rpm). After 24 hours of incubation, culture dilutions $10^{-4, -6, -8, -10}$ were prepared, respectively, and 100 μl of each of them were plated on LB medium solidified with agar. Subsequently, 96 colonies were randomly selected and passaged by replica plating to:

(i) solid LB medium, (ii) solid LB medium supplemented with sodium arsenate (50 mM), and (iii) liquid minimal R1-R2 medium (R1 salt: NaCl—1.17 g/l; KCl—0.3 g/l; NH$_4$Cl—0.15 g/l; MgCl$_2$×6H$_2$O—0.41 g/l; CaCl$_2$×2H$_2$O—0.05 g/l and R2 salt (KH$_2$PO$_4$—0.17 g/l; NaHCO$_3$—2.0 g/l; Na$_2$SO$_4$×10 H$_2$O—0.07 g/l mixed in a ratio 1:1), enriched with sodium lactate at a final concentration of 5 mM, salts according to Tuovinen (2 ml/l) (pH 6.0; with the composition: Na$_2$EDTA 50 g/l; ZnSO$_4$.7H$_2$O 11 g/l; MnCl$_2$.7H$_2$O 5.5 g/l; FeSO$_4$.7H$_2$O 2.5 g/l; (NH$_4$)$_6$Mo$_7$O$_{24}$.4H$_2$O 5 g/l; CuSO$_4$.5H$_2$O 2 g/l; CoCl$_2$.6H$_2$O 0.5 g/l; NaOH 11 g/l) (Tuovinen et al., 1973), yeast extract at a final concentration of 0.004% and 2.5 mM sodium arsenate.

The cultures in solid media were incubated for 72 hours, whereas the cultures in the liquid medium were carried out in 200 µl in 96-well titration plates in Anaerocult® (Merck) containers, which provide anaerobic conditions for 168 hours.

The cultures carried out in the liquid medium were aimed to determine the abilities of the selected strains to dissimilatory reduce arsenates. After 5 days of incubation under anaerobic conditions, 100 µl of 0.1 M solution of silver nitrate were added to the cultures. The result of the reaction between $AgNO_3$ and As (III) or As (V) is the formation of a coloured precipitate. A brown precipitate indicates the presence of $Ag_3AsO_4$ (silver orthoarsenate), while a yellow precipitate indicates the presence of $Ag_3AsO_3$ (silver arsenite). In case of testing for the ability to reduce arsenates, the presence of a yellow precipitate indicates that As(V) was reduced to As(III).

The cultures carried out in solid LB medium enriched with sodium arsenate were aimed to determine the resistance to As(V). In turn, the cultures carried out in solid LB medium (not enriched with additional substances) were aimed to secure the potential mutants (positive control). All the strains, which have grown in LB medium, and were not capable of growth in LB medium enriched with As(V) and in minimal R1-R2 medium containing arsenate (the final electron acceptor) and lactate (electron donor), have been designated as potential mutants, deprived of the plasmid pSheB.

In order to verify the selected consortia, the plasmid profile of the wild-type strain (*Shewanella* sp. O23S) and the potential plasmid-less mutants was checked. The plasmid DNA was isolated by alkaline lysis method, and electrophoretic analysis (0.8% agarose gel) was conducted. The comparison of the plasmid patterns of the selected strains allowed for the identification of the plasmid-less mutants. An additional confirmation of the absence of the plasmid pSheB in the cells of the constructed mutants was PCR analysis. PCR reaction was carried out in the genomes of the potential mutants, using the following primers:

```
endA-L   GCTGTTGCTTCCAATACGAC    (SEQ ID NO: 2)
and endA-R   GGCGCTGCGACTTACTCATC    (SEQ ID NO: 3)
```

Primer endA-L respectively corresponds to the position of the nucleotide 127, while endA-R—position 679 of the plasmid pSheB in reference to SEQ ID NO: 1. The strains (potential mutants) which gave a negative result in the PCR reaction, using the primers described above, were selected for further analysis.

Figure 2:
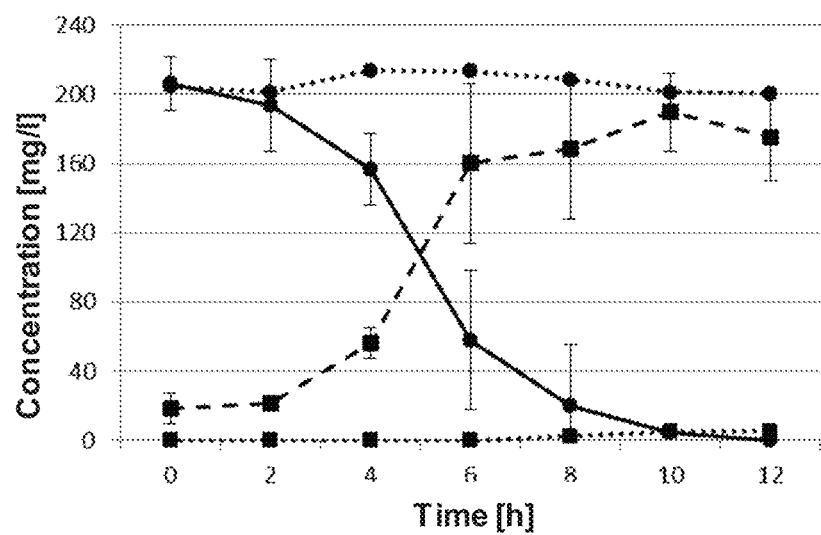
FIG. 2. Shows a comparison of the capability of dissimilatory arsenate reduction by a wild-type strain (wt) *Shewanella* sp. O23S deposited as KKP2045p (harbouring the plasmid pSheB) and its derivative, deprived of the plasmid pSheB. In order to compare the abilities of the investigated strains to reduce arsenates to arsenites, anaerobic cultures were carried out in minimal R1-R2 medium containing 2.5 mM (187.5 ppm) of sodium arsenate. As(V) and As(III) content in culture fluids collected from the cultures every 24 hours is shown on the graph. ●—indicates the concentration of As(V), ■—indicates the concentration of As(III), a solid line indicates the kinetics of As(V) reduction, carried out by the wild-type strain, while a dashed line—by the derivative, deprived of the plasmid pSheB.

The next step of the verification of the strains not-possessing the plasmid pSheB was their functional analysis. It was checked again whether the selected strains are capable of dissimilatory arsenate reduction. For this purpose, tests were carried out in minimal R1-R2 medium enriched with sodium arsenate and sodium lactate, and applying the test with 0.1 M solution of silver nitrate. The strains, which were not capable of reduction, were susceptible to As(V) and As(III), and did not possess the plasmid pSheB, turned out to be a proof that the plasmid pSheB determines the capability of arsenate respiration and resistance to arsenic. FIG. 2. shows a graph illustrating the kinetics of arsenate reduction of the wild-type strain and the mutant deprived of the plasmid pSheB. The strain deprived of the plasmid was not capable of growth in minimal medium supplemented with 2.5 mM sodium arsenate, thus it was unable to reduce As(V) to As(III). In this way it was shown that the genetic information contained in the plasmid pSheB (SEQ ID NO: 1) determines the acquisition of the capability of growth under anaerobic conditions, using arsenates as the final electron acceptor, thus the capability of dissimilatory arsenate reduction.

Example 3

Construction of the Vector Carrying a Gene Module Coding for the Proteins Involved in Dissimilatory Arsenate Reduction In order to demonstrate, which genes located on the plasmid pSheB encode proteins responsible for dissimilatory arsenate reduction, the arr module, which may comprise i.a. genes for dissimilatory arsenate reductase arrAB, was cloned into the vector pBBR1-MCS2 (Km$^r$), in the *Escherichia coli* TOP10 strain, and its functionality was tested.

In order to clone the arr module, amplification of a DNA fragment of the size 8634 bp (which may comprise the region from position 63978 to 72599 in the genome of pSheB) was performed on a DNA template of the plasmid pSheB, isolated by alkaline lysis. For PCR reaction, the following oligonucleotides were used as primers:

She_Mph1103F: GAAATCTTGCAGTAGCG<u>ATGCATC</u> (SEQ ID NO: 4) [position in the genome of the plasmid pSheB: 63978-64001; the underlined sequence is the restriction site recognized by the enzyme Mph11031 (NsiI)], and She_XmaJR: GTTGTT<u>CCTAGG</u>CTGGTGCCATATCAACCTCTAG (SEQ ID NO: 5) (position in the genome of the plasmid pSheB: 72578-72599; the sequence written in italic is an added sequence; the underlined site is recognized by the restriction enzyme XmaJI). For the amplification, Phusion® High-Fidelity DNA Polymerase (Thermo Scientific) was used.

The obtained PCR product (8634bp) was cloned into a plasmid vector: pBBR1MCS-2 (Km$^r$) [Kovach et al., 1995] digested (linearized) with SmaI. The ligation mixture of the PCR product and the vector pBBR1MCS2 digested with the enzyme SmaI was introduced, by means of chemical transformation, using the calcium-rubidium method according to Kushner (1978), into the cells of *Escherichia coli* Top10 strain [mcrA Δ(mrr-hsdRMS-mcrBC) φ80lacZΔM15 ΔlacX74 recA1 araD139 Δ(ara-leu)7697 galU galK rpsL endA1 nupG]. Complete LB medium with kanamycin (30 µg/ml), IPTG (0.5 µg), and X-gal (40 µg/ml) was used as the selection medium.

From the pool of the obtained transformants (white colonies resistant to kanamycin) strains that were harbouring a plasmid of the appropriate size: 13778 bp (pBBR1MCS2-5144bp+arr module–8634 bp). The presence of the constructed plasmid was confirmed by restriction analysis (digestion with the enzymes XmaJI and Mph11031), electrophoretic analysis and sequencing. The *Escherichia coli* MR1 strain (derivative of the *E. coli* TOP10 strain) harbouring the plasmid pARR1A (derivative of pBBR1MCS2 with cloned arr module), was selected for further analysis.

In order to verify the functionality of the constructed plasmid pARR1A, phenotypic analysis of the *E. coli* MR1 strain was carried out in minimal R1-R2 medium enriched with 2 mM sodium arsenate and 5 mM sodium lactate and supplemented with 0.004% yeast extract. The culture was carried out for 120 h under anaerobic conditions (in $CO_2$:$N_2$ atmosphere) at 37° C. After five days of culturing, the test with 0.1 M solution of silver nitrate was carried out, which showed that the investigated strain has reduced arsenates to arsenites. A confirmation of the reduction of arsenates to arsenites by the *E. coli* MR1 (pARR1A) strain, was the qualitative analysis of arsenic speciation by HPLC. The conducted analysis showed that after 120 h of incubation of the *E. coli* MR1 strain, arsenites were identified in the medium. In the control reaction with the *E. coli* TOP10 strain (without the plasmid), reduction of As(V) to As(III) was not observed.

The obtained results showed that the introduction of the genes of the arr module, originating from the genome of the plasmid pSheB, on the vector pBBR1MCS into the *E. coli* TOP10 strain, leads to the acquisition of the capability of dissimilatory arsenate reduction. The module introduced to *E. coli* TOP10 corresponded to the fragment of the nucleotide sequence from 63978 to 72599 of the plasmid pSheB, having the sequence shown in SEQ ID NR: 1. In this way it was demonstrated that this is the fragment of the plasmid responsible for the capability of dissimilatory arsenate reduction. It was also demonstrated, that a bacterium other than that, from which the plasmid pSheB originates, that is another species of bacteria or a bacterial strain, into which the fragment of the sequence which may comprise the fragment of the nucleotide sequence from 63978 to 72599 of the plasmid pSheB, having the sequence shown in SEQ ID NO: 1 has been introduced, acquires the ability to dissimilatory reduce arsenates.

Example 4

Removal of Arsenic from Copper Minerals Using the *Shewanella* sp. O23S Strain

In order to demonstrate that a strain which may comprise the plasmid pSheB (SEQ ID NO: 1), for example the *Shewanella* sp. O23S strain, harbouring the plasmid pSheB, can be used in biometallurgy, in the processes of selective removal of arsenic from mineral resources, an experiment was carried out, using two types of minerals: copper-bearing bituminous shale of the "Kupferschiefer" type and flotation tailings from the first series, obtained from the Mining Plant "Lubin" (KGHM, Poland). The average arsenic content in the copper-bearing bituminous shale designated as "Shales" was 1000-3000 mg/kg of the shale, whereas the arsenic content in the flotation tailings designated as "Middlings" was 250-350 mg/kg of the tailings. Apart from arsenic, both types of minerals contain Cu in the range of 35000-110000 mg/kg of dry mass, and other precious metals, e.g. Co—500-2500 mg/kg, Zn—15-2800 mg/kg, Ni—250-500 mg/kg.

The experiment of arsenic removal from the mineral resources described above was conducted in R1-R2 medium enriched with 5 mM sodium lactate as the source of carbon and energy, Tuovinen salts (2 ml/l) and yeast extract at a final concentration of 0.004%. The mineral substrate (shales or flotation tailings) having the fraction size of 125-250 mm, was added to a final concentration of 10%. The cultures were carried out in 100-ml bottles under anaerobic conditions, in the atmosphere of the mixture of gases $N_2:CO_2$ (4:1) for 21 days at 22° C. with shaking (160 rpm). In order to obtain an inoculum of the *Shewanella* sp. O23S strain, overnight cultures were started in liquid complete LB medium. The overnight culture of the O23S strain was centrifuged several times and flushed with saline solution, and then passaged to an appropriate medium, to obtain a density of approximately $10^6$ cells/ml. Sterile medium supplemented with an appropriate substrate, not inoculated with bacteria, was used as the control.

At the beginning of the experiment, and every 7 days, samples for the determination of copper and arsenic content were collected, which was performed using atomic absorption spectroscopy—flame technique; (AA Solaar M6 Spectrometer, TJA Solutions, UK).

Figure 3:
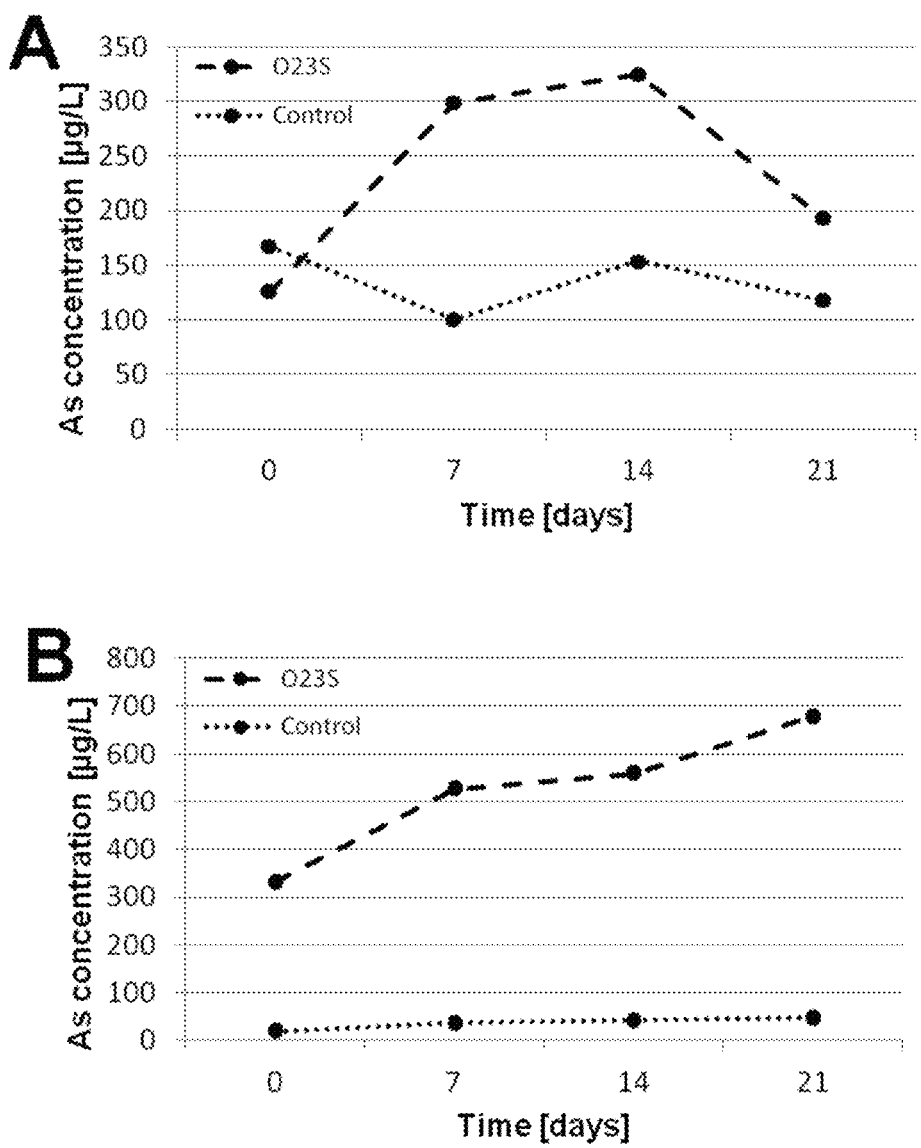
FIG. 3A-B. Shows a graph illustrating the efficiency of the process of arsenic removal from mineral resources by the *Shewanella* sp. O23S strain for A) flotation tailings, B) bituminous shales. Sterile R1-R2 media, enriched with the respective mineral resources: (A) flotation tailings ("middlings") and (B) bituminous shales ("shales"), were used as the control samples.
Figure 4:
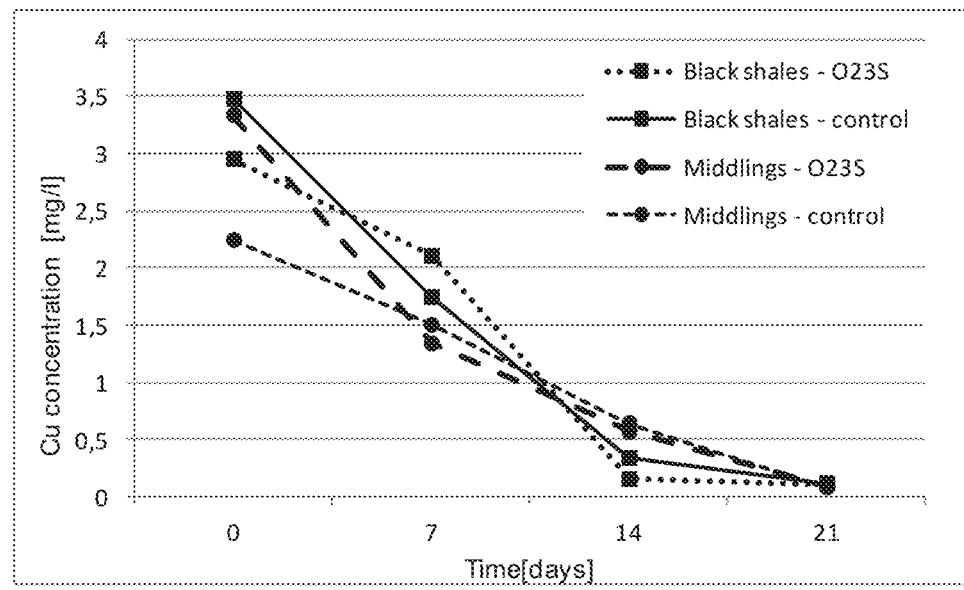
FIG. 4. Shows a graph illustrating the efficiency of the process of copper removal from mineral resources by the *Shewanella* sp. O23S strain for flotation tailings ("middlings") and bituminous shales ("shales"). Sterile R1-R2 media, enriched with the respective mineral resources: flotation tailings ("middlings") and bituminous shales ("shales"), were used as the control samples.
Figure 5:
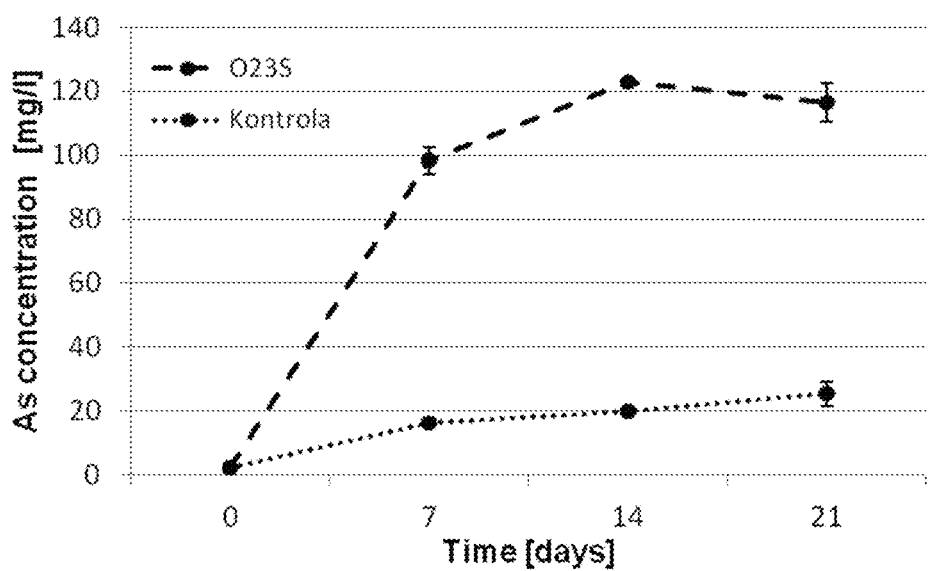
FIG. 5. Shows a graph illustrating the efficiency of the process of arsenic removal from the soil contaminated with arsenic by the *Shewanella* sp. O23S strain. In order to confirm the ability of the investigated strain to remove arsenic from the soil, a soil sample originating from the Zloty Potok area was used, and an anaerobic culture in minimal R1-R2 medium was carried out, Arsenic content in culture fluids collected from the cultures every 24 hours is shown on the graph. Sterile R1-R2 media with the addition of the soil were used as the controls.

The conducted analyses showed, that the highest concentration of arsenic in culture fluids in medium enriched with flotation tailings was noted after 14 days of incubation (324.75 µg/l) (FIG. 3A). In a further week of incubation, the concentration of arsenic has dropped (192.75 mg/l), which may be associated with precipitation of arsenic in the form of the secondary minerals, in the control samples, concentration of arsenic was at much lower level (it did not exceed 153.75 µg/l), and reflected the chemical processes of leaching. In turn, in culture fluids, in medium enriched with bituminous shales, the highest concentration of arsenic was noted after 21 days of the experiment (678.25 µg/l). At the same time, in the control sample, an approx. 14-times lower concentration of arsenic (47.25 µg/l) was noted. These results indicate that the *Shewanella* sp. O23S strain with the plasmid pSheB (SEQ ID NO: 1) is capable of releasing arsenic from copper minerals. It was therefore extremely important to verify how the release of arsenic would influence copper mobilization. In case of copper content analysis, no significant differences were observed between the Cu content in culture fluids and the control sample. At the beginning of the experiment it was noted that part of the copper was washed out of the minerals as a result of the chemical (stimulated by the medium components) dissolution of copper minerals (FIG. 4). The release of copper occurred with an extremely low efficiency, and Cu concentrations in culture fluids and the control samples did not exceed 3.5 ppm. Furthermore, with the passing of time, the concentration of copper was decreasing (after 21 days of cultivation, the concentration of Cu was below 0.5 ppm (FIG. 4.), which was probably associated with the chemical precipitation of copper.

The conducted experiment allowed to demonstrate that the strain which may comprise the plasmid pSheB (SEQ ID NO: 1), i.e. the *Shewanella* sp. O23S strain, deposited as KKP2045p, removes arsenic from copper-bearing bituminous shales, as well as from flotation tailings in a specific way, without simultaneous mobilization of copper from copper deposits.

Example 5

Mobilization of Arsenic from the Soils Contaminated with Arsenic Using the *Shewanella* sp. O23S Strain In order to demonstrate that a strain harbouring the plasmid pSheB, having the SEQ ID NO: 1 or its functional derivative, such as *Shewanella* sp. O23S, harbouring the plasmid pSheB, can be used in bioremediation, in the processes of selective arsenic removal from the soils contaminated with arsenic, an experiment using the soil originating from the vicinity of a gold mine in Zloty Stok was conducted. The average arsenic content in the soil was 17955.7 mg/kg of soil.

The experiment of arsenic removal from the soil was conducted in R1-R2 medium enriched with 5 mM sodium lactate (carbon and energy source), Tuovinen* salts (2 ml) and yeast extract at a final concentration of 0.004%. The fragmented sample (having the fraction size of <3 mm) was added to a final concentration of 10%. The cultures were carried out in 100-ml bottles under anaerobic conditions in the atmosphere of the mixture of gases $N_2:CO_2$ (4:1) for 21 days at 22° C. with shaking (160 rpm). In order to obtain an inoculum of the *Shewanella* sp. O23S strain, overnight cultures were started in liquid complete LB medium. The overnight culture of the O23S strain was centrifuged several times and flushed with saline solution, and then passaged to an appropriate medium to obtain a density of approximately $10^6$ cells/ml. Sterile medium with the addition of the soil, not inoculated with bacteria, was used as the control.

At the beginning of the experiment, and every 7 days, samples were collected for: (i) determination of the arsenic content (determination by atomic absorption spectroscopy—flame technique) in culture fluids (ii) monitoring the growth of bacteria, by the analysis of the number of colony forming units (cfu) (plating on solid LB medium enriched with 5 mM sodium arsenate). The conducted analyses showed, that the highest concentration of arsenic in culture fluids was noted after 14 days of incubation (166.53 mg/l), whereas after a further 7 days of incubation, concentration of arsenic has decreased slightly (123.03 mg/l), which may be associated with the precipitation of arsenic in the form of secondary minerals. In the control samples, concentration of arsenic was at much lower level (it did not exceed 25 mg/l), and reflected the chemical processes of leaching. It was demonstrated that a strain which may comprise the plasmid pSheB, having the SEQ IN NO:1, i.e. the *Shewanella* sp. O23S strain, removes arsenic from the soils contaminated with this element and can be used in bioremediation, e.g. in the recultivation of arsenic contaminated soils or the removal of arsenic from other contaminated environments.

Example 6

Analysis of Arsenic Accumulation by the *Shewanella* sp. O23S Strain

The growth experiment and the dissimilatory arsenate reduction performance analysis, carried out in R1-R2 medium (FIG. 2) revealed that a strain harbouring the plasmid pSheB, having the SEQ ID NO:1 or its functional derivative, such as *Shewanella* sp. O23S, completely reduces arsenates to arsenites, which are completely removed out of the cell. In order to confirm that the *Shewanella* sp. O23S strain is not capable of accumulating arsenic inside the cells, an additional 24-hour growth experiment was carried out in liquid LB medium. The LB medium was enriched with a solution of sodium arsenites ($NaAsO_2$) or sodium arsenates ($Na_2HAsO_4$) having a final concentration of 2 mM. The cultures were carried out in a volume of 50 ml under aerobic conditions at 22° C. with shaking (160 rpm). Sterile LB medium with solutions of the investigated salts was used as the control. After 24 hours of incubation, cultures were centrifuged and the arsenic content in culture fluids and biomass (bacterial pellet) was determined by atomic absorption spectroscopy (AA Solaar M6 Spectrometer, TJA Solutions, UK).

The conducted analyses did not confirm the growth experiments in R1-R2 medium and revealed that arsenic compounds may be partially accumulated inside the cells of the *Shewanella* sp. O23S strain. The efficiency of this process, however is very low, less than 3% for As(III) compounds, and less than 8% for As(V) compounds. The obtain results are shown in Table 2.

TABLE 2

Comparison of the ability to accumulate arsenic by the *Shewanella* sp. O23S strain, cultured in minimal medium (R1-R2) and complete medium (LB).

| | LB medium | | R1-R2 medium | |
|---|---|---|---|---|
| | As(III) | As(V) | As(III) | As(V) |
| Arsenic content in culture fluids [ppm] | 144.8119 | 163.8377 | 204.8073 | N/D |
| Arsenic content in the biomass [ppm] | 5.809583 | 13.97905 | 4.1078 | N/D |
| Accumulation efficiency [%] | 3.857076 | 7.861492 | 1.9636 | N/D |

N/D-not determined

Example 7

Analysis of the Production of Volatile Arsenic Compounds by the *Shewanella* sp. O23S Strain In order to verify whether the *Shewanella* sp. O23S strain which may comprise the plasmid pSheB is capable of producing volatile arsenic compounds, an anaerobic (in $N_2:CO_2$ atmosphere; 4:1) culture in minimal R1-R2 medium, enriched with 5 mM sodium lactate and 2.5 mM sodium arsenate, was carried out. After 5 days of incubation at 22° C. gas samples were collected for the chemical composition analysis in a gas chromatograph GC-MS and GC-AED. The conducted analyses revealed that the only volatile compound produced by the *Shewanella* sp. O23S strain with the plasmid pSheB is dimethyl monosulfide (DMS). The production of volatile arsenic compounds was not observed.

Example 8

Figure 6:
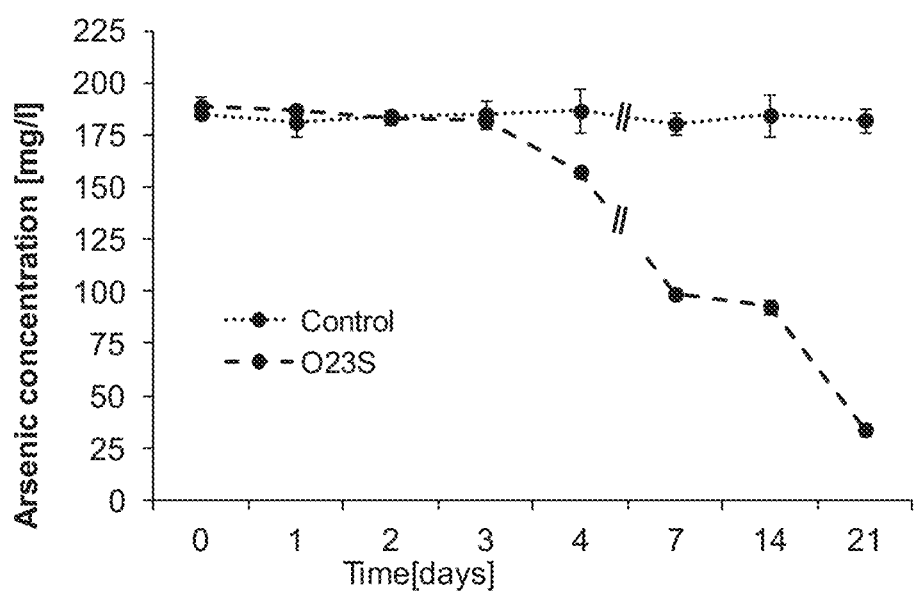
FIG. 6. Shows a graph illustrating the efficiency of arsenic removal by the *Shewanella* sp. O23S strain in a medium containing 2.5 mM (187.5 ppm) sodium arsenate and 5 mM sodium thiosulfate. Sterile R1-R2 media with sodium arsenate and sodium thiosulfate were used as the controls.

Precipitation of $As_2S_3$ (Arsenic(III) Sulfide) by the *Shewanella* sp. O23S Strain in Medium Containing As (V) and Thiosulfate In order to demonstrate that a strain harbouring the plasmid pSheB, having the SEQ ID NO: 1 or its functional derivative, such as *Shewanella* sp. O23S, harbouring the plasmid pSheB can be used in bioremediation, in the processes of selective arsenic removal from the soils contaminated with arsenic, an experiment, in which arsenic was precipitated from the medium in the form of arsenic (III) sulfide ($As_2S_3$) was carried out. For this purpose, an experiment of arsenic removal from the soil was conducted in R1-R2 medium enriched with 5 mM sodium lactate (as the source of carbon and energy), Tuovinen salts (2 ml/l), and 2.5 mM sodium arsenate and 5 mM sodium thiosulfate as the final electron acceptors. The medium was inoculated to obtain the initial culture density of $10^6$ cells/ml. The cultures were carried out under anaerobic conditions, at room temperature. The arsenic content in the solution was measured at time T0, and on days 1, 2, 3, 4, and 7, 14 and 21 of the culture. The appearance of a yellow-orange arsenic (III) sulfide ($As_2S_3$) precipitate was also observed. After 7 days, a loss of 47.8% of arsenic in the solution, and the appearance of a characteristic precipitate, insoluble in water, were recorded. After 21 days of cultivation, the loss of arsenic reached 82.3% (FIG. 6). In the controls containing a sterile medium, sodium thiosulfate or sulfide, or sulfites (IV) or sulfates (VI), as well as arsenites (III) or arsenates (V), neither the loss of arsenic in the solution, nor the appearance of arsenic sulfide precipitates were observed. It was hereby demonstrated that the strain which may comprise the plasmid pSheB (SEQ ID NO: 1), i.e. the *Shewanella* sp. O23S strain deposited as KKP2045p, is capable, in the presence of mineral sulfur compounds, of arsenic removal from solutions (e.g. of soil) in the form of arsenic (III) sulfide, and thus, of its immobilization.

Example 9

Capability of Dissimilatory Arsenate Reduction by the *Shewanella* sp. O23S Strain Under Slightly Acidic Conditions In order to verify whether the *Shewanella* sp. O23S strain is capable of dissimilatory arsenate reduction under slightly acidic conditions, culture was carried out in minimal R1-R2 medium having a pH 4, enriched with 2.5 mM sodium arsenate, 5 mM sodium lactate and 0.004% yeast extract. The culture was carried out for 168 h at room temperature. An analogous experiment in medium having a pH 8 was carried out as the control. The conducted research revealed, that in the most optimal conditions, in medium having a pH 8, *Shewanella* sp. O23S has completely reduced As(V) present in the medium within 4 h (FIG. 7A). On the other hand, in medium having a pH 4, *Shewanella* sp. O23S metabolism, and the kinetics of the process of reduction of arsenates to arsenites have been slowed down, and the complete reduction of As(V) occurred after 48 h (FIG. 7B). Nevertheless, the obtained results revealed that the *Shewanella* sp. O23S strain is capable of dissimilatory arsenate reduction under slightly acidic conditions.

Example 10

Resistance to Heavy Metals of the *Shewanella* sp. O23S Strain

In order to use a strain in mobilization of arsenic from polymetallic deposits, copper concentrates or flotation tailings, the used strain must be characterized by a high resistance to heavy metals. In accordance with the above, *Shewanella* sp. O23S capability of tolerating the presence of heavy metals, and capability of reducing As(V) to As(III) in the presence of heavy metals was verified.

In order to verify the range of tolerance to the presence of heavy metals, the *Shewanella* sp. O23S strain was cultured in liquid complete LB medium supplemented with the appropriate heavy metals solutions (Table 3):

TABLE 3

Metals and their compounds used for the determination of the minimal inhibitory concentration (MIC).

| Analysed metal | Chemical compound | Concentration [mM] | Concentration [mg/l] |
|---|---|---|---|
| As(III) | NaAsO2 | 0.5-5 | 37.5-375 |
| As(V) | Na2HAsO4 | 1-600 | 75-45000 |
| Cr (III) | Cr2(SO4)3•18H2O | 2-12 | 104-624 |
| Zn (II) | ZnSO4•7H2O | 1-6 | 65.5-393 |
| Se (VI) | Na2SeO4•10H2O | 1-20 | 79-1580 |
| Cu (II) | CuSO4•5H2O | 1-6 | 63.5-380 |
| Co (II) | CoSO4•7H2O | 1-6 | 59-354 |
| Mn (II) | MnSO4•H2O | 1-20 | 55-330 |
| V (V) | NaVO3 | 1-20 | 51-1020 |
| Cd (II) | CdSO4•8H2O | 1-6 | 112-672 |

The overnight culture of *Shewanella* sp. O23S was passaged to LB medium enriched with the appropriate metal or metalloid compound (to obtain a density of approximately $10^6$ cfu/ml) and was incubated for 24 hours at 22° C. Subsequently, $OD_{600}$ measurements were carried out and the values of minimal inhibitory concentration (MIC), which is defined as the lowest $Me^{n+}$ concentration that completely inhibits the growth of bacteria, were determined. In order to verify whether the presence of heavy metals inhibits the capability of reducing arsenates to arsenites, a test was carried out in minimal R1-R2 medium enriched with 2.5 mM sodium arsenate, 5 mM sodium lactate, 0.004% yeast extract and the addition of the appropriate heavy metals solutions.

The conducted experiments revealed that the *Shewanella* sp. O23S strain, apart from the resistance to As(III) and As(V) is also resistant to Cu, Cd, Cr, Co, Mn, Zn, Se, V (Table 4). Furthermore, it is also capable of dissimilatory arsenate reduction in the presence of heavy metals. Only in the presence of iron (III) the capability of dissimilatory reduction was not demonstrated, because this strain is capable of Fe(III) reduction and using it as the final electron acceptor (Table 4).

TABLE 4

The value of the minimal concentration of heavy metals, inhibiting the growth of bacteria (MIC) and the value of the maximum concentration of metals allowing for dissimilatory reduction of 2.5 mM sodium arsenate by the *Shewanella* sp. O23S strain.

| Element | MIC value [mM] | Reduction of arsenic in the presence of the metal [mM] |
|---|---|---|
| Cd(II) | 1 | 1 |
| Co(II) | 2 | 2 |
| Cr(III) | 5 | 3 |
| Cu(II) | 3 | 2 |
| Fe(III) | 5 | — |
| Mn(II) | >20 | >5 |
| Se(VI) | >20 | 5 |
| Zn(II) | 3 | 2 |
| V(V) | >20 | >5 |

LITERATURE CITED IN THE DESCRIPTION, IS IN ITS ENTIRETY INCORPORATED HEREIN AS REFERENCES

Bultreys A. and I. Gheysen. 2000. Production and comparison of peptide siderophores from strains of distantly related pathovars of *Pseudomonas syringae* and *Pseudomonas viridiflava* LMG 2352. Appl. Environ. Microbiol. 66:325-31.

Drewniak L. 2009. Characterization of arsenic bacteria isolated from Zloty Stok gold mine. PhD thesis. The Faculty of Biology. University of Warsaw.

Drewniak L., Matlakowska R., Rewerski B. and Sklodowska A. 2010. Arsenic release from gold mine rocks mediated by the activity of indigenous bacteria. Hydrometallurgy 104 (3-4): 437-442

Fornasiero D., Fullston C. L. and Ralston J. 2001. Separation of enargite and tennantite from non-arsenic copper sulfide minerals by selective oxidation or dissolution. International Journal of Mineral Processing, 61 (2): 109-119

Guo H. and Yen W. T. 2005. Selective flotation of enargite from chalcopyrite by electrochemical control, Miner Eng. 18(6):605-612.

Kovach M. E., Elzer P. H., Hill D. S., Robertson G. T., Farris M. A., Roop R. M., Peterson K. M. 1995. Four new derivatives of the broad-host-range cloning vector pBBR1MCS, carrying different antibiotic-resistance cassettes. Gene, 166:175-6.

Kushner S. R. 1978. An improved method for transformation of *E. coli* with ColE1 derived plasmids, str. 17-23. Boyer H. B. i S. Nicosia (ed.). Genetic engineering. Elsevier/North-Holland, Amsterdam Mantur A., Rajpert L., Rewerski B., Ruszkowski D., Sklodowska A. and Drewniak L. 2011. New dissimilatory arsenate reducers—isolation, characteristic and potential application in biometalturgy. Prezentacja na konferencji BioMicroWorld 2011, Malaga Hiszpania Newman D. K., Ahmann D. and Morel F. M. 1998. A brief review of microbial arsenate respiration. Geomicorbiol. J. 15:255-268

Olson G. J., Brierley J. A. and Brierley C. L. 2003, Bioleaching review part B: progress in bioleaching: applications of microbial processes by the minerals industries. Appl Microbiol Biotechnol. 63(3):249-257

Piret N. L. 1999. The removal and safe disposal of arsenic in copper processing. JOM, 51 (9) 16-17

Rawlings D. E. and Johnson D. B. 2007. A Review: The microbiology of biomining: development and optimization of mineral-oxidizing microbial consortia. Microbiol. 153: 315-324

Robins R. G. 1985. The aqueous chemistry of arsenic in relation to hydrometallurgical processes. Proceedings of the 15th Annual CIM Hydrometallurgical Meeting, Vancouver, Canada, pp. 11-126.

Sambrook J. and Russell D. W. 2001 Molecular cloning: A laboratory manual. Cold Spring Harbor Laboratory Press, New York.

Schwyn B. and J. B. Neilands. 1987. Universal chemical assay for the detection and determination of siderophores. Anal. Biochem. 160:47-56.

Senior G. D. Guy P. J. and Bruckard W. J. 2006. The Selective Flotation of Enargite from Other Copper Minerals—A Single Mineral Study in Relation to Beneficiation of the Tampakan Deposit in the Philippines. Internation Journal of Mineral Processing, 81: 15-26

Sklodowska A. and Matlakowska R. 2007. Bioleaching of metals in neutral and slightly alkaline environment In Microbial Processing of Metal Sulfides Edts.: Edgardo R. Donati Wolfgang Sand Published by Springer, Dordrecht, The Netherlands, ISBN-10 1-4020-5588-9 (HB); ISBN-13 978-1-4020-5588-1 (HB) pp. 121-130

Tuovinen O. H. and D. P. Kelly. 1973. Studies on the growth of *Thiobacillus ferrooxidans*. I. Use of membrane filters and ferrous iron agar to determine viable numbers, and comparison with 14 $CO_2$—fixation and iron oxidation as measures of growth. Arch. Mikrobiol. 88:285-98.

Xia L., Yin C., Dai S., Qin G., Chen X. and Liu J. 2010. Bioleaching of chalcopyrite concentrate using *Leptospirillum ferriphilum, Acidithiobacillus ferrooxidans* and *Acidithiobacillus thiooxidans* in a continuous bubble column reactor. J Ind Microbiol Biotechnol. 37 (3): 289-295

Xia L., Dai S., Yin C., Hu Y., Liu J., and Qiu G. 2009. Comparison of bioleaching behaviors of different compositional sphalerite using *Leptospirillum ferriphilum, Acidithiobacillus ferrooxidans* and *Acidithiobacillus caldus*. J Ind Microbiol Biotechnol. 36(6):845-85

Zobrist J., Dowdle P. R., Davis J. A. and Oremland R. S. 2000. Mobilization of Arsenite by Dissimilatory Reduction of Adsorbed Arsenate. Environ. Sci. Technol. 34:4747-4753.

The invention is further described by the following numbered paragraphs:

1. An isolated plasmid comprising the fragment of the nucleotide sequence from 63978 to 72599 of the plasmid pSheB, having the sequence shown in SEQ ID NO: 1 or its functional derivative.

2. An isolated plasmid pSheB, having the sequence shown in SEQ ID NO: 1 or its functional derivative.

3. A bacterial strain comprising the plasmid defined in paragraph 1 or 2, or comprising the nucleotide sequence comprising the nucleotides from 63978 to 72599 of SEQ ID NO: 1 or its functional derivative.

4. The bacterial strain according to paragraph 3, characterised in that it is the *Shewanella* sp. O23S strain deposited in the IAFB Collection of Industrial Microorganisms in Warsaw, under the deposit number KKP 2045p.

5. A composition comprising the isolated plasmid defined in paragraphs 1-2 or the bacterial strain defined in paragraphs 3-4 or combination thereof.

6. Use of the bacterial strain defined in paragraphs 3-4 and/or the composition defined in paragraph 5 for the selective removal of arsenic from mineral resources, raw materials industry waste or soil.

7. The use according to paragraph 6, characterised in that the mineral resources are polymetallic copper deposits.

8. A method for selective removal of arsenic from mineral resources, raw materials industry waste or soil, wherein the step of dissimilatory arsenate reduction is carried out with the use of the bacterial strain defined in paragraphs 3-4 and/or the composition defined in paragraph 5.

9. The method, according to paragraph 8, wherein the step of dissimilatory arsenate reduction is carried out under neutral or slightly alkaline conditions.

10. The method according to paragraphs 8-9, characterised in that the mineral resources are copper deposits.

11. A method for selective arsenic removal from a variety of mineral resources, raw materials industry or soils, wherein the removal of arsenic is carried out by dissimilatory arsenate reduction using a bacterial strain comprising the plasmid pSheB, having the sequence shown in SEQ ID NO: 1 or its functional derivative, preferably the *Shewanella* sp. O23S strain deposited as KKP2045p, which method comprises the following steps:
    a) preparation of the mineral resources, wastes or soils and mixing with an appropriate culture medium enabling the cultivation of the strain,
    b) addition of an inoculum of this strain and earring out the culture under conditions enabling its growth and conduction of dissimilatory arsenate reduction.

12. The method according to paragraph 11, characterized in that, step b) is followed by step
    c) of selective removal of arsenic, released from the solutions obtained in step b).

13. The method according to paragraph 12, characterized in that, the removal of the released arsenic is carried out by flotation, preferably by selective precipitation of arsenites with sulfides.

14. The method according to paragraphs 11-13, characterized in that:
    step a) is carried out by: shredding and fractionation of the mineral resources, wastes and soils, preferably to the fraction of 125-250 µm.

15. The method according to paragraphs 11-14, characterized in that the culture medium is R1-R2 medium, supplemented with sodium lactate, yeast extract and Tuovinen salts.

16. The method according to paragraphs 11-15, characterized in that, the culture medium does not contain $NO_3^-$ and $Fe^{3+}$.

17. The method according to paragraphs 11-16, characterized in that in step b), the culture is carried out under anaerobic atmosphere conditions, and is carried out with flushing of the medium with a mixture of gases $N_2$:$CO_2$, preferably in a ratio 4:1.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated plasmid comprising a nucleotides 63978 to 72599 of SEQ ID NO: 1.

2. An isolated plasmid pSheB, having the sequence shown in SEQ ID NO: 1.

3. A bacterial strain comprising a nucleotides 63978 to 72599 of SEQ ID NO: 1.

4. The bacterial strain according to claim 3, wherein the strain is a *Shewanella* sp. O23S strain deposited in the IAFB Collection of Industrial Microorganisms in Warsaw, under the deposit number KKP 2045p.

5. A composition comprising the isolated plasmid of claim 1.

6. A composition comprising the isolated plasmid of claim 2.

7. A composition comprising the bacterial strain of claim 3.

8. A method for selective removal of arsenic from mineral resources, raw materials industry waste or soil, wherein the step of dissimilatory arsenate reduction is carried out with a bacterial strain comprising nucleotides 63978 to 72599 of SEQ ID NO: 1, wherein the method comprises:
   a) preparing the mineral resources, waste or soil and mixing with an appropriate culture medium enabling the cultivation of the strain,
   b) adding an inoculum of this strain and culturing under conditions enabling growth and conduction of dissimilatory arsenate reduction,
   whereby arsenic is selectively removed from the mineral resources, waste or soil.

9. The method, according to claim 8, wherein the step of dissimilatory arsenate reduction is carried out under neutral or slightly alkaline conditions.

10. The method according to claim 8, wherein the mineral resources are copper deposits.

11. A method for selective arsenic removal from a variety of mineral resources, raw materials industry wastes or soils, wherein the removal of arsenic is carried out by dissimilatory arsenate reduction with a bacterial strain comprising the plasmid pSheB, having the sequence shown in SEQ ID NO: 1 wherein the method comprises:
   a) preparing the mineral resources, wastes or soils and mixing with an appropriate culture medium enabling the cultivation of the strain,
   b) adding an inoculum of this strain and culturing under conditions enabling growth and conduction of dissimilatory arsenate reduction,
   whereby arsenic is selectively removed from the mineral resources, wastes or soils.

12. The method according to claim 11, wherein the bacterial strain is a *Shewanella* sp. O23S strain deposited as KKP2045p.

13. The method according to claim 11, wherein step b) is followed by step c) releasing the arsenic from the solution of step b).

14. The method according to claim 13, wherein the removal of the released arsenic is carried out by flotation.

15. The method according to claim 11, wherein step a) is carried out by: shredding and fractionation of the mineral resources, wastes and soils.

16. The method according to claim 15, wherein the mineral resources, wastes or soils of step a) have a fraction size of 125-250 µm.

17. The method according to claim 11, wherein the culture medium is R1-R2 medium (R1 salt: NaCl—1.17 g/l; KCl—0.3 g/l; $NH_4Cl$—0.15 g/l; $MgCl_2 \times 6H_2O$—0.41 g/l; $CaCl_2 \times 2H_7O$—0.05 g/l and R2 salt ($KH_2PO_4$—0.17 g/l; $NaHCO_3$—2.0 g/l; $Na_2SO_4 \times 10\ H_2O$—0.07 g/l mixed in a ratio 1:1), supplemented with sodium lactate, yeast extract and Tuovinen salts.

18. The method according to claim 11, wherein the culture medium does not contain $NO_3^-$ and $Fe^{3+}$.

19. The method according to claim 11, wherein in step b), the culture is carried out under anaerobic atmosphere conditions, and is carried out with flushing of the medium with a mixture of gases $N_2:CO_2$.

20. The method according to claim 19, wherein the mixture of gases $N_2:CO_2$ is in a ratio of 4:1.

21. The method according to claim 14, further comprising selective precipitation of arsenites with sulfides.

* * * * *

SEQUENCE LISTING

<160> NUMBER OF SEQ ID NOS: 5

<210> SEQ ID NO 1
<211> LENGTH: 81591
<212> TYPE: DNA
<213> ORGANISM: Shewanella sp.

<400> SEQUENCE: 1

| | | | | | |
|---|---|---|---|---|---|
| atgcaatttg | gccaaatcgc | attattaaaa | tcgatttgcg | agctagcgaa | tattgtgatt | 60 |
| tgcttgaaaa | aaggaaagat | atttgaatcg | ttttttattt | caatcattgc | ggtaattccc | 120 |
| cttttttgctg | ttgcttccaa | tacgaccaat | cagtcgttta | atcaggctaa | aaaacagctg | 180 |
| ttatcggtct | atcaagatca | gcgggaaacc | ctctattgcg | gtgctgcatt | tgacgcaaaa | 240 |
| gggcaggtaa | tctctccgcc | aggatttact | actaaaacac | atttagcgcg | cgctaaaaaa | 300 |
| atagaatggg | aacacgttgt | acccgccgaa | aatttttggca | aagcatttat | tgagtggcgt | 360 |
| gatggccatg | ggcaatgtgt | cgatagcaaa | ggtaagtcgt | tcaagggccg | caagtgtgcc | 420 |
| gagaagatga | atgttgagta | tcgatacatg | caagcggata | tgcacaatct | atttccggcc | 480 |
| attggcgctg | tgaatgcgct | gcgcagtaat | tacaattttg | ccttgttacc | gtcggctaaa | 540 |
| tctgattttg | gtgcctgtga | tatgcgcatt | gatggtagca | aagctcaacc | tcccgaagac | 600 |
| gctagagggc | gcattgctcg | gtcctatctg | tatatggacc | aaagttatcc | taaatattcg | 660 |
| atgagtaagt | cgcagcgcca | gcttatgagt | gcgtgggata | agcaatatcc | ggtgaatatc | 720 |
| caagagtgcc | agcgggctaa | aaaaattgcc | gccattcagc | tcaatgataa | tgagatcgtc | 780 |
| aaaagtcgtt | gtcagcaagc | caatattttgg | taaacatacg | agaagctatg | aattatattg | 840 |
| ataataacac | cttgtcagag | ttggatttgg | tttggttgcg | taagttaaa | gccagtaaga | 900 |
| atctcgatac | gctattaatc | caagtgaccg | gcgctgagcg | taaaatagat | caagatcctg | 960 |
| cgctcactca | acgtgagaag | tttgataatc | taacgtcgat | taatacggcg | ttttgtcttc | 1020 |
| gtgaaacgga | agtaaaacag | ctcaccggag | attggtctta | aactgggcgt | tcccttcggt | 1080 |
| cgggcttttc | gcttcgctcc | ccgcgataac | gtgatccact | gatggcaagc | aagcttgccg | 1140 |
| tggctctacg | ttcctgcttg | ccaatcccta | acgcaatcac | caagccccaa | acaaaagcaa | 1200 |
| acatcaactt | cctaaagcac | tgtccggttc | attgccggct | aaagtgtgag | taagcgtgcg | 1260 |
| cttctctatc | gcttgtcatc | gtttccctgc | caataccgtt | cacgtctgcg | ctgtcacttc | 1320 |
| ttatctgtct | catttcacaa | cctgcccgcc | aagggaggct | tcgccgctgc | gcgcccttgt | 1380 |
| ctgtcagaac | gtgaaatgag | tcaggaagtt | aggcgaagac | gagaacgata | tttaaacgac | 1440 |
| aggaaaacaa | gcaatgacaa | actcaattca | agcgcaagca | actcacacta | aagccaccac | 1500 |
| tttacctgcc | agcccaaaga | ctcaagcagg | ctctcacaag | cccgatattg | ctcaaaaatc | 1560 |
| agcaactgcg | gctaacgctg | tggtggcatt | ggcttcaaca | gcaaagccag | tgttactgca | 1620 |
| attgcagatt | aaccagttgg | tgttgtctga | aagaacgcg | cgtaaagaaa | atgcgtctaa | 1680 |
| ggctgacgat | gaacagttgt | atgcctccat | tttggcgcat | ggcattttac | aaaatctgat | 1740 |
| tgtcgagccc | atgaacgcgc | aaggcttata | cccagttttg | ggcggtggtc | gtagactgag | 1800 |
| acagctcatt | aaagcggtca | aaataataa | gctgaaaccg | aaaacgcttg | tgcctgttaa | 1860 |
| gttgctgaca | gccgaagaag | tggccaacta | tgccaccgag | ctatcaatga | ctgaaaatttt | 1920 |
| cacacgtgca | aagatgcacc | cagtcgatga | atttcacgct | tttgctgaca | tggtgaataa | 1980 |
| gggcgctagc | attgctgatg | ttgcgacgcg | gtttggcgta | acagcgaaat | tcgtgcagca | 2040 |
| gcgcatgaag | ttaagcatgg | tcgcccctgt | tgtgctcgat | gcgtacaaag | cggggaacgt | 2100 |

```
gtcgcttgat gttgtgatga tattcacgat tgccagtgtc gaaaaacaag tcgaagtgtg    2160
ggagctggca ggcgatagac gttacaacga aaaccagttc cgcaatatgc ttaaagacgc    2220
cgctgtgaat gctgatcact atttggctca gtttgttggc caagaagaat acgaaaaagc    2280
gggcggggtt gtgacctcag acttgttcag tgacgaagtc tatcttgatg ataaagcgtt    2340
gctcgaatca ttagcgaccg caaaattgga aatcgaagca gcaaagttaa tcgcgcgtgg    2400
ctggaagtgg acacagataa agttagtttc tgaatacgat gaacttgcag ggtttgggct    2460
tctagactca aaagagggtg agtatgatcc cgctgaaatg gcgctagcgg ggtgtatgct    2520
cgtgttaaaa agttatggtg agcctgtcag tatctatatt gggttagtgc ataaggacga    2580
taaaaaggcg ctggcacaat taaaagccag tgtgcaatca gacccactca acgtgggtga    2640
cgtgaaaaaa attgaagaaa aggatactag cggttattcc gctgcgctta atgacgactt    2700
acgggcgcag cgtttgatta tcacgaaaca tgcgttaatg agtgcgccaa gcgttgcgct    2760
tgatacgttg catttttctg tctgtgtaag cgcgttcact gattcacatt atggcagtcg    2820
tccactgcat atcagcgtta acgacaccac ttgccatcct aaaacgggat cgctcacgga    2880
taacaaagcg gtgcagttaa tcgagggtgt aaaagccagc ctaaatttag cgtgggttgg    2940
tctgcccacg gtcgctgaac gctttaacgc ttttttgcgcc ctcgatgtaa aagagaaaga    3000
aaagcaggtg gcttacgcca cggcttccat gttcgaggcg tcaattgata atagtcataa    3060
agctgttgag gccgtgatat ccacgctcga tgtgaaatgg tctaactact ggcgacctac    3120
tgcggaaacc ttctttaagc gcgtgagttt gtcttgttta attgatatgg ctcagcctgt    3180
catgggtgag cagtgggcat tacaagccgc tgcactcaag aaaaaggatt tagcaaatca    3240
ggttgatagc ttagtgaacg gtgagcgaaa agggctagat gatgcacaaa agcctactt    3300 tgatgcgttg atgccagctg gattttaagc cgcatactga tgcagattta ccctgttaat    3360
tcagggtaaa tctgagcaag aattaactaa ataaattgag ttgtgtgtat gcgtgtgtat    3420
aatggttcaa cggttaacgc agaggtttta caatgctatt tatggtcggg atcgaaagcc    3480
ctgctgatga aacgcaggcg tttggtatcg ttatccccgt gtttgaaaaa ttaggctatg    3540
gctgtttttc ggcggcggat tgccaagaag aaatcttgtt taaggctaaa gaagccattt    3600
tattaatggc tgaggaagtg atcaacgatg gtcatttagt cgatagtttg aatgaaggat    3660
atcgcgacta tcaggcattg catcccaagt tcgaccaatg gctggcctta gaggtgccac    3720
tagaggcgct taaagccaaa caaaaacgcc tcaatatcac attgtcagaa tcgcagattg    3780
tacgtatcga tagctttgtg gcgtttcatc gcgagttcaa agaccgttcg gacttcttgg    3840
ccaaggcggc cgataagtta atgaacagcg cagactcagt aagatcgtgt caaaagtgg    3900 gagattgata tgggcaaagt aaccggtatt ccattttcag aggtgaaagc gcagcttatg    3960
gataatcccg aggttgtcgc agcctatgag caagcagtac aagccgatga accgatccac    4020
attattccag tgcaacacag tgagggcgtt atcatgccaa tcaacaatat cgtgagttgt    4080
actcgtgaag gtcatcatgt ttattttcct ttgtgaatct gtttggtggc catcactatc    4140
cagtgacgat gattttatg ccctctggcg cggtgaatgt cgttgtcggt ggggcgcggt    4200
atcgatgcca agccaatcaa gtgcagcgcg tgattgatga gtctgggctt gagcatgagg    4260
gcttagcgtg tttgaagtat ttgattgaag cgggggagtt gaattttcat attcccgctg    4320
atgttcacga gcagcttaaa gtgcatccag agtttcaaaa ataccgcctc atcgagtggg    4380
aagatgaaga catgtgagtg ttgcgataac gacaaggaga attaggcatg tctcaacgtg    4440
```

```
cgatagagat tgtaaagata agtgatctca agtccgtcaa acagggtgaa gtgtttgagt    4500
ggtgtattga ttatgaagaa tttcaatggc gcaagggaga tgactttcta aggagtcgaa    4560
caggcgtcga ttctccttgg gaaatttggc cgttgactga taacaccaaa accgctgcta    4620
atcgcaaagt ctttaagctg ataaaatgaa aggacaaaat gatgatgcg ttcttggata     4680 atgtactatt ggtgatttgt tggctgttca ttgccatttc tgctatttat ttcgtcgcag    4740
ccgcattcag gctcgttttt attggccgcc gatagtcgct attccctgtt agttccccgc    4800
aaaacgcgaa acaagcggcg gctgcgccgc ccttttccgt ttatctgaca ataccccttg    4860
gtgtgctttg aaacgtgcct cggcggttaa tctatttact ctgagtgtct attggctgct    4920
gtcgcgctat gtcatctaaa acaactgat gaacttgggc gttcccttcg gtcgggcttt     4980
tcgcttcgct ccccgcgata acgtgatcca ctgatggcaa gcaagcttgc cgtggctcta    5040
cgttcctgct tgccaatccc taacgcaacc accaaaccgc caagcacagt cctactcact    5100
gcgcggcaag tgtggctaag ctggtcgttt cattcggcat catggccgct cctggtgcta    5160 tcccttttcgt ttacgcttcc gtcttatctg tcgctcacca caacccgctt gccaagggtt   5220
cgcttcgccg ctgcgcgccc ttgtcaatca gaacgatggc gagcgagcag gacgtcaggc    5280
gaaaacgaag atgatagacc ccaaacggag caagcagccc atgacacact caatcactac    5340
cccagcaagc cacactaagc cttttcagcga gcaagccagc ttacaagcga caagcaggct   5400
ctccaaagac gatattcaac agcaaaaaag gggcgagttg acgatcattg ttttaactga    5460
aatgaatttc tttcacttct gcggcctcgg acttgagggc gtggctaatg aggcatggta    5520
tccctattca caagggttat tgtttgaagc ggtcgagcgg tacttagtcg cggcaaaagt    5580
ggctcaaaat gtcgtatcaa tcgatcaacc tcgacgcaat ggcgcaagta ttgattatcg    5640
cgtgcgtttt aatgtgttta gcactgacaa aaaacgggtt tcggttcgtt ttcctgtcgt    5700
gattaagaat tttggcaacg atacgcaatg cctctcagtc gatgaactaa cgagggcgtt    5760
aagtctgaac tatcgaaata agcacgtttc aatcatgtgg tctttaccct cggggatcac    5820
atcaacggtt tatgtgtcgg tggcggctga cggggggata agcgattgct atacacatca    5880 tgcccttttgg tttgtgatgg aaggggggttg cattgagttg gccactaaca cggggggcgat   5940 atgatatgtg caaaccctca gtgacgtttg aagaaatgaa cacctatttta caagggcaat    6000 ataaacatga acgtttatat ggtcgcaccc ctgcaacggg ttggcctgcg gactatgcaa     6060
catcggttgt cagtagccac atggatgatt tgaatgctaa cgggatcggg tacattggcc     6120
atcacgaatc cgcgacaggt caggcgatcc gttataccgt ggacgaggtt aaatattccc    6180
cccgcttttt tattgttggc tatgactccg aaaacgatat tgcccaaaaa caatgctatt    6240
ttattgattc agcgatcaat atcgaaaggg ctcgcgctaa atgcttagag agtgctaatc    6300
gctatccgat agtgagaatt aaggatctac aagggcagtt tgtgtaaaca gcctgaacgt    6360
cttacagggg aacatgcgtt cccctttctc gttaattcac atcatgaccc acttcgtttt    6420
tttcgtctta agttcaaacc gttcgatagg ttaagtctcg aaaatatcct ttttgcaac     6480 tatatatagt tgcactttttt gcggttgatt tggtataatg atccctata tagcagggg     6540 cattatgacg aaaacggata aattattagc aaagctcaaa tcgtccaaaa cactgacttg    6600
gaatgaatta gcgggggcgt taaaagtgct cggctatcaa caagtcgagg gtgatggttc    6660
gagggttaag tttgataatg gcattccgaa ggagttaatc aacctgcata aaccgcatcc    6720
taaaaatgaa ttaaaggctt acgcattgcg ccaagtgaga gacaaattaa ccgaatgggg    6780
gaaactatga tgcaaaatac aatgacatat aagggttatc acggctctgt agaaatcagc    6840
```

```
ccagaggata atattctgtt tgggcaggtg ctattcattt caccgttgat caactatgag   6900
gccgaaacag ccaaagggtt agagcaagcc tttcaagagg cgattaacgc ttatcttgct   6960
gactgtgctc aacaggacat tcaaccagag aagccttgta agggatcgct taatgtcaga   7020
ttaggccatg acttgcattt ggctgcgtct atcgcggcat ttcaggcatc gactagcacg   7080
aatgagttta tcaaaagggc agttcaaaaa agcgtgggtt tgtaggctgc aaatcgttgt   7140
cgagcaatga tatcagcctg agccatgtga tctacttaaa ctgaacatta cccctgtta   7200 gctccccgca aaacgcgaaa caagcggcgg ctgcgccgcc ttttccgtt tatctgacaa   7260 tacccctggg tgtgcttga aacgtgcctc ggcggtaat ctatttactc tgagtgtcta   7320
ttggctgctg tcgcgctatg tcatctaaag acaactgatg aacttgggcg ttcccttcgg   7380
tcgggctttt cgcttcgctc cccgcgataa cgtgatccac tgatggcaag caagcttgcc   7440
gtggctctac gttcctgctt gccaatccct aacgcaacca ccaaaccgcc aagcacagtc   7500
ctactcactg cgcggcaagt gtggctaagc tggtcgttca tttcggcatc atggccgctc   7560
ctggtgctat ccctttcgtt tacgcttccg tcttatctgt cgctcaccac aacccgcttg   7620
ccaagggttc gcttcgccgc tgcgcgcccct tgtcaatcag aacgatggca agcgagcagg   7680
acgtcaggcg aaaacgaaga tgatagaccc caaacggagc aagcagccca tgacacactc   7740
aatcactacc ccagcaagcc acactaagcc tttcagcgag caagccagct tacaagcgac   7800
aagcaggctc tccaaagacg ataaattgaa aggctttaaa gatgggaaac tacgtaaaaa   7860
cgcaaaaagt aaaattgcag tgttgttgtc aatggcgaca aagatcgtac tcagaaccca   7920
aacaatgggg atggatgatt gttttaatga taatgccccg cagatcgttg atataaattt   7980
cttttggagc tggtacgaga aggaatactc agagctagaa attatgtaa ccgtgattga   8040 tggtgtatta actaaagtgc gttttctga ttgtccctat catttttctg acgatatcgt   8100
tttgaccttt gaagaagtca aagcgaaaaa gccgcatttt acctatgcac aagttaaaca   8160
ggcattgtta gacggctatt tatgcccgtt gtcgaacgat tccaaagccc ctgagccaac   8220
accgccaaac gatgacaaca ctcgcaaagt ggttagtttt ggcgattatc aagatcgcct   8280
cgaaagcaag cgtgaccgct tagagagcgc cgcaggtaaa gcggcggcag actcaaacaa   8340
attttatgag tcgtctagaa gccttgcttc ttgtattccg ttcggccagc caattttggt   8400
tggacaccat agcgagaaac gcgcgagacg ccacgcagac aagatttta atgatatggg   8460 taaatctgtt gcggcaagca aaaagcggg ttattacgct gacagagcgg ccagcgttgg   8520
cactaatggc attgcatcgg atgatcccga agctatcgcc aaactaaaag aaaaactcgc   8580
aggcttggag cgttcacaag aaacgatgaa agcgatcaat aaagttatcc gctctaagca   8640
tatgacggac gccgacaaaa tcgagtacat gacgcaaacg cataagctaa ccgaaaaaga   8700
agcggaagaa ttactaaagg gggattttg cggtcgggta gggtttgcta gttactcaat   8760
cgcaaataac agcgcgacta ttcgcaccgt aagggatcga attgaagatt tggaaaagtt   8820
acataatcaa gttgcattga gtgcaagcgg tgaaattgag gggatttctt gggcgttata   8880
tgaggaagat ggacgtatta aaataacttt tgatgatata ccaagcgagg cgctacggtt   8940
aacaataaaa aaacatgctt ttaaatggtc gcgatattct aaagctttggg ttcgtaaaat   9000 aacacctaat gccatttata gcgcaaaaca attgataggc aagttggcag aaaagtagca   9060
gctgtcaaaa tgtgaaatcc ttgctaatta ttaatggtta aagtggcggc tctgccgtca   9120
tctaatttac aactggtttt aaatggagga ggttgaggcg ttaaaaattt cagaggtcgg   9180
```

```
cgcgattgaa tgaaataaga ttaatttcac cttgctatgt gtagattttt tataataaat    9240
tttggtgagt aaataaacgg agaagtacgg cggggattgt gttgccatca atcaatgtaa    9300
aatgccattt tttagttgtt taaagttttg cgattttttac gaggcagcat tgcacgattt   9360
aactcaccta gcaggatatt aagatcgttt tgatagaaat aaaggattta actttcgctc    9420
atgtaattgc caattttaaa agccattcgc cgaattagga gcaagttctt ttaatggttt    9480
agttaagtgt taacggtaac gttcaacatg attcctatat agcaagttgg ctagaaatgt    9540
tgaaagggat aatcgcagca tctaaggcac atcattattt aatcgaatta acgttataaa    9600
taaaagccca tctagtttaa tgagttcagt ttaaataaat agtaatggga ttttttatgtt  9660 agaaacaata gaagaaaaag ccgcaagaga aaagagggtg ttagcgtggc ttgggctgg    9720 gtatgtctcg caaggcgtac ttgcgctaat cgaaaattca gcaatgaag aactggcagt    9780 attattttac cgtcacgcgt tgggagattg ggggctcgtt cctgatgagg ataggcaatc    9840
taatgatcac gcacttcgaa ataatgaacg ggtaatatca tcctatttat tcgcagggat    9900
taagattttg atcatcactg aggcagacag agcacgaacc accgcattat tgccaagcga    9960
atattaagcc gccacgcttg cagaaaacgc actcattgag tgcgtttttt tggcttgaaa   10020 atccccgat accttttgccg cttcatacgg cagcagccta gcaaaaatcg aaaattccca   10080
aaaaatcccc aaaaaatgaa aagtgcaaaa ccctggcgaa atagtgaagt tggaaccttg   10140
agaataagac cacaccccac gcaagaattg ataaatcaat tcttatggtt gtttgtggtg   10200
taaattattg aaattaaatg tttaaatatc aaaatagttt aatattttt tttgaaaatt   10260 catttcgttt ttacactaaa tcgtattaaa ggtgtattaa taaaataata caatcgtatt   10320
aaaagccctt gtaccaatgg tttcaggcgg attaatacag tattaatacc gtgtgtatta   10380
tttagtatta aagtgatgtt tataaaagaa ttacttatta actcattttg tgagtgtatt   10440
aaactttaat acactggtta atacagttat aatgcaaacc gatacgttgt taatacactt   10500
ttaatacatt ggataatgtc actatggcca gaagtaaagt tgtgcaagtc ccctgcgatg   10560
cagatctcta tgccaagatt gttgcttatc gagaagagaa ggggttagaa aaagatgctg   10620
ctgccgcgcg agatttgatc ttgtttgctc tgcgtattct tgagcataaa gatgatgccg   10680
aggggttatc tactcgcgaa ctgttagagg tgattttgac ctatacagtt aaggcacaac   10740
acactagcag tttggtctat taccagacat acaatgcggc tcctgtagat atacagaatg   10800
caggtattaa gcataaggac actatgagaa aggcagagga aaaagttgag cagattttag   10860
cgggcgaaaa taaagaggac taagtgtcct ctttatatat tcattacatg gtctttttccc   10920 caatatccaa tttaggattg tcgatgttgg gggagtattc tttcgtcgtt gaacggtggc   10980
tatccattgc taaatgttga tagtgttcat cgtgctttat tttattcgtc gttacgttag   11040
tgctgtcatc tttcatcgtg atattttttg tgcctgcaat atcatgactc aatgattgaa   11100
tggctttaga tagggtatta tctttttgtcg tgatgctata gatcgcttcg ttgactaatt   11160
gctttgtcgt ttcgactttg tttaagccgt caggtatcag gctgggttca ataataaccg   11220
catgtatatt ttccttgctg aattttttcgg taaggtcatt agccagtttt gcagtgtctt   11280
gtgaattatc aagtaccact atcacgtttt cgcgcaattc atttgtattg aatgttttgg   11340
tgtcattatt attgttaagc gcaataacgt cagccccgtt tttattatca gcatttatct   11400
taagcgcgtt ctctacaccg acagcgacaa tgctatagtc taaattattg cctttgttga   11460
tcgtcgtgct gttccccgat ttggagccga gtatgcgctt atttatttta agcgctgcaa   11520
tgtcaccgct ggatttatca aggtaagcaa tttctactgc cttggtctca tctttatcat   11580
```

```
tggtgatgtt cgcaattaat gcggggaagg ttccacgttt ttctgacgaa taaacggcat    11640
cgtgaaaacg taagttttca tgctgcttaa cgtcgatgcc ttgcttgttt aaatacgtct    11700
gtgcgagcga gttttctata ggttttgctt cgttaaagta ttgcttcgcg cgcgcttcta    11760
attggctttg cttaaccgga atggcatgtg ttaattcatc atgctgtggg ttttttacca    11820
gattatattt atcgggttcg ttcatcattt tatcggcttt ataaagtgca tccttataac    11880 tgcattttc agcgaccata atcaggttaa ttagggtgcc tttatcgccg gttttccagt     11940
ctttaaaata gccacgatat tggcccgttg tggtcaatgt taggctcccc tctttgccaa    12000
atgtcaggtt atctttgtct gattatcgc ggttcggctc acctaaaagc tgcgttgcca     12060
gcgattcact gtaggccgga agcttggcat ttagctcagt ggccatccgt tttagatcca    12120
catatccatt cacatcgagg tactttgggt tttcctgcgg caagggtttg tcattaaata    12180
gcggggtatg ttcagggtaa tacttatctc ttgtctcaag tgcagagact ttattgggat    12240
cgttattgac ccatgagagc atcattttt gcgggttatc ggtgatgatt tttacgtgct     12300
tactggcacg ggtgatatcg atatacgcgc gccttacgtt agttaatgca ccttggccct    12360
taatcgcagt aatgacattc tcataggttg ccccttgcgc catatcggcg gtgcgggtgt    12420
atgcataatc ccaatgagca tctttcaact ctttggttga gagcgttaat gtgtggttat    12480
ccgtggattt gagctgcatt tgtttatcgt caatgcggct aacggtatag gttttgttgc    12540
cctgcatttc acggtcaata tcgcttttgc ggagcatgat actgtcgcct tctgcgagag    12600
gttgctcact cttagcccaa aggttcgtga atttgtggcc atgattttg gggaagaaat     12660 gcttttcctc gccggttttc atatccgcga gggtgagcat gttattgagc ttatcgacct    12720
tcataatttc aaaataactg tctttactgg tcgttaggat taaccctgc tgatagggca     12780 acatggtcgc caattccgcc ttactggcat gaacaccgcg taatctcggt acggtgaatt    12840
gttcggtact gaggcttttt tgttgctgta acccttggcg gatttcgtgg gtaatgtcgt    12900
cgcgttcctt gttggtgtac gcaatgataa gggtattttc acgcgcttta ggtgttctgg    12960
ccaagtattc cagtgccacc gtggcgggca gggcttcggt cgccagttgc tggttttcct    13020
tcgggttatc ggttatcgac tgcaaagtcg aaatgatatt caaactttga ttgatgttag    13080
cggtagcctg cttttcgggc gttaccgcgt cgttcgcggt gggcgcgatg tattggtcaa    13140
agggtaattg ttgctgaatt ttatcaatag cgctttcgcc ttggcgatcg acaatattgt    13200
gtactgcact cagtagcgtg ctgttctgtt ggcgcacaat gtctttcatg gtgacgctat    13260
tgattgcgcc tttgtttaac gcgagttcaa aaggtttacc cgcttcttgg gacgttaact    13320
gtttagtgtc acccaagaac acggcgcgcg cgcctgttgt ctcaatcaaa tgggtaaatt    13380
tatccatttg ggcgttactg gtcatcgagg attcatcgag caagaacacg gtgttagcgt    13440
attggtctgg tttcgcatct tggcttaaaa agttgcttag gagtgattgc acagtttggc    13500
tttcgacgtt cttgtctttg agttcgttaa cggcggcgtg tgtcggcgct agacctatga    13560
attgtgtcgg tgtcttattg ggttgtgagt tgagaatgga ttcgctttgt ttaacaagat    13620
cgatacccgt ttcaagcatg gtcgatttac ccgtacccgc taacccttga cacctacaa     13680 atcggtcttt ggtggtggtg ataagcaagg tcgcgtcttt ttggccatcg gtcaggtttt    13740
gattttgact gagtacctgc gcggcgtgtt caacgctggt aaggggcgca agttgatctt    13800
tgcccgcttg tagtctgtct aaaatacgca cttcggtatc gatggcggct tgggtggtcc    13860
agcgggtgcc gtcgtggtat tcggcgctca ggagtgaggg cgcgccttta tccgtgctgt    13920
```

```
tcgtggccat gtgttgcagg gtgttgatga tttcatgttg ggtaatgctg gtgccttttt    13980
cctcaaaggc gtacttgatc gcattaacaa tcagttcttt ttgtgagtaa ccggcttctt    14040
tctcgctaat gtgctggatg gcaaaatcca cggcattgtg aataagccct ttgtcttgat    14100
gctgggcacc aatggcattc agtgctgcgg tcacatcttg ggtgagcagg gccgtagttt    14160
ggctattcac gaacttttct ggcatatcag cggcttgcat gatgcgcgaa atactggatg    14220
gtttcacttc actttttct aatcggtcat caaattgtgt gccttgtcgg tgaatatatc    14280
aatgtgtttg atgccttgtg tcagcgtgtc atgtaaccac tcttttgagg cgctataggc    14340
tttaatattg acgatgtggt gacttgcatt agggctggca ttgcttggcg tggtggcgta    14400
accatgattg agcggcgcat ggtgcaatgc actggcttta acgctgtgtt gtttgccgct    14460
ttcgtctttg agcgtgaccc attctttgga cagggcgttg atcgtataaa tttgtttgct    14520
caaaccactg tcttgatggt ttgtggccat gatgagtttg tcgccgttgg cgatatgtaa    14580
attgtccggt ttagcgatcg cgtactctgc ggctttaaag gctttgctgc tggggttaat    14640
ctcggacgct ttaccgtttt tgtctatcag cgtgaggggt tgttatcgc ggtttacact    14700 gtccaccgtc aattgctgct gttgattgcg gccaccgact ttttgccatt gggtgagtac    14760
catgcccttg gtgtactggc cgacgacttc ccgttgctgc gcggataaga acacgggatt    14820
aagggtaggg atgttgagcc caaggcgcga tacgtcacct tgattttgca gttctgcgcg    14880
gatcgcgctg ttaagctgct tcacgtcttt atgggtgccc gcaatgactt gggtgtgttg    14940
cttctcgggc agttgcgcgt aagttttgc aatcaggtta accctgtcac tgtctttgct    15000
ttcatgcagt cgcatggctg tgttgctttg tttggtggcg acccagttgc tttcgtttac    15060
gttgcctttt ttaagtacct cgatagcgtt accggctttc atgccttgct tggcattggc    15120
gtgattgagc aaaatcactt tactgttacc cgctttggct tgcgcgagca gggcattaaa    15180
gtcgttaagg ccgagtttat tggcgttctc aaccactaaa atatcgcggt tagtgttgtt    15240
ggccgtttta gtaaagctgc tgagtgtatg ggtgtggtca ggtttgaagt ggttcattat    15300
ccacttgcca atagtcgatg aatcccgttg taccgttca ctggtgtgca gtttgctttt    15360
catgtcaggg gtaatgatgt gaatacgttt accgttggct tcaccgacat tgagcagggc    15420
tgtggcgagt tgttcgctac tgccaaagac gttcactagg ttaacttgtt ttgtgctggc    15480
gaacagttca gagactttct tttggttgtc cgcatttaag cctttgcctt gaagcgtgtt    15540
ggtatcgacc acttggcgca tgttggccgt tttgggcttg atgctctcta gcaggttggt    15600
ttctgctttg atgtgggcgg cgctggtaaa ggttgcagac tctttatcaa gtggaatgag    15660
tgcgccatct tcaatgtgct tatcgagtgc caatttaata tcgagcgcat cgagcttctg    15720
gccttgcgta aattcaagcg tggctgattc cactaatttc gcgtaattaa acggttttg    15780 ggtgttactg gcgtgctcaa tcgcgcgact caccgcatcg atagcggcgg gtttgagcgc    15840
taacgcattg agtgatgttt ctcgtgacat gctgtttgtt acaaagcctg tcaggttaaa    15900
gccgctgtta ttggctttgt ttttccattg ctcaaacaag gtggcttcgc tggtataggc    15960
tttgctcttg cgggtatcct ttgcggccac gtcccgcgcg gcttgtgagt ctaaacctaa    16020
gctttgggtt tgttcgttga tttgctggct acgggtgaa aatgtatcga gtaaggactg    16080
cgggacacct tccacttcaa acaaattatt acccagtgaa cgagtttgat aacccgcttg    16140
ttcaacactg cgggctaagg cgcttttgata gagcgaggta tagtattttt gatggttata    16200
aacccgctca cctgtgccat tgatgatgcc gcctttttgt ttaaagctac ttgccagagc    16260
gcgcaatgtg ccctcgctgt ccttggtcat gttggcggtg agtgagtggg tgtgcagctg    16320
```

```
cggatcttct tcacggctgg ttttgtggcg caccatcgca aacagcaaat ttcccgtgtt   16380
ttcaaaagag gtcgctttgg tatcagggtt ggtttgtctg gcctgcgccg catctttctc   16440
gatatgcgat aacgcgaatt ttaccgcgtc atcgtgcgct gtcattaagc gtttatcgcc   16500
gcccacgagt gcaagtaaac tgaccgattt aggcgccgaa aaggtaaagt caaaaccgtt   16560
gcgggcgttg ctgttttggg ttttaagcgt ttggtcgttc aggctaccgg ctaacacctc   16620
tttgagttga tgttcttcaa cgggcttacc tagcattccc tcttgctctg ccagtttgcc   16680
aaaccattgg gtattgggct cggcgctctg ctctttcaag taatagttgg tttcccttc    16740 tttggcgtcc gctgcttttt ctaacgacac gtcaggcaaa ttgaggttct tttcttcact   16800
gaggtagtag ctggccgcgc cgccagcgct cgacgcaatg ggactgatgg aaagcataat   16860
gatattcctt tagagggacc tcgcgcgggg cacgaggtga actaatccgg taggtttatt   16920
ctgagtcgag ttgggctttg atttcgtcag acgtgaagcc cagcgctttg agttccttga   16980
tggcttcaat tcgacgcatg acgttcatcc gttcattgtc attttttagag gctttacgtg   17040 agggcttttt cgccgacaat tcgggcactc gtactgtggt gttgaatgag gtcatcgttt   17100
tagctccttt agtcgagcga tatttcttca tgtactgagg ctatttgttg ctcttcaagt   17160
cgctgtgcat cctcaatgtg ctggtcattg gccttttgtt tttcagcggc ttttttcttc    17220
tctgcatctt tgagcgctaa ctctgtcggt ttggcctttt tcgcatcgat gaggctttgg   17280
gcgaccgcat cggttttttc agcaagtttg gtcatgcgct gcgcttccgc gctgcgttca   17340
tcattgtttt catccccttc atacatggtg tcatgaatgc tttggagctt ggttttatcg   17400
gccttatcga gatgttgtgc cgcgctgaat tggtgatagt taaggcttat ctctaatttc    17460
ttcactttct cagatggtgt gtaatcccgc ttaataaacg gggcgcacag tgagcgcatt   17520
tggttaaaga ctaaatccac tcttaccacg ggataattgc caggcgtgcg cagccaaaat   17580
tgtaaatctt caagctgcat gatttcagag ggcgtgacca cagggcgggt aattgtttga   17640
tggcccagtg atacgccatc cctgatttca ttagcgccgt agctgtattg ctctttagag   17700
acatcgactt cttgctcacc taaatcgtga gacgagattt tggccatttc gttagagggt   17760
gagcggaaaa atagccgagt gttgagcaag tcgaacattt caagcgccgc attttcgcca   17820 tagactttt taagctgcgc aaaagactga ataccatga cataacagcc gccgaacttg    17880
cgcacttctg cgattgtttc ggcaagttca ggtaacttgt gcaagcttgg tgcttcatcc   17940
atcaacaccc aaattctgcg gtccggatct tcgtcttgtt ctaaaatggc ggtcgaggca   18000
atggatagcc acattgagat cagtggccgc aatgaagcat gttgctgtgc gttactggac   18060
agaaatagaa agcctctttc ggcatcgttt ttcacccact cacgaataga aaatttgcgg   18120
cgaagaagtt ttccctgttc gtccttttca tccagtccgg caaggaatcg taatgatttg   18180
atgtaggccg cgaggaccga tttaatcgat atcgccgttt tttggatttt atctgatacc   18240
agtgaggccg attcggtccc ttttaagtat tcacttaagg actcaagttc gctggtcagc   18300
atgagttcaa gcagtcgttc agtggttttgg ttctttttag gttcatcttg catcttaaat   18360
gcagtagatg aaaaaatggt acgtgctgat tgcacccaaa atggatcgcc ctcgccgtgt   18420
tggggaatga gcgcgctcgc catgttctca aaatctgagg gttcatgtgc atcacaccac   18480
acatcccaat aggcacagcg ttcatcaaac gggtttagta gtacgtccgt tgccggatta   18540
taaaatttac tgacaaaggt acagcctttg tcatagataa tggctttgtc gccccgttca   18600
cgtatccacg ttaaaaactt acgcagcgcc acggactttc ctgcgcccgt ggtgccatca   18660
```

```
agtaacaagt gttgtacttc aaagcgttct ttgaaaatac cgataccatc gagcttgaaa    18720
tcggactggc gcttgtcctt tttaagctgt tttgctaatt ccttcggcgt ggcttttgc     18780 atccccgaa taaagtgttc ctcggtttgc tcatcgcctt ttttcttgaa ataccacatg     18840
gccactgaca ggaaaacgat gccaatcaca cagctaataa ggaggtaaat ttgtgtccat    18900
aaccaaaagc ggctgttggc cgcaatcagt atcgggtttt ctaattgaga ccctaacgta    18960
ctggtataga cagtgccttg ccattcagtc tgcataacat gactttctgg tctaaacacg    19020
ctaaccgttt ggtttatcca ataataataa gcgcccgtta aggtgtcttt atcaaggaag    19080
agatagcata gcagcgctgt taagatgagc acgccaaaac acgtccagcg gacaagcacg    19140
gcgttaatct gcagaaacat ccgcaaattg tgaaataaaa tctggccacc acgggtgtag    19200
ttactgcctt tagtacgttt gggtttaag gtcattagtg aggctcctta tctaagagat    19260
tttcaataaa ggagttaagt tcttcatcat ggcggatgta gtcatttagc gctttgttgt    19320
tagtatcttg taagttttgt ttacttatgc tttgaacttt agctataaat ggcttaatag    19380
taatatcctg aatttgtaat ttcccagagt tgatgttgtt aattagcttg tcacaagcaa    19440 taatttttt atcttgcaat tcaaatttat tttttaaata cggtggcata atttgctgcg    19500
caaaattttc agattttgat ttaaccaaat cactttcgta aaagttttt agtaaatcat     19560 ttcgtaaatt taaattttcg atagtttctc cagcaaaaat cttgctgcaa ttatctggat    19620
acagtttaca aatgaaatct ataaaatctt gagtgaagtc atagttgtag tttatttggc    19680
cgcttttgag catacttgcg atgctagtat agtaatctgc taagtcttct tgcttttgtt    19740
gacctgtttt gtacttgtag gtgttaataa tacctacaag aaaatctttt tcttgtagcg    19800
atagcggtgc tgcttgagat actgaactta ataagcaaat taataatagg catgttttta    19860
tgatattcat taggttatct ctttttgatt gaaggtcatg gctattatca cattttggt     19920 cctgtattaa agggacttga ttgacgcact gtttctgcca ttttttcatc gtcacttcga    19980
ttgtctggct gtattagggt gtgcgccgct tttgcgtctg cacgggcctg ttccatatca    20040
atgctcggga cgctagacgc gttatgagtc tgttcttcgt gtaacacatc ttgtctaatt    20100
tccgcgttgc cttgcgctgc atggccttgg atgcgctcaa attcgcccgt ttggtagagg    20160
ctgtcattga acggcgcagg ggcatactgt ggtgattgct gtttattgaa atcaatatcg    20220
gcggcatagc gctcctgagc ttgcacaatg tcatcgcggt tttgcggtaa cgctgcgttt    20280
ttgtattgct cagcaatggc tttcacttca gggctgttcg taaattcagc cgcaagtttg    20340
gttcgctctt gctgcatttc tggcgtttgc cccctgatca ccgccatgaa atcaccttgc    20400
tcatctcttg atcttccaac gaattccaca aagtcttgat ttaaatcgtg actaatactg    20460
atagatccac ttttcacgcg attagccgca tcggtgtagc tttgggcttc agtgagctgg    20520
gattgggagt ttttggcgtg ggtagtcgct tcgttaagtc cttgtaggaa ggtttgtgtt    20580
tcaccttcgt ttttactgtt ggttgtactg gcttgttcgc cgctgttata ggatttgacg    20640
gtgttaacgt tagcgctgaa ctggtcaagg tagctttgct gtagactgtc acgttcgctt    20700
tcactggtac gggctgtgct gacatcatcg gttgagcctt tagtgccagt attggcggat    20760
acgtgcgcac tagaaccaag aaatccactc ccaggtgtgc cgagtttcac ccctgcttct    20820
gctccgacat acattgataa taaggtactt gtggcttggt cttctgtcag gttgaagtcc    20880
ttagcaaaag acttaaccgt actacgcata tctgcgaagc ctttgttatg ggtgccgcta    20940
tcgctggtgg cgctattgct gccataactg ttcgaggtat tgaccccgct catttgactt    21000
agtgcggcat tcttgacggt ggcgaggctt tcgcttgcta gctcactctc aattttgctc    21060
```

```
gcactgatcg cgtttgatcc agattgcgat aaggagtttg agaccacatc gttactgctg    21120
atattcactg gcaagctacg gcttaaagca ttttggccat taatgacttg tctgccatca    21180
tcaaaggtgg tggttttcata gccagttgca tcttgcttgg tgttgccatg aatacgttca    21240
acgccagtgg tgtcgatttt attgccgttg gtgttgttgt agctgtagtt atccacctga    21300
gcgttaccca aattgatatc accacttgcc gcactcgcag aggtgcgcgc gttaacgctg    21360
ctcatcatgc ccgcgaactg atgcgacata ctgctcatta ccgacgcgcc gcctttcata    21420
atgagcggga caattaatgt cggtacgctc atcattaaaa agccggtcat ggccgcatag    21480
cgggagtgca tttcttgtaa gggatcaacg ttgcttaacg tgataccgcc gtaaatgtta    21540
gtgatttcgg tggcgttaag ggataagcgc gtggtcatga tgaagttaat gagggcaaac    21600
atcaccggcc atgtgccaag gtagataaag cctttgaaat agttgccgag cacttgaaac    21660
gtgagtgagg ggatcatggc aatcgccacc actaaaaagg cgacagagct aaacagcaaa    21720
aacaaaatcg attgcagcat gggcaaaaat tcccgcgcct gcagggccat tcccgcccac    21780
atcgatgtgg tttgcatttt gttttgcgta taggcgtagt tgaatgcggc ggcggtgttg    21840
ttgctcaccg ctgcatcatc tgcaaggcca tttcgcaggg cgttaatcgt catgttttgc    21900
agcgtgattt gcgacgcgct ttgactgata ttggcgtatt tttgataacc actgctgatg    21960
ctggtattca aaaagctttg ttggcttgtg gccttttcac cataaatcca actgcccagt    22020
aacttgatgc ttttttgcgct gtctgcttgg aatagctgct tgaggcgcgg aagggcttct    22080
ttgcaggtag gatagtcatt aggacccatt tgaatcgccc gtagtggcga agggttgtga    22140
gtcgctagaa agtcccaaat atccggcgca ctggctaaat ctcgccatgt gtatttatta    22200
ttgagtagca tatctccgcg aatacaactg ctgatgtagt gctgccaata gcctttaagt    22260
tgggtgtttt ctatctcgct ttgtctggat aacttgtaca gctcagagcc aaacatcatg    22320
cccgttttac tgtattgttg atcatccggt acgtgaaaaa tatcttccac cgtttgggtg    22380
gtggcataca tataatgcga tgcccatgag gccggaaatg ccactatcgc gggcacattg    22440
tccacgcgat agttacccgt cggattggtt aaatcggtaa tttgcactgt ggcggtggtg    22500
ttcatggcaa gcaatggcac ggcaaagtaa accgcgcacc atttcataat cgcgttatgg    22560
tcacgcttga tgaaaagtg cagcgcggtg gccaccacgg caaacagtgc acagatgctt    22620
atcatgctgg caaatgaatc ggacttgaac agcacggcaa tggcattcat cacttgcttg    22680
gctacgtcac cgttgctgta cgtgaaaatc tcaaccgcca tggttatcgc tccccaaaat    22740
tcaagttggc cttagcttta gcgctcatgg cgcccgttat ttgctgtttg atttgctggt    22800
tttgcataat gagctggtgc tgtgatatcg cctcattttg agctttagcg gtgagtcctt    22860
ctaaaaagcg gttagcgttg ataatgtctt tctcgatgcg gtcaatgtct ttgggatcat    22920
tgttcgtggc cgtgattgaa gatttcacaa tcgacagcat gttttgcaga tagagggtaa    22980
taaactgcac gctgatgatt ttggcgtaag tattggtttg gggcgtgagt cctgcctcca    23040
attcggtacg taaaaaggtc atgatgggca gtgtggtgta ttcgagcagc gacttgtcgt    23100
tatctgttag tggctggtcg ttttgcatct tgctggcgat acctctgagt aaggtttcta    23160
cgcggtattg caggccgtga ttactttgga tggtgatcgt ttgttgtgtc ggtgctaagc    23220
attggtcaat ggcttgattg gtgcattgat agctttcagc tttgccgccc tctaacagac    23280
tattaatcag gttattgttg tcggtcagca gtgagccata accgcgcgca ttgccggtcg    23340
cgtcatagat atacgtgccc gaaatcgaca tgagaaattc tgccaaggtg ggatcgctgg    23400
```

```
caaggaaggt gttttttaaa atggcggccc acacaatatt ggtgttttg cgcaccatgt      23460
cttttagtgc gggatctttc tttgcgttat cgagctgatt gttagcttga ccgcccgcgc      23520
cgcattcttg ctggccagat acccaatccg caaacgcgtt attttgtgtg cccatagtgg      23580
cacaaatgta tttttgactg ccaacacctg caaccccgc cagtgcagat acgcccgctt      23640
gggcactctc gcaagaattg atcgactgat tgagatactt atcagcaatg ccgttagcg      23700
tgtccttaat ctgtttgatt tgcggtgccc acgtctgcag gctaaatcg actgcgaacg      23760
gtgcagcgtt ggcgataata gccttgcctt gttgcacaag ggcgtcagag ttaatgtggc      23820
tgaatccccc cataaacata tcaataccgc cacagcctgc ggcaatgctg gcatttgca      23880
cactcacgag ctgcgcgtcg cgaatggggc tacgcacaaa gagattgccg ccgctgtagt      23940
agttggcgct ttggcctttg aatgagcccg gattggtcac gttagtgcca tagcctaggc      24000
cattgaaaaa atcgtttagt gaacctgaaa cccccgcgct ataggcgtgt gttgtcagca      24060
aacatgaaat agtgacgccc agtagtgtgc gcgtcagtgc taagcgtttc atgatttacc      24120
tccggtattg ccgtttatgc tgccgcttat gttgccgtta tgacgcgggt ttagtgtgcg      24180
tagcgcacgc aagcaaacgg cacttaacaa tgcatgcact gggacgagta cgaatttata      24240
aatggctaag gccagtaaaa tattgatgat taacatcgtg tccatgagat tgctcctaac      24300
gcatgcttgc aatgacttgt gggtcattga gggattgaag gtaactttgt tgaagctgcg      24360
agggcgtcac atcaccgacg gttaaacgga caaacttacg ggtattgacg ttgattaaaa      24420
atgtggcagg cactgtcacg ctgcgcggat tctcaaagaa ggtggcggca atgtctggcg      24480
tggaaggtat cggtacttca aagcctgcta tgccttggtt gtcgagcgaa aaggcatagg      24540
tataggtgcc agtttgcgcc gcaagctgtt tcagtttcgg ggcgaactgg tggcagtaag      24600
ggcaatcaga gcgaaagaaa aacactaacg cgtaatcatt cggattggcc gcaactgccg      24660
ccccccccat aggcgtcgcc ttagcgctta aagagaatag aagagtcatt aacattactg      24720
tgatgatgcg tttcatgggt attttccgtt taaaagtcag gggcgaaatc ggtggccacg      24780
ttcaggaagc ggccaagtaa atcgtcttga gagataaagc catacgcgag cggtttcatt      24840
tcccccgtgc caggattaac taacacgagt gcgggactaa acgggacgtt tatgtgctgg      24900
tcgttttggc ggttctgcac gatggctggc agtgctacac catcgagcgt gacgccaagt      24960
agctcaatgc catgctcagt agcgaactgc tgcacactgg gcgctagcgc aatatcaatt      25020
tcttcttggc ctttgtagac aaagaacagc ccccatcccg catcggcaag gctgcgtact      25080
gcgcgcatct tcttgttgcg ctctaatgat aaataggtgc ttcttgccgc ttgttccgtc      25140
ggtctatctt tggtgtaaga cagctcaggg ttatctagca ggacctttt aaaggtcatg      25200
ccgaactctg acgatttatt gctgacgtac tgattaagca gcatggccct ttccactttc      25260
ttgctgtctt ggctgtttat cgccgcgtca ttgagcgtgt cttggtagta gctgtgaaac      25320
caatccatct gctctgtggg cgtcagtgtt tgggtgcgcg tgagtgtgac gcttggcgtt      25380
tcggcctttt taggtgcttg cttcttgggg gcggtcggtt cgttatacca gcgccagcct      25440
tgtgcatccg tggcgttcgc gccgaggcaa acgttgtca gcataaggat cactaacgcg      25500
ctgcgcttgt tgaccaccgc atccccttt tttgtggaca accacgccaa cggcgcgtgg      25560
cttgaccacc gaaaaaaagg agatactgcg gcatgttgta agcggtcatt taacaacgtc      25620
atcatggttt ggttcctcca accgactgtt gtaagcgttt ttgaatttca tctgtgttgg      25680
gcagttcgat ggcgtcgtac atgtcttcat aaaaatcaga aaagtccatt gaagacatat      25740
caatgcgttg cagttcgtta ggtgaaaagg cgctgcaatc aggttgttta gcgctgccga      25800
```

```
agtttttgcc caattgcgcg cggccctcaa cctgcacaat gcgcgcgagc ttgctatcaa    25860
acgcgcaata ggcttttttc ttgcggatac acacgccaag cactttctca gcgcaatatt    25920
ggccaagtga tacggtgagc ttgtcttctt tggcggtacc cagcgctttt tcttcttcac    25980
tgcaggacgt taagccgatg ccgttacccc aaccgctgtc ctgacaacaa ttgctgatcc    26040
ccagcgcttt atcgctgcac tccatgatgt tgcctttgaa aatgatggcg ctgttttcgt    26100
tgatgttggc tttgtctttc acatcaccgg ctgcgtcact gacggcggcc agtcctgccg    26160
cagcatggtt aaagtcagtg ctgcgagtgg cagcaggatc gtaatagtca ccactgagcg    26220
caaagctgtc agcaccgcag ataaggcccg tatcgcggca ttgctgttta tcacataggc    26280
gttgttgttt atctttaatg caaacgccgc caagttgggt gtcacaactg gtcgattgaa    26340
tgctgcaatc tgcgatggcg tcgcaggtat tgggaaaggc acattgatag gtggtttgtt    26400
ctttccagca atccaatgtc acggctatcc cattaatcat gcgcgtttct ttaccttcta    26460
cgcattgaga ttggacttgt tggcactcag gaagaacagc accacagctg ttgttgtaac    26520
cgacttcaac atgcgtttca gtggtgatga tagtgatggg taaattctgt aactcaattt    26580
taaagtaaaa atcccaattt gcacttatat gaaccgctaa tggggatgct ttaatatcat    26640
aattttctgt ggttaatgaa ctgtttacac tcattgcgca aggttgatta gcaacacatg    26700
taccaggggc tctctctgtt agaacatgtc ctataaacgt accatttaat gcaattgata    26760
attcggcatc aatggctata gaacgatact cacctttaaa ttgaacacgg acgatcttaa    26820
cattagggtt tggtaatttta atgtcaatag taaacggtgg tgtgccagtt aagctgtatg    26880
aatgcgccac ttccttaacc gatgtgcttt tgacaaaggg tgttaggtag cattgcaccg    26940
gattattggt gggcaacgtg caagaacgtg gcagagaatc gacttcacaa acgagccctt    27000
tttcacagtc atgatattta tgatgaaatgc cgtggctgat attgtaagca tcattttgat    27060
agccaacggc ggtatggtat gccggatcgt tttcatcaat cgtcgggcgg ccattattaa    27120
agccactcgt cacggcttgg gcttggccat ccgtgctcat gccttgcatt ttggcactgt    27180
ccatggcgct cgggttgttg tagtaacggc tttcgcttgg gttagcgact tcttgctgac    27240
atgtcgcatc tttgcatagg ctgttaacgt caaagccggt gtaacccgct tgttctgat    27300 tctgcttgat actgtctttg gcccactgca cattatcgcg gtaatccttt tcgctgttgg    27360
ccgccataac aggcaaggcg cgctcaatg tgaggatggc actgaggatt aaggcattat    27420
tcaactgagt catttcgccc cctttgctaa tgtcttagct gccacatcgg gaatgctgcc    27480
gtgttgtgca agtaagttca gcgcgtcata caacgaaacg ttgccgtaaa tcacgtcaaa    27540
gtcatcggta ctgcagggct gttttgcctg acatttgttg ggtcttacag caacaaaggc    27600
gggtacttgg gtaatgccga attgcgtaaa ccactgggga ttaatcgcaa aaccgctctg    27660 tatggttta cccttgttat cgataaggtg attcatctgt ttaacggtgg ctgtaaagcc    27720
ttgaggcagt acaccgcgca caatgagtgg cacctgtaag tctgcgcttt gcatgagtaa    27780
ctgctgcaaa ctggtcgcag gcatacccaa cgacacaaat accatcacac cattagcatc    27840
ggcgctgggg ttgggctttg catcgagcaa tggtgatagt gcgttgtcta attggccttt    27900
gctttgcgct tcgaactgac gggctttatc aaatagtgcg gcttggtcta cgttcaatgg    27960
gggtaatgtg tgacgttctc gcatcgacag cgcttttaat tcgtcaatac tgtaatccgt    28020
ttgggcgaac acctgtgaaa ttgatccaag gcaccataag ctcacgagca gggctaagcc    28080
tttaaatgaa tgtgaaaata ggctgttatc cacaattttt gtgcataaag cggtatatgt    28140
```

```
tgttggtaat ttggtctcaa actttttcat cgaaaatccc tctccttatt ggtcacaaaa    28200
acacgcaatt gcgttttttg aagttgataa aaccaaagtt gtcacccgac acagggttgt    28260
cgtggccact ttcccagatc accgttgtcg tggtgtaagg gtgcgcccat agcgcatcgg    28320
gtatggtgtt ggtcatttga tagcgatagc gggatttagg catgaggggc atcggcgttt    28380
gatagcaaat cgcgccatct tcaccgtggg attcccatac gatgccttgg cgatgcaatt    28440
tgtagttcag gcgctctaaa atcaacgtac ccgcctgaat tggcgtgtcg cggtaattgg    28500
tggtgccagt caggggggtaa gcactgcctt gtgagcccat acaccaaaac agaaaatcaa    28560
aaggcaatat gctgttagtt gaggtggcca cggcttcggt tgcacaggcg agttgtgaca    28620
cgatattgcc aaataaaatg gcttcgggat tgaggataaa tgacaactcg tcatcatccc    28680
acagtgggtc aatctctgtt aaataggcaa tgtcgaaatt gtccgtggcc atacaagctg    28740
cgctttgcat aatttgcagc caatagatca cagggtattt gtaccagtgc ccatgataaa    28800
acgcgccatc actggcatcg ttatcgcggt tagtgacgcg ccgccgatt tgggggggaat   28860 tactcatgtc gagcttcatg cccatgttga ccatgcagta agggacgcgc gtcacgtcca    28920
ctaaggtatc aggctcccaa tagccaatat tgaggccaat ttgcataaaa attggtggcg    28980
gtttgggaca aaatgaaatg ggtgatacgg ggttgcgcgt atcgggtagg ctcccaggaa    29040
taataggcac actgccaatg gtcatcggga agatacacga ccaacaaatg tcggtcatcg    29100
ggttaacgaa cgtgcccgta caggccgctt gcgcgttgac ttgtgcggga atgactccca    29160
ttaagaatgc taagagcagc gcaggtttaa tgtgtcgcat ggtttgtttc ctccatgaat    29220
acggggaaat ttgacacatc tatttcgcgc acttgccaca tcaccccgc ttgcttaatg    29280 acactcggca cgcgcttaag tgttaatgcg cggctgaggt ttccttgctg gtcaaagtaa    29340
acgcgcgcat ctaattggcc atgcagtgtt tcgggttcgc cgcccgttaa aatccatttg    29400
atggtgtgtg gcttgtcatg ggttgttgca aactcttcgg cccataacac ttgctgcaca    29460 tcatcccccat caaaaaacac cagcgtttta ctgaactcaa acttgccgac gttggccttt    29520
tgcaatgctg gccatgtctt ggtgtcaaat gggtttacgc gcgtcccttt gggataaatc    29580
aggttgccat tagcatcatt gatatctttg gccagcgtta aagtgggatc gactaaaaac    29640
acttctggtg ttttagttgt gataagtccc actggacgag ggcgcttaac accggctttg    29700
acattctctt ggaattgctc gcgcatactg tctagctcac ccgttttttc taaggtttgc    29760
agacggtttt caatccactg cagcatgtca atttcagcta tggggaacac ttggcccacg    29820
gtgccgatgg acgcagcctt gagtggtaag agtgggcata gcgctagcat cagaagcgcg    29880
aatttattca tttagccgtg acctcgttcg cttgggcgcg gttcgccttg ttttgcgctt    29940
gaagggtttg cagtagtgac tgctgaattt cttgggtgac attcacggcg ccactgacga    30000
cggcggggct gactaacacc acgacatggt tatcaatggc gtattgctgc accacatcat    30060
cgagtgtttg ggtaaatcga gtgatttctt tttcgcgttg ttcgtcggat agctcgcttt    30120
gaccgataga ttggtgaaag ctcgccacgg tttcgttaat gtcatactcg acaacactgg    30180
gttcgcgcgt cacccagagg gttatcatga cgcccagcgt caccagccat aaaattgatt    30240
gtatgatggt tttttccatt ttatgcgcc tctttgtggg ttgctgcggc ggacaaaatg    30300
gcatcaaagc gggccatatc atcgggatag aaatgttggg ctgtcagttc aatggcatcg    30360
agtaacggca tgccgccttt aatcaagttt tcgcaatatt caaactcttt gggttcagtt    30420
gagagcatgc cgcgcgacca tggatcggca aaaatccggt gaaaggacac tagcccgccc    30480
gctttgagca tgacgcagga atgacccgca tcattggcgc gggggaatga cttgatcatg    30540
```

```
tgttgctcga agggcgagaa gtggtcagga tgcttgttca agaaatcccc aaagccatca    30600
ccttggcgca atgtgatatg aatatctgaa ctgttcagtg ccgcttcggc ctcggcgttg    30660
gcaaagaagt cgttcatgcc ttgcgttact gtggcaaagc tgccgccgaa cttacgcact    30720
gtgcgataac cttcgttgat gaaatcctta ctttgcgcat tcgcgccgct catgagtgac    30780
catgcttctt caatcacaca gattttcgga atagaacgtt ggcccgataa gtacatttgt    30840
tggctgatcg tcaccatcaa cgcgaaaatc accggacgtt gtagctcgcc tttaaatcca    30900
tcaagttcca gcgtggtgat atcgatattg ggatcgagca tcgagggctt attgaaaatt    30960
gcgccatgaa tgccctgtga gcagaacttg tttaattgcg cggcaatatc actgatacgg    31020
gtatcgtcat tttttgtgc ggcaatgtca tagagtgccg tttgcacatc gtcaatcagc    31080
gtgtcgttac cgcattttg ccatgccagc aaaatagcat cgccgagtaa tgccgtctga    31140
aatccggtga gcttttcatc aggtgatgcc atggtggcga taagcgcggt gatgtttccc    31200
aacacttcgg tgatgggatc aatggcttga ccttcatcat cgaggattgg gccaaaagta    31260
cccgcatccc gcacgcttaa tactttgcct aagtgggtaa acgggtttag gaaaatctgc    31320
gaactgtcga gatagacgcc gcctaatgtt tgagtgagtt ttttataact ctgacccttg    31380
tctaaaatcc atgccttgcc cccttggca aaaatcgatt ttactaaggc ttgcatgaag    31440
aatgacttcc ctgcccctga gccgcccgta atcgccatgt gtagttatc actgccgcag    31500
ttaaacggat cgaaatagct aatttgatgg cgcattgttg gcaagagtag ccctgctgat    31560
aagcgtttgt agtctgcaac aatcggtaag aaattcacca agtttgaggt tttcatcatg    31620
aaacacaggc ccgcttttg gctgtctttc ataaagcctt cgctcattga gaacgggagt    31680
gtggacaggg tgcacatgcc ttgcagttta ttgtttcgga ttaaatcaat gcctgccgtg    31740
cggaaggtcg caatcgcttt tgaggtgtca tggcgttgtt tctcttctgt cgtatacagg    31800
gtgacattca atgtcatggt ggtgatttta aaggcgtgtg agctgagtcc tttttgtatc    31860
tccttgcgtt cagccagttc atccgcggcg ctggggatta acaaccgcat aggggagttg    31920
accgttttcg ttagtgagcc aattttgctg tcgttacggg tggtttgctc gccggttta    31980
ttaatataaa aagacacgct gacacgataa ggacattgaa cactgttcat ggtgtaactg    32040
agtgatgcaa tacagttggg aaacgcatat agcctaaagt cgttcggcag ccccttagc    32100
ccaagattga ttaaggtggt atcgacactg ttgtcggatt gcatcggcgt gtgacggata    32160
ttgaccgaat cacgattaat gatgaactca ctgtcagggc tgagaatttg ggtgttgaga    32220
ggttgatact cgttatattt agcgggcgaa acgcgatctt gttgatgcga aaatttaaa    32280
tgctcgcggc aatgctcaat caaatcgtca gcgcctaagc ggcgaatgtg catgcctgtt    32340
tgcgccagtt ctgactcaac gccaagacgc atatccagca gtgcaggcat gtcctctgtg    32400
gttgaaacaa agaaaaaccc tttggtgttc tttaaatcgt agtggtatgc gctgctgagc    32460
ttggtgccaa agcctttggt cgaactgtgt ttggcataga tagcttcatt attagcaaat    32520
ttatcgcaaa tggcattgcg accactgagc agcgcttgat tttgctcgat gagttcaccg    32580
acttggttgt tacccaccat gacgaattga tagtgccatt tgtcgccctc tggcagtgtg    32640
cacaccaagg cgttcatggt tttgatcaag tcgtcattag ccccgccaaa cagcgaaatg    32700
gcaaagccaa aaccaagcgt attggcattt tcaaatactt gttcggcatc atcataaatg    32760
cgatagggca attcatgatg cagatggttg tgctgctgtt tgctgctggc atagagtgcg    32820
ccgagatcgt ctttaatacg ttgtttcatg gcttaatcct gcttgatgta tttggcaggt    32880
```

```
ctacccgtcc aacggctctt atcgaccacg atgtagacat cgctggtatc aacgtaatca    32940
ccttgctcat tgagatacgg gaagattgtt acttttttgga ctgactcaga ggtgcgcagc    33000
ggtacaccgt ggcggtcgcg gcgtggcaat gggataaagt cttgttgttg gctcgcgagc    33060
ttgggaagtg cagttgtgct ttggccgctt aaggccgtca ccgcagggct ttgtgcttgt    33120
ggctgattga acacaccact gtcggtaagt tgcctcactt ccatcatatt ggtacagcca    33180
ttgatgccgc ccaccttatc gcaggaatag tcaccatcca gccctgctgc acagccactt    33240
aatagccatg aagccagtgc gataataccg gtgttacgta atgcattttt gctcatgatt    33300
gggttcaaaa tgtcactcct taaatgaatt aattcgcacg gccaaaggct gagttaacag    33360
gggggcgttg acccttgttgg ttatattgct gctgtggtgt aggcgtgttt gcgccttggg    33420
cctgcggctt aatattccct ggcatctgtt ctaacagtgg gttgctgata gtgttgagga    33480
tttgcgctgt ggcactgaca ggattttggg cttgttgcgc tagcgcttct tcatattctt    33540
gaatgccaac cggatcgagt gggaagcctt tcaaaaacac gatgttgacg gtattgcccg    33600
gattgagctc aataatcggg tggtattgct cagctaattt gatgtagtaa tcagcaagct    33660
tgctacccac gcttgaactg gcactgccgg ctaagttgag cagtgcatcg gccccattca    33720
cgcttgaagt tgatccaagt gctgagttag atgtggtttg gctcagtgct ttacctgtct    33780
caccaatgcc cgtcaaaatg ccgctaatgc ccgccatttg aacgattttg ccgttcttca    33840
taatggcagt accgcgaatg ccattgcggc catagttaaa tacggtcgcc tcgacgggaa    33900
tgtcgatgat ttcatcttca aaaatacagc tgaggcgagt ggtgcgcaca atgccgcgac    33960
tcgatgagat ttcgccgtaa gccgcgccta aaactgtaca gttgtttagt tttgagggct    34020
tgccgttagg cagtacacct tggttaatgg tttggaatac cattggtacg gtatcgcctt    34080
ggccattcac acccgcattg gcatctgcgc cgccagtaac gacagctgtc acaaatgaac    34140
ctgcaggaac gtagttctca ggggtgcgtt ttttttggcag gttttggtct ggcgtttccc    34200
aatttagtgc aaaggaatcg atgccatttt gggttgcagg tggcgggata gcaccgcctt    34260
gatagggggc agcatacccca ctttgtccgt cacccacgct cgggcgtggt ggtagcgttt    34320
gttcacctaa gtagcgtgtg ctttgcctaa cgggataggc tgatgcatca atgccctctg    34380
tcgaaaattc atcggtgaca ttgctatgct gcattgcatt tgcggtagcg gcattaatct    34440
tatcatcaat tctttcagtg atggtcagtt ggaacgtctc taaattacgt tttaaatcaa    34500
ggcggttagc ttcattgctg cgctcaatgg cttgcatgct gctcagcatt ttatcaatcg    34560
ttttttgttg cttatctaag gcaatttgtt gtgcggtgag cgcagactga ttgtctttct    34620
ctgtgaaatc tttatcaatc acggcaccaa aatcgattgg attgcccgct gcggtttcag    34680
gagcacgttt aggggcagac atataggcgt cgcccgctaa atagagggca ccgagtaccg    34740 tggccccccac ccctgcaatc acccaattgc gttttttatt ggcttcattt aacgcactgc    34800
cttgctcaaa gtcggcttcg gggtcttttt tgaagtagtc taggagttgc ttcattgcat    34860
gctctccccg cctgagacaa caaagaggtg gcctgtttgc tgtggtgcca attcataggt    34920
tgataaggct gcggctcgcg tcgttgggga gtagaactgc gccgttgtga gggtgactgg    34980
gagtgttgcg tgattggtta cgcgataaat gatgccgttg aaatgcttac cagtgaacac    35040
gaaagcaggt tctgttgtca gtcctgctgg tttgggcatt tgctcattta agcgagtaaa    35100
cataaggtca tctattgatg tttctgtgcc tcttggctcg ttatttgttg gttctcgttc    35160 agcagggggca ctaactatat gcacacgata accgtcaatc ggtttgcctg tgttcaggta    35220
acggatcatt tgcgcggtaa actccgtcat catggtgggg taagggggttt tcttatcgaa    35280
```

```
aacggagggt tgttcttctc gataatgttc tgctgtgaag atagaggtca cggcaggaat    35340
ggctttaggg ctgatgaata agccgaaatg tctgcccttt tctgttgata cataggctgt    35400
gaatggcatg gccagattga ggttaacgcg cgctgcgccg gatttatccg atttagtgcc    35460
agtgacaacg caaaatcctt cagggcaatc aatcgaggtg attttgtcac cttcaacgac    35520
taagcggttg atatcgacac tcgacagctc aataggaacc gtttcactgt cattgaatcc    35580
gtagtgtttt gggggcgtat ttgctgctaa cacgctcata ggaaaaagcg cgcaggctgc    35640
gaaaacaagt gggttagcaa tcttcattat ttaacgtcct tttgcacttt cttaatggct    35700
ttgagcgaca gttggccatg gtcataattc atggcaatga tgtagctgat gttttcgggt    35760
tctagcgcgc gtttgcccac atatttgttt aacgtgcccg ttattttac gagacgatca     35820 tcaagggcaa tttgagtttc attgatggtg aagtgactgc tgatgttttg ttttaatca     35880 ttgctgcatc ttcaaccagt aaaggttgca tctgatgcca atcagcttca tcgatatagt    35940
ttgcgagctg tttgtactga tggtctaccg aagcgggcgt gacattgagc tttagaaagg    36000
caaagtattc cgacatctgc tgtaaatacg gttcgtctat agacgtgtct gatacggtaa    36060
aggctgcgct gatggtcggt ggcacaacgg tgcggctttt attgaagtag gccttccata    36120
caatacttgc taggaccgtg ttactgatca tggctacggt aaagccgatt aacagaagtg    36180
tgttgaggga ttttgcaatg cggataaagt cgatcttgtt cttttgtaac atggggcatc    36240
cttaggggga ttggcccct aattcacatc atttaacgta accagtagcg gcgacatgcc     36300
gcaggcgttc gttttaaaaa tgaagcgcta aattctgctg gggcgtacca ataagcggtg    36360
aggcgtaata cgctcatgcc gtattgcgat ttcattctgc gcatccctaa aaaccatgaa    36420
gaggcaagcg caatgccaat gagcgcttga ttcatcatga ataacacgac aaaaaacact    36480
aaggcaggag caagttcatc catcgcgaac cctaatagcg tagggtgtt attaaggtgt      36540 ttagggatgc taaaaaactg agtgggatta tccacggcct atagacctac aaccttcatt    36600
ccaacgttga cgaaaatgac gccaacgata aagccgccga tagccccgcc ccagtttttg    36660
gtcagaaagc ccccgaccgc ggcggcacat aaacctacgg cgagaatggc gaactgtgca    36720
gttgagccgg tgccaacggt atcaacaatt tcagatttag ccggtgcaaa aggatcagca    36780
gcatgtacat cccaagacaa cagcaaagta gcgacgacac aaatgatgaa taggaaagtg    36840
cagcgcatta tgaatatggt gctatcactg ggtatatgtt ttgcgagtct taggatctct    36900
gcgtttactt cagtttgttg tgcgctaggt tgttttgag tcagagttgt catataacac     36960
ttcctttgta tatatttagg tgagacttat gtaattaatt gtaattactc gtttaatcat    37020
tgttgcttaa ttggtttggg cggagcatca acaaaactta ataaactatg ttcaattcga    37080
agctgtattt cggctcgttt gctacgtgct gaacgttcac atgaattaac taatttattg    37140
tgatattcac ctgttagaat aattgttatt cttgagtggt ttttgttaat ttttccatcg    37200
gacatgtaat cctcatttat atctggttgt gcgactatcg cggcgaagat aataagtgaa    37260
aacagatacc gttattagtt aggaaattcc taacttgaaa tgaaacttaa attgagttac    37320
gtaatacttg tattaatagt ttatttaaaa agatagttct aatttcatta gatgacgtgc    37380
atccaaattc tgctctgaga tcggcaaggt gcctttcaat tgccgtgcgt gagcagtctg    37440
ctttggcttg taattgagat ggtgtcattc ctagtgaaaa atccttcatt acttctagct    37500
gccgttgcgt aagagttggg aacaactcac ggaaaatagt gatctcgctt ttatttagag    37560
gcatattttt ttacttcttt attgaaaaat cgatatgttc tatcatgaat aaaattacaa    37620
```

```
gattactgta ttacagtaaa cttactgtat tacagtaggg tggtcaatac aaaatgaatt   37680
attatgaaaa aaaattataa ccctcctact tcgtctaaaa ctgagcttgt gacgtttagg   37740
tgcccaaaga agcttaagga attgatggac caagctgtaa aagatggtaa atatcaaaca   37800
attacagctt taactgttga ggctgttaag gataaattgc aattcgaccc cgattcagat   37860
gcatagttga tctgttttgc attggccttg caattttttt gatgagctat taaaatacga   37920
agtagatttt gaagcaaaag tgcattacat agcacgctac tacatagttt tctatgtagt   37980 gtattttca aaattagagt gtgttggggg tggttccctg acgtgaagca ttcgacaaca   38040
aagccgactt accgaatggg tcggcttttt tgtgcctaaa attcaagaca ttgaaagatc   38100
attgatcttt gcgatcgatc atattatagt gtttggcaat gtttgaacta accattcaaa   38160
cagccctaaa acattcggaa tcaacaataa tgcctaattt cttaaatggc tgctatttgc   38220
agcacaagat ccatatcctc agatacatat accctctatg ccgccagatc tcgcgatcta   38280
tgctgagcta cagtgggata gtgtctgatg caaaactcta gtcaatcaga tcttctctat   38340
tcatcattca gcagtgatga ttatcaagaa catcctcctt tatctagtta tgctgatata   38400
cctcatgttc atatggcaga actgccagat ggcaatgctt actctgtcga tgaagaagcg   38460
attaggttaa aagttgctag aaaagctgag cgtgacaaga tcaatgccga aattaagagc   38520
cttgctaaca tcgtcaagaa aaaaggtgta gctgttggct ttaaagcaaa agtagcatct   38580
tatgctggat ttaaagctaa gcgactacct gattttgtgc aaacgttatt aacccaatct   38640
aaactattgc ctcaccgcga cgattttta gatcgtggtg atggattgtg tagaggaaaa   38700
actcaggcac gttctaaagt gattttaggc tatatgctct ctgcatttgt tgttaactgt   38760
aatgtcaaca acggtcatat tgtcgttgct actagacatg gcggcaagaa cgttactcat   38820
gatgaactac gtaaagaagt ggccatgcgt cacggtgtct ataccagaa atcaacatgg   38880 tacttttacg ttaatcgatt agttcaatgc ggccacattg aaagccatac tgtgagcatt   38940
tatgaagatg ccacgtagc ctcttttcat gctgaagcga gccataagta tttatcaaca   39000
aagcttatgt caatgttggg tgctgaccga ttatctgtaa aacagcagc tgcgaagcat   39060 aacgttgatc tgaaactggc aggaaaatca tttaagcaaa aaccccgcta cgcgagttcg   39120
cgctatcgtc gcgatggttc tcttcgtcaa aatatgccaa tcataaaaccc gtctcaagaa   39180 ttgttggcac ttattcgctc tcactatgaa cgcgaagctt actacgtacc tcccaattga   39240
cattctaagc cttttaatt cttcgactat caatcagtac attactgatg cttctcatgt   39300
cccaatgtcc aataagcccc tcataccct aatttattag gagtatctcc atcaattctt   39360
aatattactt agccaaattg gattggattg atcttatttt atgtatagcc atactttctt   39420
tttaataaac ttaaagtaca aaaaaaactg caaagttagt tgtgatcttt agtctcacct   39480
cttttgattt tttcttttga ttttagctt tagaaaatga aagataaaaa gatctatagc   39540
aaaagatata aaatgatga ctgataaatc agtcgcttct acaagagatt aagagaagcg   39600
ctgcaagtta atttttgtctt cgaccgttaa actacaaacg tgctgtaact cagttgctaa   39660
agaaaaaagc gtctagcagg actagtttgc aagctcaatg ccaaggtaca taaatagaat   39720
ggttaaacca ttctattgag aaagtcattt gttaaagtaa tcccctcaga tattcaacga   39780
tccactttat agttaacgct tagagaaaga tcaaaaacac cgctaacacc tccttttgtc   39840
atccgaccgt ttaacaacaa acgcgctggc caatcgttaa aaaccaaaaa acggtcttgc   39900
agggaaagaa atttcaaaca ctgtgccatt aacaatcgta cggttttagt acggctaaat   39960
ttgactaaaa tatcatttag acgtactatg tacggagttt tacataaaga taaaacacaa   40020
```

```
cagagtttgc tcgcagcaag taatgaggta ctaaaaaatg gaaatttga ataattttaa   40080 tgaattagac aaatttattg tcttagattg ttattaagga ggttacaact taaaaaattt   40140
gatccaatga ggaattcgat atgagtattc aaaatacggc aaatgctgga gccgtttcaa   40200
aaccagcgcg gatagaactt aaaacctcgc tagaggtaaa ggaactgctt gaacgagcgg   40260
cagctatcaa tggcatcaat cttacggcat ttatcattaa tcaagcccga gagagagccc   40320
atgcaattat tgaatcagaa actacactac atctgaacca acatgcttgg actcaatttg   40380
aaaccatttt agataatcct cgtaaagcta ctccggcact aaaggcacta ttttcggagt   40440
aaaataaatg agcacaagcg atgttgatta tcagctgcta aacaagatgg aacgacaacc   40500 aagttttca aattttgatt gtggtgatct gtttcttgat agttttgcgc ctaagaaatt    40560
ggcgaaagct gatgctaata atgattctcg ggtctatgtt gctgtagaca gagatatagg   40620
tgttggattt gcaacgatga aagttttat gctcagtaat gacgagcatt caattttatc    40680
tgggaaatat ccacgccagg ttcctgtggt aatgttagat caaattgcag ttgataaagc   40740
ttaccaaggc aaggaattg gtaaacgcct gatgcggaaa gtgatggaag ctacggtgtt    40800
agttaatgag cttgctgccg cgaagggttt agcgttatgg gctcacccta gagctaaaga   40860
tttttatata tcgttagggt ttgatgccat tcctgatgca accaaacaag tgcaagacgt   40920
tgaattagct ttaatgttta ttcatgttga aaccattttg gatgcattga agtaactaag   40980
agttatcaag aaacggatta ccaccactaa acccgcttg cggggttttt atttggggtt    41040
ctgtgccgga accgccgaac gccaaaactt atgcctcacg gaaatttcgg cggttccgac   41100
gtacaccccc taaaagcagt gctgtaagtt aattttgtct acgaccgtta aaattcaaac   41160
gcgctgtata gtcagtcgct aaagaaaaag cgtctagcag aagggatttg taagctaagt   41220
gccaaagtgg cgaagaaacg gagtaaaact gagattttca aaagcaaaag agttgatcta   41280
tataaaatgg ttgaaccatt ttattgtaag ttcacttgag tatgagccaa gtaagtaaga   41340
aagaaaggtt aaaaattgag aaaggtattt agacctggca ttaaagagca ggaacttaat   41400
ccctgctctc tatggtttat tgttgaagtg ttagttgttt aaatactcgc tgttgtaacc   41460
aatcaggttt cgttactaac cattgaatca acaatcccga tgggatcatt ggtaagtcaa   41520
ttagacgcgc tttttcaatt tggttatact gaaattgtga cataagttta gttaccttta   41580
tcctaggttg tggcacaggc cagtgatgat cttgaccatc atcattggcc gtattttat    41640 ccgtcatttc tcatttcaat accctcaact tccgtatttc gttgtttggc cacattaaca   41700
gtctgaccaa attcgggttc ttttacctt aaaaatagcaa ttccattgaa tataagtata    41760
caccttaaat attaaggtat acacttaaat ttaattattt aaggaggatt tcatggatag   41820
catgcagact acagagactt ttcaagagct taaaatgggg gctgatgcct atattaagcg   41880
acgtaaccaa cggttattgt ctaatcaccg gaaagagttg cgaaaattta cgcgtgcgga   41940
agcctttacc tatttggaca ttgacgcaaa aacacttgat aaatatgtat ctacagcaga   42000
ttttgatcca aggcggcatg aagattctca atggctaatc aacatagaag aaatgtataa   42060
attacgagat ttgctaccag ataatttgcg caaagcatct aaatttaagc gcagtgataa   42120
ccagaaaatg caggttattg ttatacaaaa tcaaaaaggt ggtgttggta aaaccgtttc   42180
tgctgcaaca attgcttcag gcttggctac agagtttcat caagagtatc gggtaggcct   42240
tatcgatatg gatggtcaag ctactttgtc catgtattac gcaccagaag cggatctaga   42300
aggttgttta tctgttggcg atctcatgat gaataatttt gatctagatg aaggtgagac   42360
```

```
tcttgaacaa gtcgtttcaa acgcattctt acctacaact atacctaatc tccgtatttt   42420
gccggcatca caaagtgata gagctattga aggttggttt catgaacaag tatttggtca   42480
aaagttaaag tctccttact ctcttttgaa cacgatcatc aatgctgttc aagatgaatt   42540
tgatatcatc attatcgata cccctccctc attagggtat gcaacttata atgcatattt   42600
tgccgctacc agtgtagttt tcccgttgtc catcacagaa aacgacattg atgctacttg   42660
ttcctatttt agttatatcc ctcaagtgtg ggctttattg gcgaatgcta atcatcgtgg   42720
ttatgatttt atgaagattt taattacaaa tcatcgcgat agcgctacaa caaccgatct   42780
aatgaatagt ttatacgatc attttgcgcc ttatatgtac tcaaatgaat ttaaacatag   42840
tgaagctatt cgtcagtcat cttcgttgct ttctaccgtg tttgatatgt ctaagagtga   42900 atacctaag agtaaagcga cgttccaaag tgcacagcaa aattgttatg aagtaaccag   42960
ccaagtccta agagatattg tgaacgtctg gcgtgaacag gagcaagcat aatggctaaa   43020
aaacgtgggg taatgagccc tctaggtaat gctgttggtg ccgaagaagc acaaataaat   43080
gcagccaaag ctaatattga gtcttttaaaa cgccaaatta caactgaaat tgaaaaagta   43140
agtgaagacg taacgttatc tcttcaaaat ttatttggtt ttgaatctgt aggtaaaagc   43200
ttcttatggc aattagcttc tggtgctacc gctacattta ccgaagcaac attatcatat   43260
gaacaagttc gcgatagtac ctatgtgact ttcgatgtta acgggcgtga ccaggcatta   43320
ttaaatgcag attctctaca agatctcgat tcattagctt tccagcaatt ttacccagca   43380
gtcgctagag aagtgaatgg taaactcgat gtgctagatg gttctcgacg cagagcttgg   43440
tttttactgc aaaatggtga agttgatata tttcgcatac tggtaactaa agatgatatt   43500
tcactttcag atgctaaagc tctagctaaa cagctccaaa ctgcaaaaga acataaccta   43560
cgtgaaattg gccaacaatg tttatctttg gaaaaagcga atcctaagat tacacaggct   43620
gaagtagctg ctcaacttgg aatgagtcag gctggtgtga gtaaagcttt aaaagccgct   43680
aaggtcgatg aacgtttggt gaagcttttt cctgtggcta atgacttgtc acacactgac   43740
tatgctttgc tgagtaaagt tatggaagtc tatgaatttg aagatgaatt actatcattc   43800
atcaatggtt tgactaaaca agttgtcatt attcaggctg aatattcaag ggaagaacgt   43860
aaatcagcta tcaccaaagc gataaaagca gaacttcaga tcgctaagga tatgaaaagt   43920
aaagcacagg ttagtgttac taatcttgcg acatttgata gctcaggcat ttacgcaaga   43980
aagcgtatta aaggacgcaa cttcgcttat gaatttggtc gactgtcttt agatattcaa   44040
ctgcagttag atgttgctat tgcagatgtt ttgaaaaaaa taaatttaac acaaaatcag   44100
atttttaaaa aatttagttt tatgtcactg caattaaatt atttctccga ttgtggtact   44160
acatactaaa acgccttagt tacaccttaa atattgccta tttataacag tagataactc   44220
aggactatct actgttatct atctatttgc tgtatatgac ttcggttcga ggtgtacata   44280
tgagctataa acaatcgaaa ttttcagtg gtggatattt ccaaaatccc agcgacccct   44340
caaacccaca taaataccct aacttgttta ataaatccac ttatgacaat atatctatct   44400
gatatttata tattttacta agggtccttg gtgttttatg aaagaagttt taatgctat   44460 tcgagacctg ttagttgttt ttttgcggta tgccttaaga tgcgtgctct ttaaacgaga   44520
ttttgctgac cataatgcag tacctgattt agccccggtt atttgtgaga agggtcatga   44580
acattacgcg caacagttgg aagtatatct gagccgagcg gaacgggtaa aagggattgc   44640
tgtaaccggt ccttacgcta gtggcaagag tacgtttctc aatacatatc aggttcacca   44700
ccctgaactc aagtacatta atatctcttt agctaatttc tatgatgagg atattaaaac   44760
```

```
agttggtgaa aacacattat tagatgctca acaacggccg acagttgaac gcattgaacg   44820
tgcagtatta aagcagttat tatatagaga aagtgacata gagagccgag gctctcgctt   44880
tgtccgtgca cctttaacta acccatctag accattcgca atcgctgtca cgtttactat   44940
aacgatattt gggattgcat tgttgtttgc gaacctttat ggcacaaaaa agatattaga   45000
ttgggctcaa ataaactcaa ccaattttac tgattcaacc caccctttat attggtttgc   45060
agctttcatg gtcgcagtgc caactttatt acttgctgat ttggttcgtt atgttagaca   45120
gatacgaata agtaagataa atcctgttag tggtgatata gaggtacagg gtaaaagtca   45180
tgactctgtg ttcaatctat accttgaaga tattttggct tacttcggcc atgctaaaat   45240
tgatgtggtt atatttgaag atttagatcg ctttgagtgc catagaattt ttgaacggct   45300
tagagaatta aataaagtac tcaacgatag taatgttgtc agtcggcccg tccgttttat   45360
ctatgctctt tctgatgatg tatttgaggg tcctgatcgg actaagtttt ttgatgcgat   45420
tgttccaatc cttcctgtgg ttgcgggggc taatgcctac ccacaattca aacaattact   45480
ggccaaagct agtatcacta tcgcagacaa tacaagtcat tgggatgatc tgtgccgaac   45540
tatcacgcta tatattcagg agatgaggct tcttaaaagc attgtggcgg agttttatt   45600 gtacagaaaa gtgcttgaac tcaataacac ccaaggcagc gaaacaaaat tattggcgtt   45660
tatcgcgtat aagaatttgt atagtgatga ttttgcttta tgccaagaag gtaaaggctc   45720
gcttgttgaa caaatacaac aaaagaaaaa ttttataact ctagagcacc aaatgcttga   45780
aaagcaaata ttagagcttc gtcaagaaga gaaagaggcc gaggcagatc atttggctga   45840
tcaaggtgaa ttggctgagt tgatgttata tagagtgaat tcatctaaag tcactggagc   45900
tgattcttct tatcatccgc ttctctctat tgatagtatt ccctatatg gtgttgaaaa   45960 tcctgtggag gtggttgaaa gaatgtttaa cgcgacctgc agcgagtcat cgtacggaag   46020
cgttaatgga ataacaagga atgggggtc tcatggtagc ctcagaaaat ggtcagctat   46080
gcttgagtcg gcaatgcctg attatcaaac acgtctagcg cggttgaaaa atcgcaatat   46140
agaagctcgt caagcgcggc agaaaaaaat aaaacaacta caacaggaac aacaggcttt   46200
gagtttgcta agcctagcac aatgcctaaa gcggcctctc aaccaggcga cacctacgcc   46260
atcgaatgac aagccaatgc ttcacgcatt tctcatagca ggatttatcg atgaggatta   46320
cggcttctac ttgagtgccc atgttgaagg gcatcttact aaacaagata tggaattatt   46380
aagagcattg aaggggctga cagtattcga ccaaaattat gaatctggca actataaaga   46440
gctggtagca tttatcaatg gggaagcatg tgcttctcct gcggcatata acatcggact   46500
gatagagtat ctgtcagact cgcaaaattc tgatgctatg cctttttttca ttgagatttt   46560 gaaaaatcaa tttaaagacc actcacaggg gcttgagcga ttagctcaac ctatctggag   46620
taaagtatgc tttaaatctc ttattaagca ttggcctgaa gtgttatcaa cattgcaaaa   46680
taatcaagtg ttaacaacaa gcgagactgc agtattactc gttagaatac tacttactat   46740
tgaggaagta agagaagatg agtcattttt cattcagtca ataattgatg cctgtgctga   46800
tatgcttgaa atagtcgcag atagtggcaa tgtatctaag gctctaaagt taatagcaga   46860
agccgatatt aaaatcgaaa ctgtgaatat tttacctaac ttatatgtgg tcattcgaga   46920
ggcactgaac tatcaagtgc taaagctgaa ctcagtaacg tttatcgcca caatatcagc   46980
aataagagat aaagacatca tcactttttcc tgttgcatat actaaattac caattaccaa   47040
caaagccttt aaatcatttc tatattcaga tattcatgag tatgcaagat taatctattg   47100
```

```
tggtgaaatt tccgaagtgc cagcaacagt tatagcttcg ctattgaacg atgagtttaa   47160
atctattttg actgagaaag agaagctttc tctgattgag gggctagact ttctgattga   47220
ggatctcaat attatggacc ttggtaattg caagttgata gccttagccg aagagtttcg   47280
aattgcgcct acttggtcta acgtagctgt gttaataaat ttctataaca acgttctaaa   47340
tgataaaaaa atagataaaa agcataacga aagcactgat gagttaaaag tcatggtgct   47400 gaattttta caagcacaga gtacaaaaga tgcattatgc tacaaaggtg agaagttaga   47460
acttgaatcg gtacgcgatg agtttatttc atttatcgaa tctagtgaga taaacgcgga   47520
tagttttgct gaatatatag ctgcggtaga gtatcaatat ggtcctgata atatttatgg   47580
tttgcgtgag gatcaatcct ccatattgtt aaagagagga ttacttttac catcatttga   47640
gctttatcag gcgctaagag ctgaccagca aaataatact gctttagctt tgatacagat   47700
gaacgaatca atattcttta aacttaatat tatggaagtg gatggttctt ggttaccaga   47760
gttggagttt tcgtctgagg atttgttgaa attgatcgtc agtgattctc tttcggtaat   47820
agcaaaacaa gcgttattaa aaactcatca agtaaatatt tataaagata ttgccccgaa   47880
agaatggtta cacttggttt tacctattca aaagcaagaa aaaatatacg gactgactct   47940
gataaaaaat tcagttctga ctgagcaaat tgctattgat ttaggcttga ttcctgagca   48000
gttactattg gaagacgatg ttataaaagc attgcttgca atgaagtcaa tttcttcgga   48060
tgacaaagta cgtttattga tagggcaaat ggctcatcag aaagcgaaaa tcttgccaat   48120
gatcaattcg tgggactcga agccagatag tttctatacc actagtgatg aatattgaa   48180 tggattgcta gataataata ccaattacgc tttcagttgt tctttggttt accatgaagt   48240
cgtatcttct tgctctgtca ggcgtggacg actacatatc aattacttta agggttagtt   48300 ttattttca gccactcttc aacgatgact aggttattaa aaccgttcac tcgtaatagt   48360
attgttagtt taaagtagga aaatatcgtg gttatacaag aacaagcatt gagtaaatta   48420
gcgaatgcca tgaggatata tggcgaagct catatgaatt ttaatcgttt gaagttagtt   48480
gatgccgaag aggctattga taacttagat cgagctatgg aagccaagct tgaagctttc   48540
catagtctat atgatgtaac aaagggcctc tttgattact ttgaccatgc ggatacagca   48600
attctcattt tactgagaaa tgcagttcac caccgtaacc atctgttgtt taaaacttgg   48660
aatcaagaga tgggtttaaa tgaagggcac aaaaaatacc ttggtggtga gttttgctt   48720 gcaagtcacg acattttgac taatggtcat gaaatgaagc atttgtacaa gcttgaagat   48780
ttctatctgc gaatagaccc atcactaggg tcaccttatg tcgaggatag aattagtgac   48840
aaaagtcgag aaaaattgtt aaatcagctc gaaaatgatc ttagttttgg tgcgcttaaa   48900
aaatactcaa acagtgaaag atacccgcta aaacatgtgt atataaatat aattcctatt   48960
tatatttcag ctactgttaa ggttttcaaa gcacttaacg aaaagggtgt aaagtttgtt   49020
ggttttgacg caaatgcata caagaagct tttacaaatg aactagctgt agatttgggc   49080
tcgtttaatt attcgacaat acggatattg taattaaagt aacaactgtt taagagtgat   49140
tatcaatgca aagcattttc actattctat ctatggtatt cgggtggatt gcgttgctca   49200
cgtcttaaca ggcagttagc tttcttatat taaatggtgc tatttatgaa atttttgaa   49260 gcaggagttc aatataaaga tcttgatggt tctgtccatg cagaccgaga tgataatcag   49320
gatgcaactt attatctaag aaaacaccac agcattcctg ataatagctt cgtgcttggt   49380
attcaagttt attcgtctgt acataatgtt agatataata cccttacagt taggtttttt   49440
cattcaaatg ttggtagtta tgacaatatc caagaaaaga taaaaactga aggcgatgct   49500
```

```
ttggttctaa acgaagttga aattgaaatg ccttacaatg attttttag tctgtttaag    49560
cgctttagtt taactttatc atctaatggt ttactcgaag gcaagtcata taccacaata    49620
taaaagctaa caaggcgtta tgcctatctt ggagactatc gtgaataatg agcaacgtct    49680
aagaattggg tactaccgtt cctctgattt aaacgatggg aaaatagatt ttggtatctt    49740
aaatgcagat ttttctttag attcctatag agagctttat cgcaactcga aggtgattct    49800
tgatttacag ccaatagcaa ttttgttcga agctgttcaa attaatttca acgaattaaa    49860
ttctagtttt aatattggga ttaactttac gaagaatatg aaacctggta aggggttgt     49920
ttttcaatat ctttcattga tgagtgattt gtctgtaaaa attacaaatt ttataacctc    49980
agcgaataca tttcttgtca actcggaatg caatcttaaa aagacatctg agcattttga    50040
atggaatgaa tatcgaaata aactacataa atcctcattt tcttacagat tcacttatga    50100
gttaagaaac tattcgcaac atcatagttt gccaatatca tcgctaaatg tgaaccaaga    50160
taagacgaaa gataaaataa ccttgcttgt aaacatgaaa agagatgagt tacttagttg    50220
tggttataaa tggggtaaaa ttaaaaatga catccaaagt tgtgacgagg tcttcgatct    50280
ttatcctcat ttaaataaat atatgaaaat tatagaggag ttattctcta agtatataga    50340
cgttaagagt gctaaactgc aagaaacaat catctatttt gcaaaactaa atagcacttt    50400
taagttccct gaaaaaagtg ttcctgtagt ttttgttggt gaagccgaaa atgacaaacc    50460
tgtacctaaa catcatgaaa tgataccatt tgaaaattta gattggttat aagtatttg     50520
taataaggta ggttcattat cctgatgaac agttctaaag ggaaaattta ccgtttgcca    50580
ttttcactta gttaaatgtt atcgctaacg ttaaatttat cattaactgg ttcgttaggt    50640
ttctaggaag tattatgtat ctattagaca gatcaaagtt gaagctcgga gacatcattc    50700
tcactcgctc gaatgaaaag aacagctcat taatttgtaa gattactaat tcaaatttct    50760
cacatgctat tttgtatgtt ggtgaatcga gctatattca ttctgatctc tatggggtgc    50820
attctagtaa tactcagcga ttactaatag atgagcttca atatgtaaaa gttatgcgag    50880
tggacgatcc cgttgtagca gaaaaagcca taatttatgc gcggctacaa gttgaactt     50940
cctattcaaa ggttagtgct gctaatgcgt tcgttaaagt ttttacaaaa ctagattcga    51000
aaaggcagtt tgttctagt ttggtcgcaa aagcttttga gtcggcaggt gtcaaacttg     51060
ttgcaaacag tgatgcgtgt ttaccgcaag aaatcgctga ttctatgttt gtaaaagaag    51120
ttaaaggttg tgtgtatcaa gctgaaccga tgaaattga cttttgctaat agctatgatc    51180
ctatcaagaa tcaagctgaa attacaaaca acatactcaa atctgctaga aaaatgttag    51240
gtaacaaaat ccaatcactt tcagatatta ctaaagctct tatagcggac cctaaatacg    51300
atagcgaaat cactgatatt tatgagtcct ctggatactt aaccatgtgg gaatacgagc    51360
taaaagcaaa cccatggcga tataacattg acttatttga ggctttacca ttgtcaaaaa    51420
gtgaacaata tgtactagct acacaagagt tgaaaaatgc tgatgggcta cttgagttgt    51480
acaagattaa ctttgaacaa tacttttata tcaaagagtt acaccgtttg aaatatgcca    51540
accaacaata tatcttatac aaaaaattag ttgaaaatgc tcttgaccat aagtttacag    51600
ccgaagcaat tctcgggaaa tagaccatac aaagtgttcc aacaccgttc cggcgcttcg    51660
cgcctccact cgacagtttg taagtagcgc atttagcgaa ttgctgccca aggtttatcg    51720
caatgtgcta cttacaaact gcggttgaac acaacgttat acatcacatg gagtcaactt    51780
atgtcctatg aatgggtaaa ggatttaatg ccactggctg gtgttggttt aggtgtctat    51840
```

| | |
|---|---|
| ctagttcctt atatcgaaag tagaaagtca aagtcagagt caaaagagc tattgattgt | 51900 |
| ttttatgctg agttggctga ttatgaaaag gcagcatcct catacgtaaa aaattattat | 51960 |
| gaatcatact ggatactttg gaaggctgat aaaggtcaaa agtttaatga tcgtttttat | 52020 |
| gagcttaccc tagctcctcg tctagaattc ttatctttgg aaaccttgct tagcaagtct | 52080 |
| ttgctagagc tgtctagcga tcaaagaatg gctgttaaag cactaaagtc tcttgcagat | 52140 |
| aaaattaata aaaattcaga cctgattggg caagcgaaga gtgcggaaga ttttgtgctc | 52200 |
| ctaattggaa aatttagagc aaatacagaa atgttagctt catttactta tttggttagt | 52260 |
| cgtatgcatc atgaagctga tcggtttgct tatctagatc taacaaatag tgaggtagtg | 52320 |
| aaaaaggtca atggagttct tggcatttcg ttcgaatggg aggatctagc gaaagccaat | 52380 |
| gtataacaaa ttgctgcacg ctgacacata ctgctacgct aattttgtg ttttcgctgc | 52440 |
| gctccatttt atacaaaagc actctccgca gcatgtgcag gtgagaaaga cgttgtcaaa | 52500 |
| aatgaaccag tgaatcactc tacaccagac tgattttcac cccgtatctt ccttccaacg | 52560 |
| gggctttttt tgccttagaa tgaatcaaat ctttagagaa ttgattcatc ggtttttagc | 52620 |
| tcattcaact tagcagcctt ggcaatggta gaacgactgc atttaagcag actctgcact | 52680 |
| tgtgaccagc ttttcccttc atcgagtagt aaccgaatat tgtgcctcaa tccatggtta | 52740 |
| ggctgacgcc caaggtattt acctaaggtt ttggcctttt cgatgccttg tgcttgtcgc | 52800 |
| tttcttcttg tctcgtaatc atctctggcc atggccgcgg ctaaatcaat catgaactca | 52860 |
| gtcagtacct ttgcgatcat ggtatgttct tcagtgttat ttaagatccc atgtgtcatt | 52920 |
| ggctggtcaa caacaacaat atgaatatag gcttttacca atttactttt taggaccttc | 52980 |
| cattgctcaa aggggaggcg agacaatcta tcgacttttt ctatgagtaa aacatcacca | 53040 |
| gggtgagagt ccatgattaa gcgcccaagt tcaggccgtt caattttcgc ccctgattgc | 53100 |
| gtctcagtat aaaaactggc tatgcgaaca ttttttacttt ctgaaaactg aaccaactca | 53160 |
| tttctggctc gattggcatc ttgttcatct gttgatgcgc gtaggtaggc ccgaataaac | 53220 |
| attttgcctc atttggtgtt tttaggatgt ggtttacgat gctagtgcga gtagggtttt | 53280 |
| aaatcaatat atagcgaacc aattggcaat gtgatgtggt tagtttgctt ggggtatacc | 53340 |
| ctaaatggtg gttcgtctag tggtatcctt gtgtatagat atactaatag cgacctactt | 53400 |
| cggatatgag caacgtgaca ctactcaagt tgtcgatacc tgcatactct tgagctcttt | 53460 |
| cttgtggaaa ccttacgatc atacttgccg caatgagaga gtaaataact ctttcaggag | 53520 |
| tatagaagct gtacttagat tatccccgat cagcgataaa cacgtgaaca tgctggggca | 53580 |
| ttattcgttt acccttattg aacaagtact aagtgggcaa ctcaggccgc agaagcaacc | 53640 |
| atcagagcag aacgaattga cttagcgtac gttttgttcc gttggacttc acactcctga | 53700 |
| agcaaggctt aaccagtata aatatgctac gctacgccaa aaagtggcgc acttacttaa | 53760 |
| ggtgttatgt gcaatcaatc agaggtatcg tattttgact gaaatgaaaa ccttagttct | 53820 |
| tttttaatta ctgctttggc agagattgtt ggttgttatt taccatacct ttggttgcgt | 53880 |
| gagggaaaat cgatttggtt gctgattccg gccgccatta gtcttgctgt gtttgcttgg | 53940 |
| ttgttatcct tacatccaac agcagcaggc agagtttatg ccgcttatgg tggtgttat | 54000 |
| atttttatgg ctattttgtg gctgtgggta gtagatggaa tcaaaccaac aacctgggat | 54060 |
| tttgttggct caggcgtggc aattttgggt atggtaatta tcattttgc accacgcacg | 54120 |
| tagtacataa taagttgttt aattttgttc cgcccacaaa aatcgtagcc agaactggac | 54180 |
| tggctacgct gcgccagcca attagcaaag cgttacctat agatattttt cgccactaga | 54240 |

```
tctgaacatc taacaatttg tattccagag taatttagcg ttgttcagtt tcgattgtaa   54300
tcagtaccaa ttaagcatta gttttcatag ttagaaagca aacttagaaa tattttcaaa   54360
gagttcattg tttatcaaca acagagaatt gacattcaat acttgaattt agaatcttgt   54420
gttcagtcaa taaaatagat gtcactttgc gttattcacc aacgttttt tagctcgatt    54480 attttatact tatcactgat ttagccactg tagagttaag ggatgtcagt aatgaaacaa   54540
cgcatcatat taaaagctaa tattttcaaa gctctggggc atccaacgcg attatggatg   54600
gtagagcaac taacaaaggg tgaaaaatgt gtatgtgaat tgttgaggg cgttgatgtt    54660 gattttccca caatttctaa gcacttatcc gttttgcgcc atgctggaat tgtggatatg   54720
gaaaaacgag gtaagcagat ttttttatcgt ctcaccatgc catgcttact gacatcgtta  54780
cattgcattg atggtttatt agatcaacaa attcagaagc agatcgcatt aatggagtag   54840
tttcagactt atcatttggt taaatggcaa ataacgaag taaccaagtg aggctaaatt    54900
atggatatta aaattctcgg tacgggttgt acaaagtgtc aaaaattggc agaggctact   54960
aatgccgcgg cgcaagcact taatcttgat taccagctaa ctaaagtgac tgatattgag   55020
aaaattatgg cctacaacgt aatgtcgaca ccggcgttgg tggtcgacga gcaaataaag   55080
ctgatgggac gacttgccag tgttgatgaa ctcatgacct tgcttcaagc ccatacagct   55140
tagtggcata aaggagtcgg catgaacgtt aaaaaaattg tccgctacct gctgctcact   55200
gtggtttgtg taggcttagg gttggttggg tatcagcaat ttggcacgat aaccgctgct   55260
aaaactaaca atgcggatat cgctgccagc gtgtcacctc aattaaaaga tgggctgaat   55320
gtttattatt ttcatggaaa tcagcgctgt acaacgtgtg tccgcatgga aaaattcaca   55380
cagtctactg tgatgaatca gtttttcaag caagtgcgcg atggtgaaat gcagttaaat   55440
ttggtgaatg tcgatttgcc tgaaaaccag cattacatcg atgattatca gttggtatt    55500 cgtaccgtgg tgattgctaa tacccataat ggcgtggata cagattggcg acggttagac   55560
cgtgtgtggg agttggccaa caacgagctg gcattcagcc aatatttgac tgaagagatt   55620
aacgcaatgg ttaatcaaat tcaggcaaat caaaccctcg cggcgccatc tcccaaggag   55680
ctcccccatg gatgagtggg cagtcatgct gttatcggcc ttttggtttg gcattttaac   55740
ctctataagt ccctgtcctt tggccaccaa tgtggcggcc atttcctata tcagtaaagg   55800
aatacaatcg ccttatcggg tagtgggtac tgggcttgcc tacacgatag ggcgcatgct   55860
gagttatttg gtgattggtg tgatattggt tggcagtttg ctctcgacaa tgacattatc   55920
cgtcgcgctt cagaaatata tgaacctact attaggtccg atttttgatat tggtagggat  55980 gtttttgctg gagttattga cgttgcgtct accgggtgat ggtgccttaa tcgaaaaatt   56040
aaagtctaaa atcaaccctc agggatatgt aggagcttta ctgctaggcg tgttatttgc   56100
gctgtcattt tgtccgactt ccgccgcgct cttctttggt tcgctgctgc cgcttgcact   56160
agagtcacaa tcgagtattg cactgccagc gatttatggt tttgcgactg ggctgccggt   56220
tttagttttc gctattttgc ttggcgttag cgcccatcgt gttgctaaag cctacaacca   56280
tattttgacg tttgagcatt gggccagaaa aatcactggc gtggtgttta tcatcattgg   56340
tgcctattac gcttgggtga atattttcgt tccatctttg ttttagcata attttattcc    56400
taacaatgct tatcttgtga ggtccttcct gtgaaaaaaa cgttggtgtt aatagttgga   56460 agtacccttta ttctattaat tgggatagta gtttggggtc ttaattttttc ctcaaaaaca  56520 caatatgctg aaagtaaatt aacggcagag atgatggcta agtcaacgtc taaaaagtcg   56580
```

```
caactacctc ctgcagttag cctttttaaa gtcacaaatc aaacgtttag ccagtatatt   56640
gtattgactg gaacaattga gccaacaaaa atggcgagtt tggcctctcc ggcagaaggt   56700
ccgattctta atcttgtggt gcgcgagggg gacactgtta atttaggaca agagatttta   56760
cgcattggac gaactcatgc ggctaattct tttcaaacat ctgccgctga agaagtacgt   56820
aaacaagtat taaatttaaa gcgtattgaa actttagtta agcagcatac tttacctgag   56880
gagcagttag acgaagcact agcatcatta gaaaaagcga aggcggcatt gagccaagca   56940
aaacaagctc ttaatgatta catcgtgacc tcgccttggt cagggattat atctaaagtc   57000 ttggttttcag atggtcattt cgttataccc cgtagtccct tggttgaaat gtatgatcca   57060
gatagtttgg tattacgatt tagcgtcgca gaagcccaag ctttagcgct taagaagggg   57120
cataaaatta aagcgacttt tgatgggctt gctgggaagg aatttgaatt agagattatt   57180
cgagcttatc ccgatttaga tagaaagtta cgtacgcgtc tttttgaggc ggcgctgcct   57240
gtaaatgagt ttattccagg tatgtttgcg cggatcagtg caatacaaca aaaacacgaa   57300
aatacccttg tcataccgat tgatgcgctt caagtgcaag gaaatgacaa aagtgtgttt   57360
gtggtgactg ataatatagc cactcgacga ttagtcgaaa ctggtctaga gcaggatgat   57420
caaattgaag tgttatcggg actgaaagcg ggcgagaaga tcgttctaac tggcattgaa   57480
cgggtgaaaa atggctctgc agtaagagta ttggagcaac ccgctaaaaa caatagcgcg   57540
ggtgttgtga atgatcatt aaagccgcta tttctcgtcg aatttcaacg gctgtattgg   57600
ctttcggttt agctattttt ggggcgctaa atctgaatat gctacctgtc gatttcttac   57660
cttcggttaa atacctctc atcaagttat cgatagtttg gcagggtgca acacctgagg   57720
atatagacca aaacttagcc gatcctattg agcgtgaact cgcctcagta gatggtctag   57780
attatctttc atctagcgcg atagagggcc tatatcaatt ggatgtcaat taccgttacg   57840
gtgttgatgt tgatgttgca tatcaagata cgttagcggc gtttaatcgc tccaccaagg   57900
agctgcctgt tgatattgag gctgccgtca tcatcaaagc cgatccgtca caattaccga   57960
tagtacaagc tgtgtttgag tcggaacata tggatttgac tcagctgcgt acttgggttg   58020
attcatggtt aactcagcga ctgttatctg ccggtggcgt agccgctatt gatgttgccg   58080
gcggtcttga gcgtgaaatt cgtattttg tggatgatga aaaactagaa gcccacggat   58140
tagatctcac cacgttagaa cgggtcctcg ctgctgagaa tttacaacgg ttgg cggaa   58200 gggtgactgg ccaataccgt gagaatatag tgagggtgat gggggagttt aggcagttag   58260
ctgttattca agatctcgta ttaagccgcg ataataatgg caacattgtt cgtgtcaggg   58320
atgtggccga ggttaaagat agccatgaag acattcgtat gctgacccgc ttaaatggtc   58380
atccggcggt taaagttaac gtgattaaac aagccgacgc taatactgtc acaacggtag   58440
ataatgttga ggaccgttta gcggagttag cgccatcttt tcctaaggat atcaaattca   58500
ctttagttga aaaccaagcc gactatatca atgattctat ccgtggtgta cgtaacactg   58560
ccttagaggc tatggcgctg gttgtgctgg tattattcgt atttttaggt aactcaaggc   58620
aagtgttaat tattgcgata gccttgccat ttgcattatt ggtgaatttc ttttttaatgc   58680 acctcgcagg cttttcactc aatatttttt cccttggtgg tcttgtcgtt gcgattgggg   58740
tgttacccga cacatcaatt atagtggttg aaaatatttc ccggctgcgt agtttacatg   58800
ataaggctaa cccacaatcc atctccgagg aggctacact ggaagtgggt ggggcgatta   58860
tggcagcgac agtgaccttt atagcgctgt ttgttccgtt tttactcgtg cctgggctaa   58920
tcaccttact atttaaagag ttagtcctag ttatccttgg tttgatgatc attgcaggtc   58980
```

```
ttgccgctat cacactgact cccatgctag gtggcgtgtt attaaaagcc aatcaacgcg    59040
aatttgcctt cagtgagaag attaaccatg cttacgctg gcttatggc gtcttgttgc      59100
atagcgcatt gcagtttagg ttaaccacta tatttatatt tattggtgtt gcaatcggtg    59160
gtgtgctgct gtttaagtcc gcagggtctg aattttccc cgctgttgat gatggccgta    59220
tagtcgttaa aattcgaatg cctgcggggg cgaatttagc tcgcatggat gccatagcac   59280
agcaagttga agcattagtg ataggcgatc agcgagttcg tagtgttttt gcgctttcag   59340
gtggtgcggt caggggactg tataccaata aaattggtaa tgaaggtgaa gtcgatattg   59400
aacttgtccc ctccagtgag cgtaaaatta ctactacgga atacattaaa gaattgcggc   59460
ctaaggtggc taagttgcta gccccggggg cgatattagc ggtcaatcag gcaaagatgc   59520
ggggtattcg ctctgtggga caggccgaaa ttgaagttga aattaatggc tcagaagttg   59580
atacactttt tgatgtggcg aataaattgg cggcaaaatt agccgaaagg cccgaattaa   59640
ccaatgtcta tgtctcgctt gattcttcga agcctgaatg gcaagttgat attgacagga   59700
ctctggccgc cgaacatggc ttatctacta aggaaattgc ccacgttctt aacggctaca   59760
ttaatgaaag tgtggcgaca cgttatcgag aggcgagtga gttgtatgat atccgaatca   59820
ttatgcctga gtcacagtta cggtcgcgct ctgatgttga aaatatctct atagccacgc   59880
cttctggtca ttatgtgcgc cttaaagacg tagctaaagt gaccgcagca acaggtcctg   59940
ttgaaataat tagaaaaaat cagataaaac aagtaattgt acgttgtgat ccgtcagcaa   60000
ctgatcttaa ctcagcaaaa gaattggtca ctaatattct tacagagaca acttggccta   60060
cgggatacac ttattcgata ggcggtaagg cattgcaaat gacgcaaatg caaacgacag   60120
tgcaaagtat tctgggctat gcagtatttt ttcctttatt gtcttagcgg tacaatttaa   60180
tagtattcgc cttcctttgg tgatcttatt tgccgcacct ttttgcctta caggtattgg   60240
atatgggctc ttcttagcag gtcaaccgtt tggagctacc gtgatcattg cggctatgat   60300
agtgctagcg gccaatgtta ttgatggtgt gttactgatc caaaccgctg agcgtcaaaa   60360
acaacagggt atgaccttgt tgaaagcgac atttgatgca ggtttgagtc gacttcgtcc   60420
tcgactgatg acggtattac ccgccgtatt aggctttaca ccgttagcat ttgcatttga   60480
ggaaggaggg gagttattgc gtcctatggc cgctgcagcg ataggtggtt tgctattaaa   60540
tgtctttgtt gcgctatttc tggttcctgt tctgtatact tttatggcat ctacaccaga   60600
accagcatca gctgatataa cttaagcggt agggtaataa acgcggttat caaggttaaa   60660
aaacgcctgc gaagtcatta gcttcgcagg cgtttatttt gagattaagc agcgtttagg   60720
gagtaatcta taaacgaaaa tgttattgag ccactctttg cccattggca tcaataacca   60780
cttcaccgtc ttctttagta aaagcaccca gttgggggttt gggtataata tccaataccaat 60840
gttccgaggg gcggcagagg cgagtgccta atggagtaac gacgataggg cgattaatta   60900
ggatcgggtc tcaagcata aaatcgatta attcactgtc gctaaactta tcttcactta    60960
agcctaatac ggtaaagggc tcaacatttt gccgcagtaa actgcgtacc gaaatacccca 61020
tctccgcaat cagttgctgc agagtttgtc ggctcggtgg cgtctcaagg tagaggatta   61080
tggtcggttc aaccctgaa ttgcggataa ggcctaaagt gttgcgcgat gtgccacagg    61140
ctggattgtg gtaaatctta atgctgtcat caatcatatt agtcataaca tgtctctgat   61200
aaataatcgc ttataaattt atccataggc actaaataga tgctctagtg cccatggaag   61260
aagattagaa ggagaggcgc agcgccagtg ccgctagggt gacaaatagc actggtactg   61320
```

```
tcatcacaat gccgacgcgg aaataataac cccaggtaat attgatattt ttctgcgcca    61380
gtacatgcag ccataacaag gttgctaaac tgccgatggg ggtgattttg ggacctaaat    61440
cgctaccaat tacgttcgcg taaatcatgg cctctttaat cacgccagtt gcattgctac    61500
cgtctatcga cagggcgcca attaacactg tgggcatgtt gttcatgatg gacgataaaa    61560
aggcgaccaa gaagcctgtg cccatagtgg cagcccaaag cccttgttct gccaagctat    61620
ttaatacgct tgataggtaa tcggttaagc ctgcgttgcg aagaccataa acaaccaaat    61680
acatgcctaa tgaaaagact acgatttgcc atggcgcgcc gcgaagtact ttagtggtat    61740
ctatggcatg gccttttttc gcgacaacaa acaggatcag ggcacccacg gcagccacta    61800
aactcacggg cacaccgagt ggttctaagc caaaaaagcc caccaagagc aagactaata    61860
caccccaacc ggttttaaag gtgttgaggt cgcgaatggc ggccttaggc tcgcgtagtt    61920
tttgcaagtc gtaggtcgcg ggaatatctt tgcggaaaaa cagatgcagc atgactaagg    61980
tggcgctaat agcggcaata tcgacgggca ccatcactgc agcatattcg ttaaagccta    62040
tgttgaagaa gtcagcccgaa acgatattca ctaagttaga gacgattaac ggcaaactcg    62100
cggtatcggc aataaaaccc gccgccatta caaaggctaa ggtcgctccg gcgctaaagc    62160
ccagagccag taacatcgca attactatgg gggtgaggat cagcgccgcg ccatcattgg    62220
cgaacaatgc ggcaacagta gcgccgagta acactatgta agtaaagagt aaacggccac    62280
gacctttgcc ccaacgggcc acatgcagcg cggcccattc gaaaaatccc gactcatcta    62340
ataataaact gatgatgatc acggcaataa aggtggcggt cgcattccag acaatattcc    62400
ataccacagg aatatcccct aagtgcacca cacccagtag tagagccaat acggcgccca    62460
aggtggcact ccaacctatg cctaatccct taggctgcca aattactaac actatggtga    62520
gtacaaaaat tgccccagct aaccacatac aagctcctaa aagggcagat accgtctacc    62580
cgtaacccta aaataatgcc cataaggata cattaatgtt gttttgccag taggcttaat    62640
cgcgtaatac caatgggttc ttcttgctgc aatgggatta atgccaaccg agaggctaag    62700
ccctgttgca ctttctctat ttgcaccagt tcatggcgag cgcgtacttt taataatggc    62760
gaggtcgttc tggcaacggc gaggctatta ttgataagcc atgcccaagg ttcaatccct    62820
gcgcggcgca aatcttcctg caaattcgcg gcttcgagca caggggtagt tcgggcaaa    62880 gtgaccaata ataccttagt gcgctctttg tcttgcaact gcatcattgg cgttgaatag    62940
tgagttgttt ctcccatacg tttagctact tcacggtggt aggcgccggt agcgtcaagc    63000
agcaataagg tatgccccgt tggcgcggta tccattacca caaagcgttt ccccgcctcg    63060
cggataatgc gcgaaaaggc ttggaatacg gcaatttctt cggtgcatgg cgaacgtaaa    63120
tcttcttcta acaaggcttt accttggaca tctaacgctt tgcccttcgt tgctaacacc    63180
tgttcgcggt agcgagtggt gacttcgacg ggatcgattc tgctgacttg caaattcgcc    63240
aattgaccat gcagcgtttg ttctagatgc gcggcaggat ctgatgtggt caaatgcaca    63300
tctaagccca gctctgccaa tctgaccgca atggcggcgg ccagcgtagt tttcccgaca    63360
ccacctttgc ccatgagcat gataaggcca tggtcctgct gcgcgatttc actgattaaa    63420
ctatccagtg ttggcacttg gggctgactg tcttgcttac attggtcttg ctcatccatt    63480
gcgggtaaat ctatgtcttc tgcaggcata aagagttggc gtaatggcgc aacgcctacc    63540
aggttcatcg attgaagtat cagcgtttcg tgaggtaatg ccgtgagaat gggggataaa    63600
ttggtgagca ccgcttgttc acgttggtag agtgctgagg caaggggatc attgagtgct    63660
gcgcctttgg gcaatacgcc gttaatcacc agatattgat tcttaaggcc cacttggcgc    63720
```

```
aattcttggt gagtgcgctc cacttctatc agggtggatt gctgtggacg cgcaactaag   63780
atcaagcgtg ttttgtcggg attggccagt gcagctaatg cttgcgagta gcgttccgcc   63840 tgttttcga  ggcccgctaa tgggccaaga caggaagcgc cctcggggtt agtctcgata   63900
aagctgctcc aagccccagg gagttgtaac agcctaatcg tatgcccgt  tggtgcggta   63960 tcaaaaataa tatgatcgaa atcttgcagt agcgatgcat cggttaataa accggtgaat   64020
tcatcgaagg cggcaatttc agtggtacag gcaccagaga gttgttcttc aatactgcga   64080
actacatctg gcggtaatag gcctttgacg ggatccacaa tacgagcgcg gtattgctct   64140
gcagctgctt gaggatcaat ttccagtgcc gttagtcccg caacgctgtc tattggcgtg   64200
agtttattac ctatggtttg tccgaaaact tgacctacat tggatgcggg atcggtactg   64260
accaacaaca cccgcttacc actgtcagct aaggtaattg ctgtcgcgca ggatagcgat   64320
gttttaccaa caccgccttt accggtaaag aagaggaatg cgggcggatt ctgaataaat   64380
ttcattagat tatccttggt gtttccaaac gtgagttgac taacagcaag aggttttgcc   64440
actgcaacaa ggagcgatat ttttcgcagg ttctgcgata tcgatcttcg cccaacgggc   64500
tagttcctgc cgacttggat aacgcccgc  taatatcatc tcaccattta ggagaataag   64560
cggtagggat tctgtaccag atgtttctaa aaagcgtctg acaagggcat tttctgcaaa   64620
ggccatgggc tgttgggata aattaaagcg atctactgta atgtcttgtt gttttagcca   64680
ttggcaatcg gcggcaaagg tgacgagtgc ttggtcaact tcagtgccac acacgccaga   64740
gctgcaacat aaagcgggat cgaatattga aaattgagtc ataacttttc cccataaaat   64800
tgattttggt ttgaaagtgg aggcgataaa aggtggtaac aggcgcctta aaaatcactt   64860
catataaaca tatgaatttt catatatact atacgcttca aaaaggggga gtcaaacata   64920
ctgaggatat tcgtcattaa aatctaaaaa atctgaaata gatcatcttt atacgtgtaa   64980 attttttttac taaacttcag gatattgttc ttgatcacat ttttatatt  tttcaactta   65040 gtttcacaat tgtaaatttc agtaaaggat acttgtgtat taattgatct aaatcgcagt   65100 tacatacccct aaaagatata tattaaattc catacccctta tcaggagtgt ggaaatgaaa   65160
aaagaaattc aagtcaactt ggggcggcgc cagctactca agtcaactgc ggcgggcacg   65220
gtattaacag gtattggtgg gaccttatcc tttaccccta tcgttgatag tattgctgca   65280
gaattacctg cgcctttgcg tagaaccggc actggagagt ggttagcgac gacctgccaa   65340
ggttgtacct catggtgcgc taagcagatt tatgtgatgg atggccgagc attaaaagtg   65400
aggggtaatc caaactccgg cgtacacggt atgtccagtt gccctcgcca gcacttaagc   65460
ttacagcagg tttacgatcc cgatagattg cgtacaccaa tgatgcgaac taatcctaaa   65520
aaaggccgcg atcaagatcc taaatttgtc cctattactt gggataaagc gctggatatg   65580
ttagcggata aaatcattgc tttacgcgaa gctaatgagc cccataaata tgcgctcctt   65640
cgcggtagat attcgcatat cactgattta ctctataaaa agatgaccaa tctgattggt   65700
tctcccaata atatttccca tagttcagtg tgtgctgaag cccataaaat gggaccgtat   65760
tatctagatg gtaactgggg atataaccag tacgatatca aaaatgctaa atttatttttg  65820 tcatttggcg ccgatcccat tgcgagtaac cgtcaagtct cgttttattc gcagacatgg   65880
ggtgattccc tcgatcaggc tacagtcgtc gtagtcgacc caaggctttc tgcttcggcg   65940
gccaaagccc ataaatggat cccgattgaa cctggtcaag acagtgtgct ggccctagcc   66000
attgcccatg tcgccttggt tgaaggtgta tggcataagc cttttgttgg tgattttatt   66060
```

-continued

```
gagggtaaaa acctgtttaa agcgggtaaa accgtcagta tcgagagctt taaagaaacc    66120
catacctacg gtttagtgga gtggtggaac caagctctta aagactatac gccagaatgg    66180
gcgagcaaaa ttactggtat agaccctaaa accattattg ccattgctaa agatatgggg    66240
gcggcggcac ctgcggtgca agtatggact tcccgtggcg cagtgatgca agcccgcgga    66300
acatatactt cgatttcttg ccatgcttta aatggcttat ttggtggtat cgatagtaaa    66360
gggggtttat tcccaggtaa caaaacgcct ctcctgaaag aatatccaga ggcaaaagcc    66420
tatatggatg agattgctgc taaaggtgtc aaaaagaaa  aaattgacca acgtggtcgt    66480
ttagcattcc ctgccattgc taaaggtaag cctggaggtg gggtgatcac gggtaacgtc    66540
cctaatggca tgctcgctgc tgatccttat gaaataaaag tgattttagc ttattttaat    66600
aacttcaact tttccaatcc tgaagggaaa cgttgggatg aagccttaag caaagtcgat    66660
ttcatggccc atgtgaccac caacgtgtcc gaattcagtt ggtttgctga tgtgttatta    66720
ccttctagcc accatatgtt tgaaaaatgg ggtgtgttgg attctatcgg taatggtgtt    66780
gcacaggttt caattcaaca ccctcgatt  aaacgtctat gggatacccg tatcgatgaa    66840
tctgaaatcc cttacatgtt agctaaaaag ctggcagata aggatttga  tgcaccatgg    66900 cgttatatca atgaacaaat tgtcgatcct gaaacaggta aacctgctgc ggatgaagct    66960
gagtttgcga agttgatggt cagattcttg actgcgccgc tgtggaaaga agatgcgtct    67020
aaatacggta taagctcaa  ttcatggat gagttcgtgc aaaagggggt gtggaatagc    67080
tctccttata agcttgagtc tcgctggggt aagttcaaaa cagaaacctc taagtttgag    67140
ttttacagta agaccttgga aaaagcgttg caagaacatg ctgataaaca caagtcagc    67200 atagatgagg taatgaaagc ttgtgactac caagctcgtg gtcaattggt atttatccct    67260
cattatgaag aacccatcg  atttggtgac gaagccgagt tcccgctgtt actcgtggat    67320
caaaagtcac gtctaaacaa agaaggtcga actgcaaata gtccttggta ctacgagttt    67380
aaagatgtcg atcctggtga tgtggcgaat gaagatgtgg ctaaattcaa cccgatagac    67440
ggcaagaaat ttggcctcaa agacggtgat gaaatccgca ttacaagccc tgtgggtacg    67500
ctgacctgta aggcgaagct atgggaaggt gtccgtcctg gcactgtggc taagtgtttt    67560
ggccaagggc attgggccta tggacgttac gccagtacca aatttggcat aaccccaaga    67620
ggtggctcaa ataatgactt gattgcagac aggtacgatc gcttaagtgg cgcgtcggca    67680
ttctatggtc atatccgtgt tcgtgttgag aaagtgtgag gtaacccact atgagattag    67740
gaatggtgat tgacctacaa aaatgtgtag ggtgtggtgg ctgtagctta gcctgtaaaa    67800
cagagaacaa cacgaacgac ggtattcatt ggtcgcatca tattgccacc actgagggga    67860
tttttcctga tgtaaaatac acttatatac cgaccttatg taatcattgt gatgatgcac    67920
cttgtgtaaa agtctgcccg acaggggcta tgcacaaaga taagcgcggc ttaacgctgc    67980
aaaacaatga tgaatgtatt ggttgcaaga agtgtatgaa tgcttgccca tacggcgtga    68040
ttagttttaa tgcggcaaca ccacatcgtc gttggcagga tgactcagag gtggtcgcga    68100
acggaactgt atctccactg atgctgctca aacgcacggg ggctgctgca tcacccaatg    68160
aaaacccaga gcgggtgat  acttaccctg ttacacgacc aagacgcact acagagaaat    68220
gtactttctg tgatcatagg cttgataagg ggttgaatcc tgcctgtgtt gacgcttgtc    68280
catctgaagc gcgggtgatt ggtgatttag atgatccgca gagcaaggta tcccagttga    68340
ttaaattgca taaccgatg  cagttgaaac ctgaagcggg aacgggacca agggtatttt    68400
atattcgcag ttttggtgtt aaaaccgctt attaatcata taggttaatt tgttagttaa    68460
```

```
agccacagat gagattctgt ggcttttac tttatacgcg ccctgttaat cgctaaacat   68520
cagcgaatct aataccccct ggccgctgtg aactccaccc tcagtcacca tggccgattt   68580
gctgcgaact aaatatcccg cataaccggg gttgtcgcta ttagagctat cctccatcac   68640
aggctcgcca tcaatgtgga tggtgaacat gcctatttca gggatcatgt catttatggt   68700
ttctatcttg ccgttacgca ccactaaggc tggtgttgct ctcggtctag ggtgtaagcg   68760
gcgcatcagt gaccatgctt ggtattgcgc gggttctagc tcggctaatt catgtgaaat   68820
atcggtacca aacaggcaat tgccaccgcc ttcaccttga tttttagca cccaagtgtc   68880 tattggggat gcttcgacta atttgatact ctctggggta acggggcgca tctcgccgag   68940
gagggatttg accattttgg cttgttgcag cgttaaacca aactgagtca aggacatttc   69000
atccatagac gagagcagca tctgcatccg cttactggtt gccagttgtt gccctacggt   69060
ggcattgacg gcaacgcgat gttttcaat caatacacgg atcgccatca gggcttggca   69120
gtttttgtta ccattgatgt caacggattc ataatctgta tattgataac ccgctcgcag   69180
ataaacggta tcaatagtgc ctatgccttc gagtatcagt ctatgttttt cgcctgtggt   69240
aacttgttct tgtagttcac taaaggttct gcgaattgtt tgtatctttt gttgttgtaa   69300
cgcgagttcg agtaaatgtt ggtcaaacac attgtcttca ttttcttgca ctatcatcaa   69360
aaatcttgct ggccccgcat cttcaaattc ctgttttatc ttaaaggttg ctttagctat   69420
gcctgcggat aattgttcaa tggcatgatt atcaacaagt tcacctatag gcagttgatg   69480
ccattgctgc aaataatggt ggaattgatg cactctctga ccaaagggcc ccataccagc   69540
cgcaatgcca ttaaactcca ctagttttgg ccctaagtcc ttatcgtcca tgaagtcact   69600
acgcataatg agcaatggca ttctctgcgc tggagtctgc gagcaatgta cttgctggtg   69660
tataccaagc aaggcggcaa aaagggatc gctagccgta ataggttgaa tcgcatcgta   69720
taagaaggca tgttcttctg atatagaatg aataagttta ccgagtaaat gcacagaatc   69780
ttttaagtat tgatagtgac ctcgactgat taaactcggc gttaaggtaa atggcgcgtg   69840
gcgggcagaa tattgggttt ctttaaacgc catgccatgg gttagcgccc attctattgc   69900
atcatctttg gcttttagac taataggtga attcattatg cttctcttaa gcgaggcgaa   69960
tttattcgca ataccagtat gttataggtt tacgttttag atgatttaat cttggggcgt   70020
aaaggcccta tggcactcac tttaggagca tgcggtgagt gccatatcga gttagaacat   70080 tatttttgt gttaactaaa tacatagcta taaagaaatc cggcagtcat tgccatactt   70140
aaaattaccg ctaaaaatgc aataatcatc tgattttaa agagggattt tagtaaaatg   70200
acttctgtta aactcgctcc tgcactgccg ataattaagg ccattacaga acccatcgcc   70260 atccctttt gcactaatgc ggcgctgaga gggattactg cttcggcgcg aatataaagt   70320
ggaataccaa ttaaagccgc cacaggaata gcgtaccatt ttgcttcacc ggcatattta   70380
acgattaaat ctgtaggaat aaaaccgtag atcattgacc ccaacagaat gcccacaaat   70440
agataaggta gtacttgttt gaagtccttc caagtagagt gccaaactct tatccagcgg   70500
ctctgaggct tacttttggg tgctatatca gtagtcgtta ctggtttagt atcgcaacat   70560
gagttcgcaa cagctgtggg tttagtatcg caacatgagt tcgcaactgc tgtcgattta   70620
gtttcgcaac aggtactgga aaaggaggaa ggtttagtgt cacaacatga agtgacagtg   70680
tcttccagag tataagcttc tttacggaca tacctttcaa accccagctt ttcaagcata   70740
tagcctgcaa tgacagagac tcccattgct actacaaaat aaaaaagtgc tactttttaag   70800
```

```
ccaaaggtga caacaaatag tccgataata atcggattca gtaatggact ggcaaacagg   70860
aataccatca tagggccaaa accggcacga gccctgagta agcctttcaa aaatggaatg   70920
gtagaacaag agcaaaacgg ggtaattgac ccaagtagtg cagcaatgac ataacctctg   70980
ccgttgcgtg agcttagcat cgcttgtatt ttttgagggg tgataaattc ttgtaaaata   71040
cctactaggt agcttatgac aagaaatagt agggtaagct caacggcaag gaaagcgaac   71100
atgcttgccg tttctttcat cataagaatc atttcaggac tcattttttt acctcttcaa   71160
cttaaagttt cgaatattct agaataatag tgtttgggcg aagtgttttc aatatattat   71220
ttctagaata atggaaatat ttggtatacc tattgatgct aaaacacatg acaccctgct   71280
tttgattgtt tatgagtggt cgattttgag gtcgctaggg taaggatatt tctggtatta   71340
tcgaattact taacgaaatg aggccgatat gaatatagag aatgctgcta agtattaaa    71400
agaactgggc catccaacgc gtctcgccct atttcgatta ctggtcaagg gcggatatgc   71460
tggcgttgcg gtgggtcagt tacaagacga gttgcagatc cctggttcaa ctctctcaca   71520
ccatattagt gcccttgtgt cagcgggagt gatttcccaa cggcgcgagg gaagggtgct   71580
gtactgcgta cctgactatg aattattaca aggattagtg catttttttac aagatcaatg   71640
ttgtagtgct cagtgaacaa ttttgttaaa tgaacagtaa attattacat gtggatattt   71700
acatatatga taaatcgtat atagtgacat tctctttcat caggactcat tcccatgaaa   71760
aaacgtgtac tttttctctg tgttggtaat tctgcgcgtt cacaactcgc tgaggcctta   71820
ttaagacacc aagcccaaga gcagtttgat gtgtttagtg cgggtacgca gcctgagccc   71880
atcgatgagc gaactcttgc gcttttgcag aaaaataatt tgggtacgag tgagttacgt   71940
tcgaagtctg tcagtgagtt tagtgggcaa tcctttgact ttgtgatcag tctctgtgaa   72000
aaatcaacgc aagagtgtca gagtttcccc ttggcagata agattattgc ttgggattat   72060
cccgatccca aaatcgaatc gggcactcgt gggtttgaac aaacttttag agaactcaac   72120
gaaagaataa aaatgtttgt actcgttcag tctaaggatc ttaatgatta atcctacgca   72180
attttttaaa tgtttagccg atgaaactcg cttgcgctgt ttgatgttga ttcagcacga   72240
gggtgagctt tgcgtctgtg aattgaccga agccttgcag gaaattcagc ccaagatctc   72300
gcggcattta gcccaattac gtaagtgcgg attattagtc gatcgccggc aggggcaatg   72360
gattttctat agtatcagta atgatttacc cgaatgggga aagtcagtgt tgagtgaggt   72420
taccagccaa aatccggtat tccttgaaga aaacatgcgt aatctgtgca agatgggtgg   72480
ccgcccccgag cgcgctagag cctgttgcta aagattgttt gtaacaaata aataaaaaat   72540
ttaatctaaa atatatgaaa attcatatat taaatcgcta gaggttgata tggcaccagc   72600
tataaaagtg ctcttttctat gtacccataa tgcctgtcgc agcatcctag ctgaagctat   72660
aggtcgagat ctcgtcggta agcaagcttt gactactatt gctcaatggc aatttgcgag   72720
tgccggtagt gaacctgccg gggtcgttca tcctcaaact ctattgcaac tagcacacag   72780
aggctatgtt accgaagggc tctgcagcaa aagctgggat atgatggcgg atttcactcc   72840
tgacttagtg atcactgttt gtgataatgc tgcgggagaa acctgtcctt tgtggttagg   72900
tcaaacactt aaattacatt ggggtttacc cgacccaaca tcaatcgacg cccccgatat   72960
agatgagcaa tttagctatg ttatagaaac acttgaaaat cgtataaagg cattaatctc   73020
gttgccgctt tcggcaggta tagaagctca aaaagcatca ttacaatcaa ttgcgagtca   73080
atttccactt attcaaagat aaatggttttg tatttaattg gtgtttattc aactaattaa   73140
aatagcaata tccttttgct tcatcgcttt catgtatacc aaggaagttt gattatgctg   73200
```

```
caactattttt ccgatttagc gagctggcta acctttggag taatgggttt agatcccaat    73260
actaagctcg ccgacgccat ccatttttt attgaagata ccactaagat ttttgcgctc    73320
ctgttgctga tgatttatgg catcgctttg gtgcgggcct cgctcaatgt cgagcgcgtt    73380
cgggattact tggcgggtaa aaatcgtttt gtcggttact ttatgggatc gggttttggc    73440
gcggttactc cattctgctc atgttcgagc attccggttt tttaggtttc acctctgctg    73500
ggatccccgt tgggatcact atggcgtttc tgattacttc gccgttaatt aatgaagtcg    73560
ccgttctgtt gcttgtgagt ctgttgggct ggaagtttac tgtgatatac gtgctggtcg    73620
gcatgtcagt gggtatgttg gcggggcat ttttggacac gatccgcgct gagcgttggc    73680
tgcagtcctt tgccgccaaa gcactcgagc aaggaaaggc acaagcaagt cacgataata    73740
gcgagggtat gacatcaaca tccatgacgt taacggaacg gcatgaattt gcgaaaggcg    73800
agaccctaga gatttttggc cgagtgtgga aatgggtcat tattggggtt gggcttggcg    73860
ccgcactcca tggatttgta cctgacggtt ggatcgaagc ccacttaggc gatggtcaat    73920
ggtggtctgt tcctgcggcg gtattgattg gtattcctct gtattccaat gccacagggg    73980
ttatccctat catggagagc cttatcacta atggcttgcc cgtagggaca acattggcat    74040
tttgtatggc aacggttgcc gccagttttc ctgagttcat tttgctcaag caggtgatgc    74100
aatggcgttt actggccatc gttttgcca ttttattgat ttcattcacc ttaataggtt    74160
ggatctttaa cgctataggt cccgttctgt gagaattata aaaatgctaa acatcaaagt    74220
attaggcagt ggatgtgcca aatgcacaaa aaccgctgag attattaccg ccatcgccaa    74280
cgaaaagggc atcagtattg cgctggtaaa ggaaaccaat ccagaagtca tcatgggcta    74340
taaggtgatg agtacacccg ctgtggtgat tgatgagaag ctagtgcatt ggggctccat    74400
tccccataga gccatgattg aatcttggtt agtggggtaa cacttaaatg tcacatccat    74460
ttgatatttt gccgctagag agtggtgcta ggttgatttt taccccttgc ccagggacta    74520
aatctgtccc tgtgacagag gcggtggcaa ttcttaaagc ggcgggaact gaggtcatca    74580
taaccttaat gccacttgcc gaattgcaaa catttggtgc tgcattattg cccgatattt    74640
gccatgaagc ggggatccgt tggttgcatt tacctataga agatgatgcg gcacccgcag    74700
aggtattcga gctcgcgttt gcacgacaca aagcagaact gctggcattg atgcaaactc    74760
aatccacaat tgccattcat tgtcgcggtg gttccggtcg cacaggatta atggcggcaa    74820
tcttgctgtt actggcggga ggcaccttgg cagaagtgat tacccaagtg caatccattc    74880
gccctaatgc cttaaccaat gtgcatcaac gtggctatat cgaacagata acgctttaat    74940
cttaaacaaa taatataaaa cacctaatat aaaactgagt gtgaaggatg caggtatgac    75000
aatcaaaatc gggataaatg gctttggccg tatgggacgt ttagcactgc gcgctgcttg    75060
gggctgggaa gaggttgagt ttgtgcagat taatgatccc gccggagatg cggcgacctt    75120
agcccatttg ctgacattcg attctgtgca tggccgctgg caacatgagg cgagcagcga    75180
tggcgatgac atcattatcg atggcaagcg tattcgctgt actcgcaata aaaccatcgg    75240
ggaaaccgat tggtccggtt gtgatgtggt gattgaagct tcgggtaaaa tgaaaaccaa    75300
agcagtgctg caagcttatt tagatcaagg cgttaaacgc gttgtggtca cagcgccagt    75360
taaagaagag ggcgtgttaa acgttgtcat gggagtgaat catcaactct atgacaaagc    75420
tattcatccg attgtgactg cggcctcctg tactactaac tgtttggcgc cgatcgtcaa    75480
agtgatccac gaaaacctcg gcatagtgca tggttccatg acgactattc acgatattac    75540
```

```
caacactcaa actattttag atgcaccgca taaagatctt cgccgtgcgc gggcctgtgg    75600
tttaagcctt atccctacga caacaggctc agcgacggcc attacccata ttttccctga    75660
actcaaaggt aagcttaacg gccatgcggt gcgggtgcca ttagcgaacg cttcattaac    75720
cgattgcgtg ttcgaggtga gtcgcaaaac gaccgaagct gaagtcaatc gcctgttaaa    75780
agaagcggca gacggaccgc taaaaggcat tttaggttat gaggaacgcc cattagtctc    75840
ggtcgattat aaaaccgatc cgcgttcgag cattatcgat gcgctatcga ccatgattat    75900
caatggcact caggtcaaac tctacgcttg gtatgacaac gagtggggtt atgccaatcg    75960
caccgtcgaa ctggcccgca tggtcggtct gatggataag gcataagctt tatgggtaag    76020
ctgacagggt tcttgtctaa catatcaccc gagatccgcc agtatttggt ggtcacaggc    76080
aactattggg cattcacgct caccgatggc gcattacgta tgttagtggt gctccatttt    76140
catggcttag gttatagccc gctgcaaatt gccatgctat tcctcttcta tgaaatcttt    76200
ggggtggtaa cgaacttagt cggcggctgg ctcggggcgc gtttaggctt aaataagacc    76260
atgaatgtag gcctatttat gcagattgtc gcccttagca tgctgcttgt gcctagcggt    76320
atgctcacgg ttgcttgggt gatggcggcg caggccttgt cgggtatcgc taaagatctc    76380
aataagatga gcgctaaaag cagtatcaag ttgttggtgc ccaatgatgc tcagggtgag    76440
ctgtataagt gggttgccat gctcactggc tccaaaaatg cgctaaaggg cgcggggttc    76500
ttcttgggcg gcgccttact gaccctgttt ggattccagc tggccgtgtt aggtatggcg    76560
attggcctat tactggtgtg gattttttagt ctgttaagtt tgcaacgcga tttaggtaaa    76620
gccaaaaaca aacctaagtt cacggaaatt ttctctaaga gtccggcggt aaatacgctt    76680
tctgccgcac gcatgttttt gtttggtgcg cgggatgtgt ggtttgtggt ggctttaccc    76740
gtttatttgg cctcagcctt tggttgggat cattggtatg tcggcggttt tctcgcactc    76800
tgggtaatag gttatggcat agtgcaaggc tttgcacctc gcttgacggg gacaaagtcg    76860
gcgagccaaa acaaggttcc cgatggacgt agcgccttag gttgggcggc gatattgagc    76920
atagtgccgg caggcattgc gctggcgata agttatgact ccatgccgc gaatatactg    76980 atttggggat tgatgctgtt tggcgcctta ttcgcgatca actcttcatt acacagctat    77040
cttatcgtca gttatgcgga tgaagatggc gtatcgttag atgtgggttt ttactacatg    77100
gctaatgcta tgggacgctt gatcgggact gtgttgtctg gctgggtgta tcaagtgtat    77160
ggcatggcgg cttgtctgtg gatatcggcg gcatttattg cgctcgcagc gcttatctca    77220
attaagcttc caagacatag agcgatataa agacattaaa cgcgaaaaaa tgtcacaaac    77280
aatatgcgaa ttaacatata tgtcatattt catatgtatt ctagcggtgt tacataaaga    77340
cagttaaatg acacctatgt ctccaaatga ggatatcaat atgaaaaaaa cagcgttaat    77400
gtcactgctt ggtttaggat tatttgcttg tgttgctcac gctagcgagt tcgatttacc    77460
gggttttgtc actgaagtag aagatggtcg tctatgggtg tttaaagaga attcggctga    77520
gttaactgag tttaaacagc atggtgagcc agcaaagcaa tttactgtca ttggtgttgg    77580
tcctaagggg atgacggtta agcggcccga tcaaataacc ttagatgaat atttagctaa    77640
ggtaaaagcg aactaatgta cttagtgaag cgttactcga atttctaaat cccattttct    77700
gatgttttac gagttggaac tttggttcta actcgtaata tctaaaaatt aggtgaatta    77760
ctctagccca gattgactga gtcagactta cctattcggg ttcacgtgcc aaaccctgc    77820 tattttgtgc agccttctta ctaaccaatt ttgccccat tgtgagctat gaccgattaa    77880
tcactcagtg cacagaggat aattgactta catttagtca ttccaaaaat atggaagtaa    77940
```

```
agtcaaatta cgcctctatc taagtgacca aatttagcgt accagtacaa gtcaataatc   78000
tgtgggtatt gaccagattt atgcaactaa agtggatttg tctgcaatta tttaccgttt   78060
tccatcattc attgccattt caagcgaaat atcactcgcc accgaaccct gattttttgt   78120
ggataacacc ccaaagagcg cggtgattat ccaccgaaaa aatcacgaac cggcagcagg   78180
accgaaattt tagaatttt taaatttcct gctattatta ctgattattt atacagtagt   78240
ttggtgctat gaaactcata acatgccatg cgagtgcagg aatttcgggt tttccaagtc   78300
ctgcagcgga ttacgttgaa ttacccctta gtcttgatca actgcttgtt gagcatccta   78360
gctcgacctg gtttggtcgt gctgcgggtt gctcaatgga aggggttggg atctatgatg   78420
gcgatatact ggtgattgac cgtgccgcta agcgccgtaa tctctctatt gttgttgcca   78480
gctataacgg agaatttacc gtaaagctcc tcgatgaaaa gcgccggtta ctggtttcta   78540
tcgatcaaca gcaaaacatg acgtccgttg caatcgatga tgcagatacc ttctcggttg   78600
aaggggtgat catcaagtca atccgacttc acgagcattc aagcttactt gaacaatatc   78660
tgagtcaatc atgtacggac tgattgatgc taattcattt tatgtgtcat gcgaattggt   78720
gtttagaccc gacttgcgcg aacttcccgc gattgtactc agcaacaacg acggttgttg   78780
tgtggcagtc aatcgagcgg ccaagtccgt tggcgtgaaa aaatttgtcc cttactttga   78840
gctgcaacat ttgtgcagac aacataatgt gcaggtgttt tcatctaatt atgaattgta   78900
cgcagatctg tctgcaaaaa tgatgcaagt gatcgggcgt ttcgcacccg agcaatacgt   78960
gtactccatc gatgagtctt ttgtgtcgtt taaaggctgt gctgcaattg cagacttaac   79020
ggcacattgt gctcagctgc gccgaacagt ttggcgtgaa tgccgtttgc cggtgtgtgt   79080
gggggttggt gagacattaa ccttggcgaa gttggctaat catgccgcga aacaattggc   79140
tcaatataaa ggtgtttgcg ttattgataa tgatgcgcag cgtattgaga ttttaaaatc   79200
gatgccagtt gatgaagttt gggggattgg ccgcaaacta acggtcaaac tgggattact   79260
gggtgtgcat actgcctatg atttggcaca actggcgccg aaagtggcgc gacaacattt   79320
ttccatcgat gtagagcgaa ctgtgcgaga actcaatggg cagatctgta aaacgtggga   79380
tgtcaccaaa gcagataagc agcaaatatt ttccacccgc agcctaggcg aacgaatatg   79440
tacccgggaa catttacacc aagcgttagc aaagcatgcc gcaattgccg gtgcgaaggt   79500
tcgagaacaa ggctcattgt gtaaagcaat ggtcgtgttt ccgccaact cgccacatga   79560
tccacagcct gtgtatttta aaaggcttgt tcagtttact tgtgccactg atgacagtcg   79620
tgaactgtgc gccgcggtta gcagcgagct atcaaacctt tatcgcccag gtgtgcgcta   79680
ttaccgaatt ggtgtaggcc tgattgatct ttgccctaaa acgtcagtgc aatatgactt   79740
atttaatgcg ccaaagagcg atcctaactt aatgaaaatc tttgatagtc tgaataatcg   79800
ctatggccgt gatgtgttgt atattgctgc acagggagt gatcagcatt ggactatgcg   79860
ccgtcagttt ttatcgccgc agtacaccac ccgttggtcc gatattccga tgattaaagc   79920
gtaataggat tttatggtgc tttatccagg ccttactcca cgtatacaac ctaaaacgtc   79980
tgtcataggt tacaattttt tgagaataag aggaaaaatc aaatgtctag gaacttagaa   80040
gttaaaaagc aacaagcgct aatggttaaa gagcaagttg acattatttt aaagcgttat   80100
gaactgagtg atgctgacaa ggacaaaata gcaaggacg ttgctgatgt tatcttgact   80160
gcttgggatc tacaactcag tgatttgagc tttggtaata cttggtgtaa acctgagatt   80220
aacactaaac agtgttaaat atttctctag gtcggcgttg cgtccatcgt tctaatatca   80280
```

```
cggaaatgat ggacacagaa cgtcgatcta catctagagc tacatctata taaggtataa    80340
acaatgagaa caaagaaga ttttttcttt ggtaagacgc atcaaggaag caaaggtata    80400
acactccaat tgagcgatat cgagtctctt gcggaaaaag tgtcagataa ttttttact    80460 gcacaactga atagaatgct gcaggagcat ggggaaggc tgactatatc agatgaaacc    80520
tcgcttccca atttctggag cctcatcgat aaaattgcca ttgagcaagt agggttcgtg    80580
gaaatttatg ctcgctatga cgtcaatgat agtgttaacg cgacgctggc ctgtgacatt    80640
gtgctgttaa atggtgtgct ctcgattaag tcgcattggt gcgcgtataa agaaattaga    80700
gcgggtgaga ttgtttcttc gttattggtg cccttgcacc tgaaagctct tcagaacaaa    80760
acctatattc gctgggatga tggcacaaca gagtcactgt tggagatgct tgattaccag    80820
acagagctag aaaaggtgtt tctgcttgct aaatatccct ctgctattaa tcgtggtgtt    80880
tcatacatca ttgatttgga gtgtgcgaca gataccggtc ggcgtggtat ttcgtcagaa    80940
ctggtatggg atgtatatca agagcttcga acagaacgat gtgtcggaaa gtagcacatt    81000
ggatactaaa gactgcaaaa aactaacgga tctaatgcgc tctggccgta aatttggggc    81060
gacaacttat actgttaaag ttatgagtat tggggctgtt gatgctgtga gcgatagtga    81120
aaaagtagtc gttatagctc gtaacgataa gactggaatg cttgttatga acgaacaggt    81180
tgatgccaaa aatgttagag acaatggtat tcctttgccg agtattcatg acataaattc    81240
agagtttgag taattagtgc ggaaaatcac gaatgttcaa tttcttaaga agaaaaccga    81300
agatatcaat tcccactata gatagggttt cagaagagat tcaaggttat cttcctgact    81360
accaaggccc gactataaat tatcgttttt tctccaattc aaaatatatc ggttcagtga    81420
aaactgagtt gtggaaagag gataatctct tattggttca tgatattagg gcttccacta    81480
caggggtaaa aaatggcact gctatggtca gttggttggt ggctaactct tctgaaatga    81540
tacaacccgt tcatgttatc tgtggtgggt tgggtttctg gtataaattg a              81591
```

```
<210> SEQ ID NO 2
<211> LENGTH: 20
<212> TYPE: DNA
<213> ORGANISM: artificial
<220> FEATURE:
<223> OTHER INFORMATION: primer endA_L

<400> SEQUENCE: 2
gctgttgctt ccaatacgac                                                   20

<210> SEQ ID NO 3
<211> LENGTH: 20
<212> TYPE: DNA
<213> ORGANISM: artificial
<220> FEATURE:
<223> OTHER INFORMATION: primer endA_R

<400> SEQUENCE: 3
ggcgctgcga cttactcatc                                                   20

<210> SEQ ID NO 4
<211> LENGTH: 24
<212> TYPE: DNA
<213> ORGANISM: artificial
<220> FEATURE:
<223> OTHER INFORMATION: primer She_Mph1103F

<400> SEQUENCE: 4
gaaatcttgc agtagcgatg catc                                              24
```

```
<210> SEQ ID NO 5
<211> LENGTH: 34
<212> TYPE: DNA
<213> ORGANISM: artificial
<220> FEATURE:
<223> OTHER INFORMATION: primer She_XmaJR

<400> SEQUENCE: 5
gttgttccta ggctggtgcc atatcaacct ctag                                34
```